United States Patent
Wolf et al.

(10) Patent No.: US 9,051,379 B2
(45) Date of Patent: Jun. 9, 2015

(54) SP1 POLYPEPTIDES, MODIFIED SP1 POLYPEPTIDES AND USES THEREOF

(75) Inventors: Amnon Wolf, Herzlia Pituach (IL); Yehonathan Pouny, Givat Shmuel (IL); Ira Marton, Rechovot (IL); Or Dgany, Ashdod (IL); Arie Altman, Rechovot (IL); Oded Shoseyov, Karmei Yosef (IL)

(73) Assignees: Fulcrum SP Ltd., Herzlia Pituach (IL); Yissum Research Development Company of the Hebrew University of Jerusalem, Jerusalem (IL)

( * ) Notice: Subject to any disclaimer, the term of this patent is extended or adjusted under 35 U.S.C. 154(b) by 100 days.

(21) Appl. No.: 11/988,314

(22) PCT Filed: Jul. 9, 2006

(86) PCT No.: PCT/IL2006/000795
§ 371 (c)(1),
(2), (4) Date: Jan. 4, 2008

(87) PCT Pub. No.: WO2007/007325
PCT Pub. Date: Jan. 18, 2007

(65) Prior Publication Data
US 2009/0062197 A1 Mar. 5, 2009

Related U.S. Application Data

(60) Provisional application No. 60/696,779, filed on Jul. 7, 2005.

(51) Int. Cl.
*A61K 38/00* (2006.01)
*C07K 1/00* (2006.01)
*C07K 14/415* (2006.01)
*A61K 38/17* (2006.01)
*B82Y 30/00* (2011.01)

(52) U.S. Cl.
CPC ............... *C07K 14/415* (2013.01); *A61K 38/17* (2013.01); *B82Y 30/00* (2013.01)

(58) Field of Classification Search
None
See application file for complete search history.

(56) References Cited

U.S. PATENT DOCUMENTS

| 5,073,292 | A  | 12/1991 | Hessel et al. |
| 5,097,025 | A  | 3/1992  | Benfey et al. |
| 7,253,341 | B2 | 8/2007  | Wang et al.   |

(Continued)

FOREIGN PATENT DOCUMENTS

| EP | 0774512      | 5/1997     |
| WO | WO 00/76550  | * 12/2000  |

(Continued)

OTHER PUBLICATIONS

Dgany et al., The structural basis of the thermostability of SP1, a novel plant (*Populus tremula*) boiling stable protein.The structural basis of the thermostability of SP1, a novel plant (*Populus tremula*) boiling stable protein., The Journal of biological Chemistry, E pub Sep. 14, 2004, vol. 279, pp. 51516-51523.*

(Continued)

*Primary Examiner* — Alexander Kim

(57) ABSTRACT

SP1 and modified SP1 variant polypeptides capable of forming reversible molecular associations with substances, compositions-of-matter comprising same, and uses thereof are provided.

24 Claims, 29 Drawing Sheets
(29 of 29 Drawing Sheet(s) Filed in Color)

Transmission electron Microscopy

A Model

(56) References Cited

U.S. PATENT DOCUMENTS

| | | | |
|---|---|---|---|
| 7,445,764 B1* | 11/2008 | Kratz | 424/1.69 |
| 2003/0092624 A1 | 5/2003 | Wang et al. | |
| 2005/0074763 A1 | 4/2005 | Wang et al. | |
| 2006/0172298 A1 | 8/2006 | Wang et al. | |
| 2014/0178483 A1 | 6/2014 | Wolf et al. | |

FOREIGN PATENT DOCUMENTS

| | | |
|---|---|---|
| WO | WO 02/070647 | 9/2002 |
| WO | WO 2004/022697 | 3/2004 |

OTHER PUBLICATIONS

Wacey et al., Disentangling the perturbational effects of amino acid substitutions in the DNA-binding domain of p53., Hum Genet, 1999, vol. 104, pp. 15-22.*

Wylie et al., A biophysical protein folding model accounts for most mutational fitness effects in viruses, Proc Natl Acad Sci U S A. (2011), vol. 108(24), pp. 9916-9921.*

Branden and Tooze, Introduction to Protein Structure (1999), 2nd edition, Garland Science Publisher, pp. 3-12.*

Unger et al., The Genetic Algorithm approach to Protein Structure Prediction, Structure and Bonding (2004), vo. 110, pp. 153-175.*

Grunberg et al., Strategies for protein synthetic biology, Nucleic Acids Research (2010), vol. 38(8), pp. 2663-2675.*

Li et al., Current Approaches for Engineering Proteins with Diverse Biological Properties, Adv Exp Med Biol. (2007-B) vol. 620, pp. 18-33.*

Gentle et al., Direct Production of Proteins with N-terminal Cysteine for Site-Specific Conjugation., Bioconjugate Chem. (2004), vol. 15, pp. 658-663.*

Zitzmann et al., Arginine-Glycine-Aspartic Acid (RGD)-Peptide Binds to Both Tumor and Tumor-Endothelial Cells in Vivo., Cancer Res (2002), vol. 62, pp. 5139-5143.*

Altman et al. "Molecular Biology of Drought Tolerance and Transformation of Populus and Pinus at the Hebrew University of Jerusalem", Dendrome, 3(2): 5-7, 1996. p. 6, 1-h Col., § First, Full.

Anderson "Human Gene Therapy", Nature, 392(6679 Suppl.): 25-30, 1998.

Basler et al. "Hamster (Syrian Golden) PrP Gene, Complete Cds: Scrapie and Cellular PrP Isoforms Are Encoded by the Same Chromosomal Gene", GenBank Accession No. 14054, 1993.

Bradshaw et al. "Populus X Generosa Pop3 Peptide mRNA Complete Cds, Gene Sequences", NCBI Database for Nucleic Sequences, National Center for Biotechnology Information, National Library of Medicine, NIH (Bethesda, MD, USA), Acc.-No. M18538, 2000.

Broun et al. "Catalytic Plasticity of Fatty Acid Modification Enzymes Underlying Chemical Diversity of Plant Lipids", Science, 282: 1315-1317, 1998.

Doerks et al. "Protein Annotation: Detective Work for Function Prediction", Trends in Genetics, 14(6): 248-250, 1998.

Fladung et al. "Excision of the Maize Transposable Element Ac in Periclinical Chimeric Leaves of 35S-Ac-RolC Transgenic Aspen-Populus", Plant Molecular Biology, 33(6): 1097-1103, 1997.

Florack et al. "Expression of Giant Silkmoth Cecropin B Genes in Tobacco", Transgenic Research, 4(2): 132-141, 1995.

Lee et al. "Structure and in Vitro Molecular Chaperone Activity of Cytosolic Small Heat Shock Proteins From Pea", Journal of Biological Chemistry, 270(18): 10432-10438, 1995.

Leung et al. "Thermal Activation of the Bovine Hsc70 Molecular Chaperone at Physiological Temperatures: Physical Evidence of a Molecular Thermometer", Cell Stress and Chaperones, 1(1): 78-89, 1996.

Liautard "Prions and Molecular Chaperones", Archives of Virology, 7(Suppl.): 227-243, 1993.

Liu et al. "Characterization of the Xp21-23 Region in the Wood Region in the Wood Lemming, A Region involved in XY Sex Reversal." Journal of Experimental Zoology, 290:551-557, 2001. Expecially p. 552, col. 2, 1st full §, p. 554, col. 2, Lines 29-36.

Liu et al. "Two Transcription Factors, DREB1 and DREB2, With an EREBP/AP2 DNA Binding Domain Separate Two Cellular Signal Transduction Pathways in Drought- and Low-Temperature-Responsive Gene Expression, Respectively, in *Arabidopsis*", The Plant Cell, 10: 1391-1406, 1998.

Mittler et al. "Inhibition of Programmed Cell Death in Tobacco Plants During a Pathogen-Induced Hypersensitive Response at Low Oxygen Pressure", The Plant Cell, 8: 1991-2001, 1996.

Pelah et al. "Characterization of BspA, A Major Boiling-Stable, Water-Stress-Responsive Protein in Aspen (*Populus tremula*)", Tree Physiology, 15(10): 673-678, 1995.

Prusiner et al. "Prion Protein Biology", Cell, 93: 337-348, 1998.

Shpigel et al. "Immobilization of Recombinant Heparinase I Fused to Cellulose-Binding Domain", Biotechnology and Bioengineering, 65(1): 17-23, 1999.

Soto et al. "Heterologous Expression of a Plant Small Heat-Shock Protein Enhances *Escherichia coli* Viability Under Heat and Cold Stress", Plant Physiology, 120: 521-528, 1999.

Sun et al. "Conformational and Functional Differences Between Recombinant Human Lens $\alpha$A- and $\alpha$B-Crystallin", Journal of Biological Chemistry, 272(10): 6220-6225, 1997.

Sun et al. "Thermodynamic Stability of Human Lens Recombinant $\alpha$A- and $\alpha$B-Crystallins", Journal of Biological Chemistry, 274(48): 34067-34071, 1999.

Wang et al. "Biotechnology of Plant Osmotic Stress Tolerance: Physiological and Molecular Considerations", Proceedings of the IV International symposium on in Vitro Culture and Horticulture Breeding, ISHS, Acta Horticulture, 560: 285-292, 2001.

Wang et al. "Characterization of Sp1, A Stress-Responsive, Boiling Soluble, Homo-Oligomeric Protein From Aspen", Plant Physiology, 130: 865-875, 2002. p. 866, Fig.1, p. 867, Fig.2, p. 871, Fig.8.

Wang et al. "Plant Tolerance to Water and Salt Stress: The Expression Pattern of a Water Stress Responsive Protein (BspA) in Transgenic Aspen Plants", Plant Biotechnology and in Vitro Biology in the 21st Century, p. 561-565, 1999. p. 563, § Bottom.

Supplementary European Search Report and the European Search Opinion Dated Sep. 30, 2009 From the European Patent Office Re.: Application No. 06766122.3.

Translation of Notice of Reason for Rejection Dated Sep. 30, 2009 From the Japanese Patent Office Re.: Application No. 2004-533806.

Bradshaw et al. "Populus x Generosa Pop3 Peptide mRNA, Complete CDS", Database GenBank [Online], Accession No. M18538.1. 2 P., Nov. 30, 2000. URL:http://www.ncbi.nml.nih.gov/nuccore/169458.

Medalsy et al. "SP1 Protein-Based Nanostructures and Arrays", Nano Letters, XP002545658, 8(2): 473-477, Jan. 15, 2008.

Wang et al. "Aspen SP1, An Exceptional Thermal, Protease and Detergent-Resistant Self-Assembled Nano-Particle", Biotechnology and Bioengineering, XP002545656, 95(1): 161-168, May 26, 2006.

Wang et al. "Crystallization and Preliminary X-Ray Crystallographic Analysis of SP1, A Novel Chaperone-Like Protein", Acta Crystallographica Section D, Biological Crystallography, XP002545657, 59(3): 512-514, Mar. 2003.

Communication Pursuant to Article 94(3) EPC Dated Jul. 15, 2009 From the European Patent Office Re.: Application No. 02701532.0.

Communication Pursuant to Article 94(3) EPC Dated Jan. 20, 2010 From the European Patent Office Re.: Application No. 06766122.3.

Communication Pursuant to Article 94(3) EPC Dated Jan. 22, 2010 From the European Patent Office Re.: Application No. 02701532.0.

Communication Pursuant to Article 96(2) EPC Dated Nov. 6, 2006 From the European Patent Office Re.: Application No. 03794033.5.

international Preliminary Examination Report Dated Oct. 11, 2005 From the International Preliminary Examining Authority Re.: Application No. PCT/IL02/00174.

Response Dated Jan. 21, 2010 to Notice of Reason for Rejection of Sep. 30, 2009 From the Japanese Patent Office Re.: Application No. 2004533806.

Response Dated May 20, 2010 to Communication Pursuant to Article 94(3) EPC of Jan. 22, 2010 From the European Patent Office Re.: Application No. 02701532.0.

Requisition by the Examiner Dated Mar. 22, 2010 From the Canadian Intellectual Property Office Re.: Application No. 2,440,358.

(56) References Cited

OTHER PUBLICATIONS

Office Action Dated Jun. 20, 2010 From the Israel Patent Office Re. Application No. 188611 and Its Translation Into English.
Zhang et al. "Suramin Is an Active Site-Directed, Reversible, and Tight-Binding Inhibitor of Protein-Tyrosine Phosphatases", The Journal of Biological Chemistry, 273(20): 12281-12287, 1998.
Communication Pursuant to Article 94(3) EPC Dated Sep. 1, 2008 From the European Patent Office Re.: Application No. 02701532.0.
Communication Pursuant to Article 96(2) EPC Dated Oct. 8, 2007 From the European Patent Office Re.: Application No. 02701532.0.
Communication Pursuant to Article 96(2) EPC Dated Aug. 25, 2006 From the European Patent Office Re.: Application No. 02701532.0.
International Preliminary Report on Patentability Dated Jan. 22, 2009 From the International Bureau of WIPO Re.: Application No. PCT/IL2006/000795.
International Search Report Dated Nov. 3, 2004 From the International Searching Authority Re.: Application No. PCT/IL03/00723.
International Search Report Dated Aug. 13, 2004 From the International Searching Authority Re.: Application No. PCT/IL02/00174.
International Search Report Dated Aug. 14, 2008 From the International Searching Authority Re.: Application No. PCT/IL06/00795.
International Search Report Dated Feb. 26, 2009 From the International Searching Authority Re.: Application No. PCT/IL06/00795.
Invitation to Pay Add. Fees Dated Nov. 21, 2007 From the International Searching Authority Re.: Application No. PCT/IL2006/000795.
Invitation to Pay Additional Fees Dated Jul. 2, 2004 From the International Searching Authority Re.: Application No. PCT/IL03/00723.
Invitation to Pay Additional Fees Dated May 21, 2004 From the International Searching Authority Re.: Application No. PCT/US02/90230 (= PCT/IL02/00174).
Notice of Allowance of Apr. 5, 2007 From the US Patent and Trademark Office Re.: U.S. Appl. No. 10/233,409.
Office Action Dated Jan. 5, 2009 From the Israeli Patent. Office Re.: Application No. 167236 and Its Translation Into English.
Office Action Dated Apr. 13, 2006 From the US Patent and Trademark Office Re.: U.S. Appl. No. 10/233,409.
Office Action Dated Feb. 18, 2008 From the Israeli Patent Office Re.: Application No. 157766.
Office Action Dated Oct. 27, 2008 From the Israeli Patent Office Re.: Application No. 157766 and Its Translation Into English.
Official Action Dated Apr. 6, 2009 From the US Patent and Trademark Office Re.: U.S. Appl. No. 10/526,445.
Official Action Dated Dec. 17, 2008 From the US Patent and Trademark Office Re.: U.S. Appl. No. 10/526,445.
Official Action Dated Dec. 19, 2006 From the US Patent and Trademark Office Re.: U.S. Appl. No. 10/233,409.
Official Action Dated Mar. 22, 2007 From the US Patent and Trademark Office Re.: U.S. Appl. No. 10/526,445.
Official Action Dated May 22, 2006 From the US Patent and Trademark Office Re.: U.S. Appl. No. 10/468,841.
Official Action Dated Jul. 26, 2007 From the US Patent and Trademark Office Re.: U.S. Appl. No. 10/526,445.
Official Action Dated Oct. 29, 2007 From the US Patent and Trademark Office Re.: U.S. Appl. No. 10/526,445.
Supplementary European Search Report Dated Aug. 16, 2005 From the European Searching Authority Re.: Application No. 02701532.0.
Written Opinion Dated Aug. 14, 2008 From the International Searching Authority Re.: Application No. PCT/IL06/00795.
Written Opinion Dated Feb. 17, 2005 From the International Searching Authority Re.: Application No. PCT/US02/90230.
Written Opinion Dated Feb. 26, 2009 From the International Searching Authority Re.: Application No. PCT/IL06/00795.
Response Dated Jul. 18, 2010 to Communication Pursuant to Article 94(3) EPC of Jan. 20, 2010 From the European Patent Office Re.: Application No. 06766122.3.
Response Dated Sep. 21, 2010 to Requisition by the Examiner of Mar. 22, 2010 From the Canadian Intellectual Property Office Re.: Application No. 2,440,358.
Supplementary European Search Report Dated Mar. 22, 2006 From the European Patent Office Re. Application No. EP 0379433.
Translation of Notice of Reason for Rejection Dated Dec. 2, 2011 From the Japanese Patent Office Re. Application No. 2008-520063.
Office Action Dated Dec. 22, 2011 From the Israel Patent Office Re. Application No. 188611 and Its Translation Into English.
Requisition by the Examiner Dated Jan. 7, 2013 From the Canadian Intellectual Property Office Re. Application No. 2,613,619.
Translation of Notice of Reason for Rejection Dated Dec. 28, 2010 From the Japanese Patent Office Re.: Application No. 2004-533806.
Office Action Dated Nov. 16, 2010 From the Israel Patent Office Re. Application No. 204767 and Its Translation Into English.
Communication Pursuant to Article 94(3) EPC Dated Mar. 26, 2012 From the European Patent Office Re.: Application No. 06766122.3.
Communication Pursuant to Rule 58 EPC or Rule 159 EPC, Invitation to Remedy Deficiencies in the Application Documents Dated Mar. 19, 2012 From the European Patent Office Re. Application No. 12151669.4.
Translation of Notice of Reason for Rejection Dated Apr. 3, 2012 From the Japanese Patent Office Re. Application No. 2008-520063.
Response Dated Mar. 14, 2011 to Office Action of Nov. 16, 2010 From the Israel Patent Office Re. Application No. 204767.
Partial European Search Report Dated Jun. 20, 2012 From the European Patent Office Re. Application No. 12151669.4.
Katz et al. "Integrated Nanoparticle-Biomolecule Hybrid Systems: Synthesis, Properties, and Applications", Angewandte Chemie International Edition, XP055029649, 43(45): 6042-6108, Nov. 19, 2004.
Sarikaya et al. "Molecular Biomimetics: Nanotechnology Through Biology", Nature Materials, XP002471442, 2(9): 577-585, Sep. 1, 2003. Table 1.
Von Nickisch-Rosenegk et al. "Chemically Synthesized Zinc Finger Molecules as Nano-Addressable Probes for Double-Stranded DNAs", Journal of Nanobiotechnology, XP021008671, 3(5): 1-6, Jun. 29, 2005. Abstract.
Willner "Biomaterials for Sensors, Fuel Cells, and Circuitry", Science, XP055029648, 298(5602): 2407-2408, Dec. 20, 2002.
Communication Pursuant to Article 94(3) EPC Dated Jan. 11, 2011 From the European Patent Office Re.: Application No. 06766122.3.
Response Dated Jul. 7, 2011 to Communication Pursuant to Article 94(3) EPC of Jan. 11, 2011 From the European Patent Office Re.: Application No. 06766122.3.
Requisition by the Examiner Dated Aug. 23, 2010 From the Canadian Intellectual Property Office Re.: Application No. 2,497,719.
European Search Report and the European Search Opinion Dated Oct. 10, 2012 From the European Patent Office Re. Application No. 12151669.4.
Communication Pursuant to Rules 70(2) and 70a(2) EPC and Reference to Rule 39(1) EPC Dated Nov. 12, 2012 From the European Patent Office Re. Application No. 12151669.4.
Requisition by the Examiner Dated Nov. 15, 2011 From the Canadian Intellectual Property Office Re.: Application No. 2,440,358.
Office Action Dated Nov. 22, 2012 From the Israel Patent Office Re. Application No. 204767 and Its Translation Into English.
Translation of Notice of Reason for Rejection Dated Aug. 9, 2013 From the Japanese Patent Office Re. Application No. 2012-42816.
Office Action Dated Feb. 5, 2013 From the Israel Patent Office Re. Application No. 188611 and Its Translation Into English.
Requisition by the Examiner Dated Dec. 27, 2013 From the Canadian Intellectual Property Office Re. Application No. 2,613,619.
Office Action Dated Mar. 17, 2014 From the Israel Patent Office Re. Application No. 204767 and Its Translation Into English.
Office Action Dated May 29, 2014 From the Israel Patent Office Re. Application No. 188611 and Its Translation Into English.
Requisition by the Examiner Dated Jul. 24, 2014 From the Canadian Intellectual Property Office Re. Application No. 2,613,619.
Reeck et al. "Homology in Proteins and Nucleic Acids: A Terminology Muddle and a Way Out of It", Cell, 50: 667, Aug. 28, 1987.
Communication Pursuant to Article 94(3) EPC Dated Oct. 30, 2014 From the European Patent Office Re. Application No. 12151669.4.
Restriction Official Action Dated Nov. 20, 2014 From the US Patent and Trademark Office Re. U.S. Appl. No. 14/191,479.

* cited by examiner

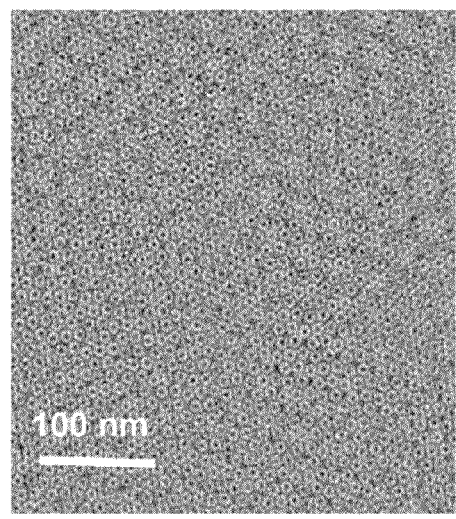
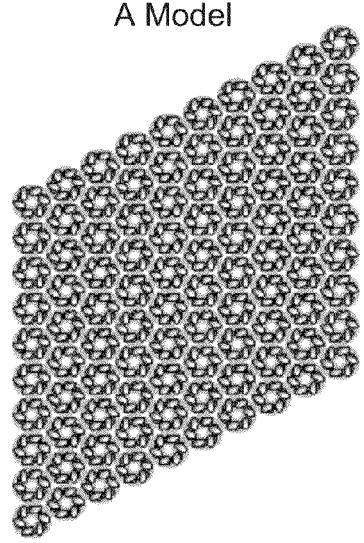
Fig. 1
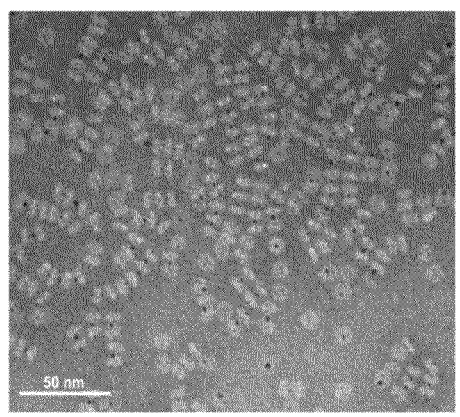
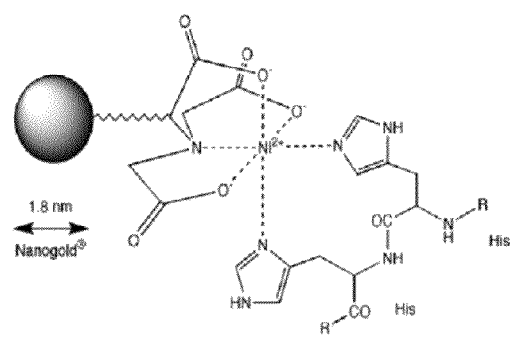
Fig. 2a-b

Hydrophobic interaction Chromatography of ion exchange peak

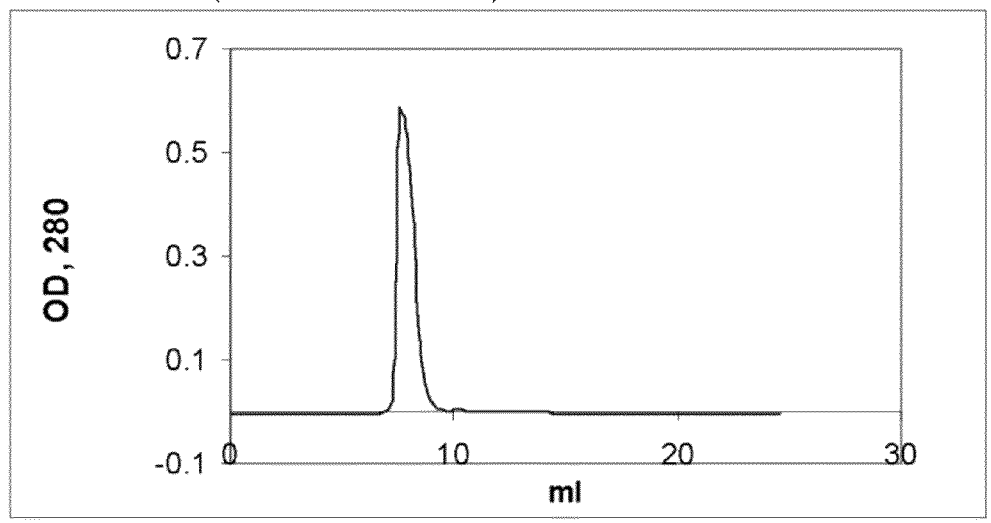
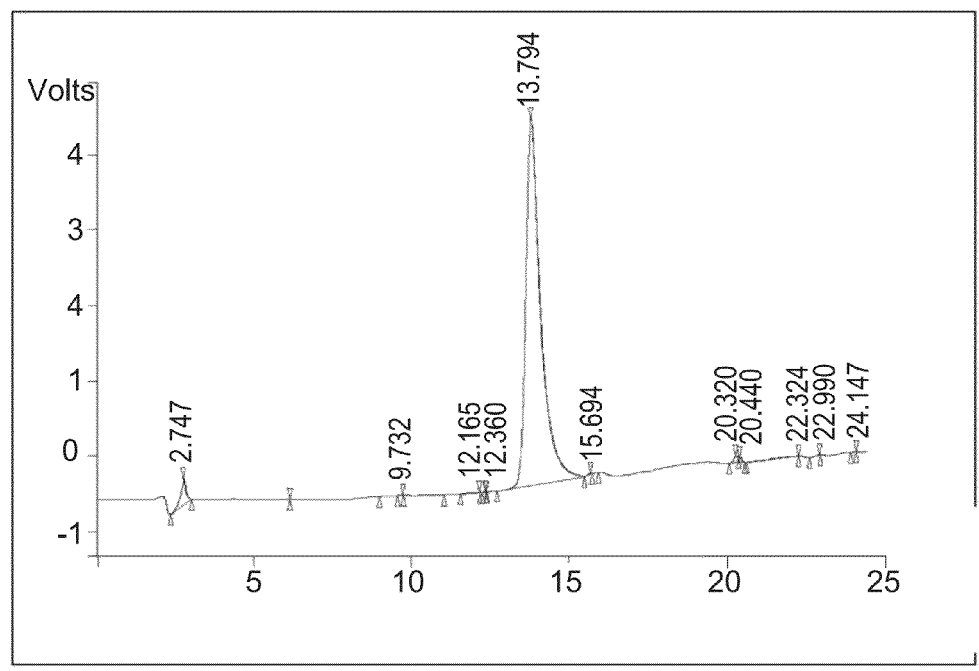
Fig. 7

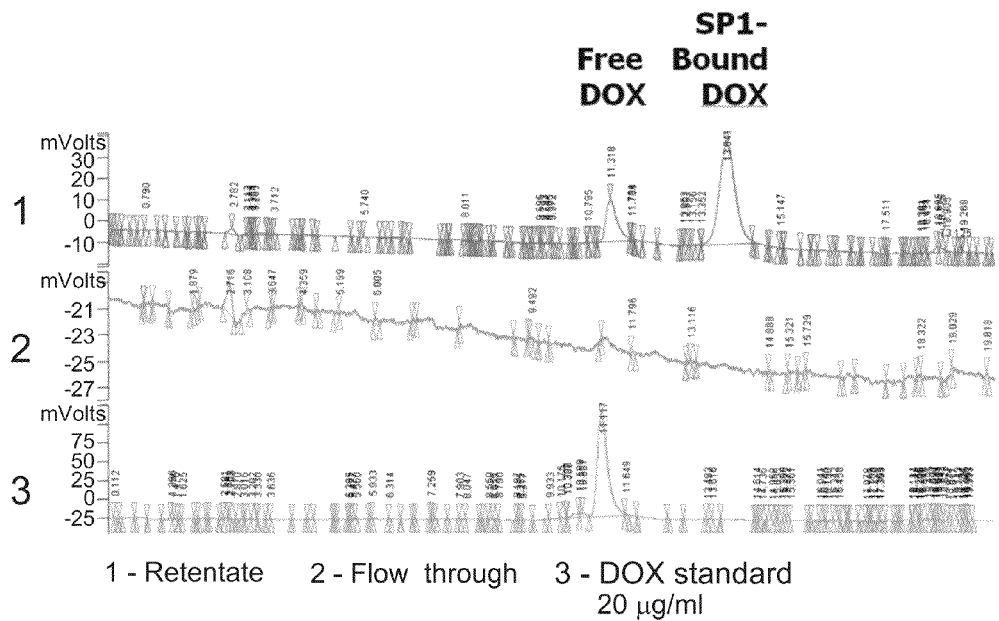
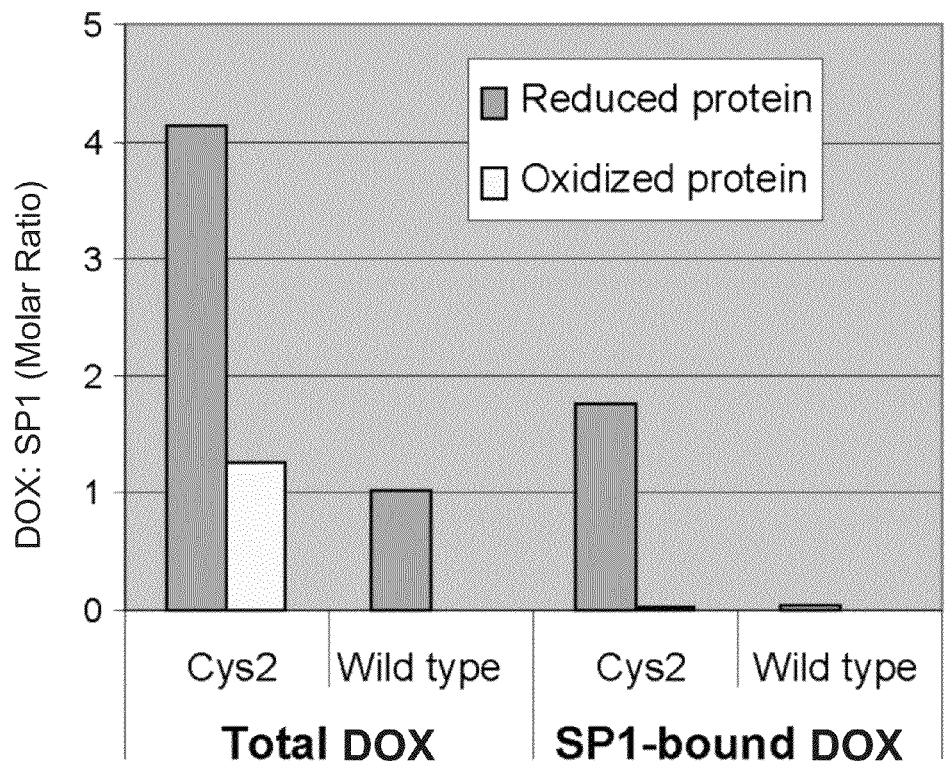
Fig. 14

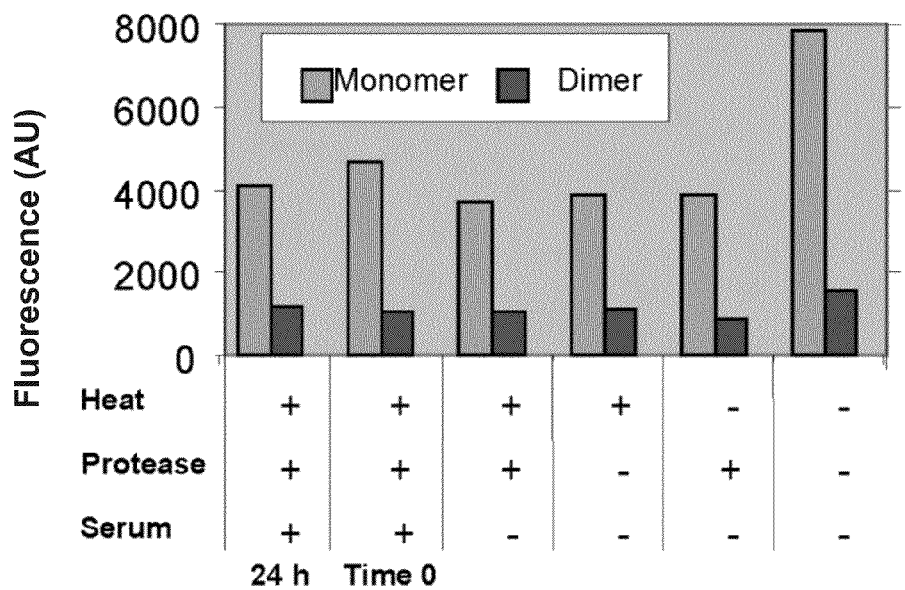
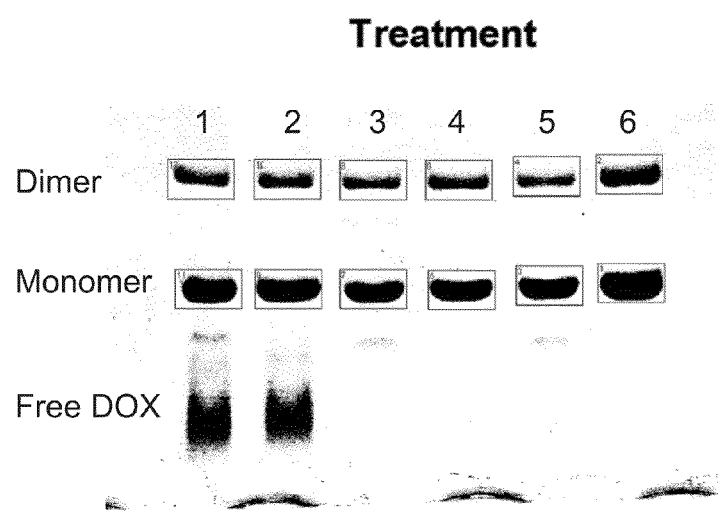
Fig. 16

| Lane | SP1 variant | solvent |
|---|---|---|
| 1 | Wild type | Sodium phosphate pH 7 |
| 2 | Wild type | Methanol |
| 3 | Wild type | Hexane |
| 4 | Cys2 | Sodium phosphate pH 7 |
| 5 | Cys2 | Methanol |
| 6 | Cys2 | Hexane |

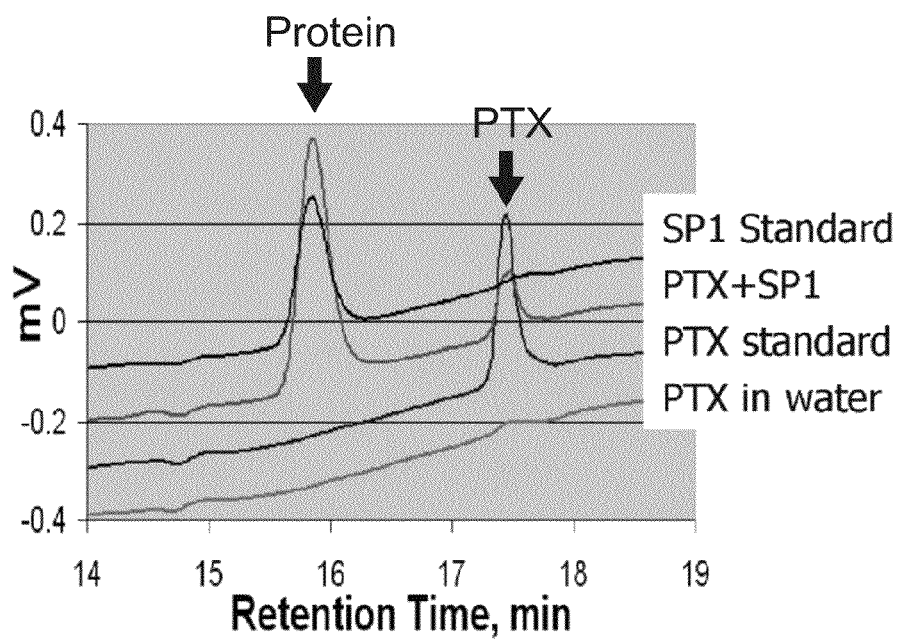
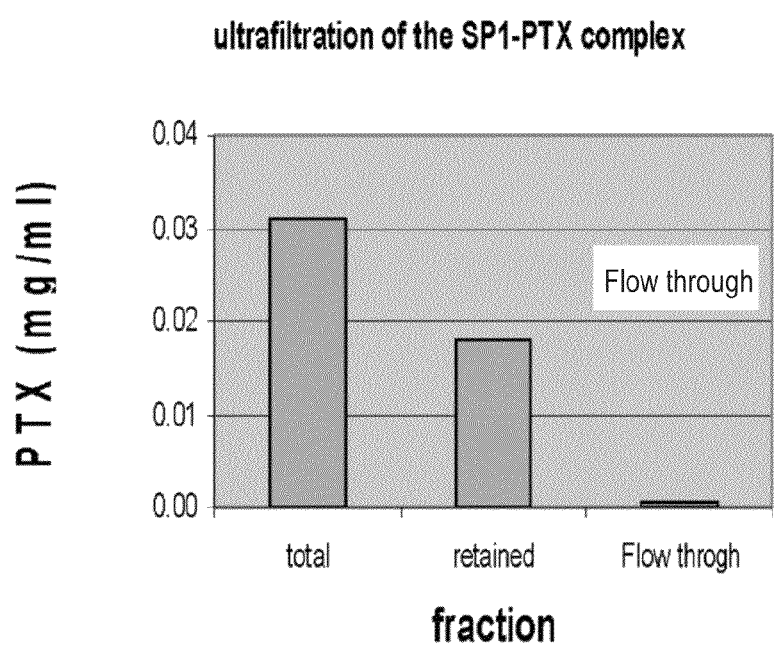
Fig. 19

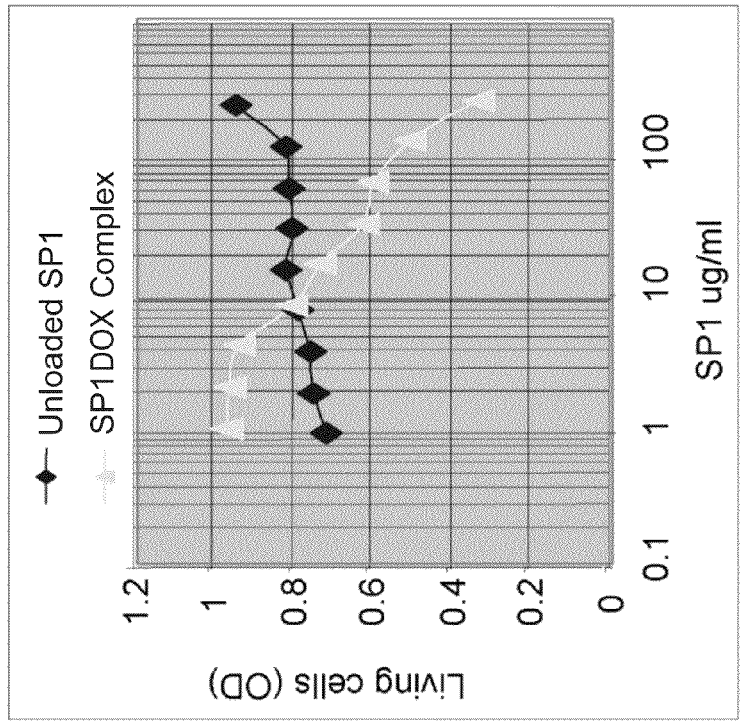
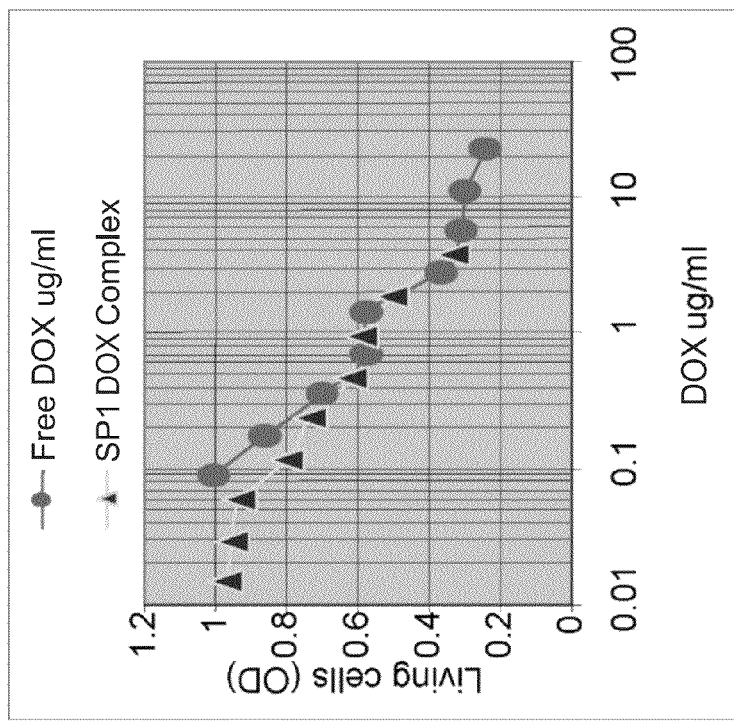
Fig. 24a
Fig. 24b

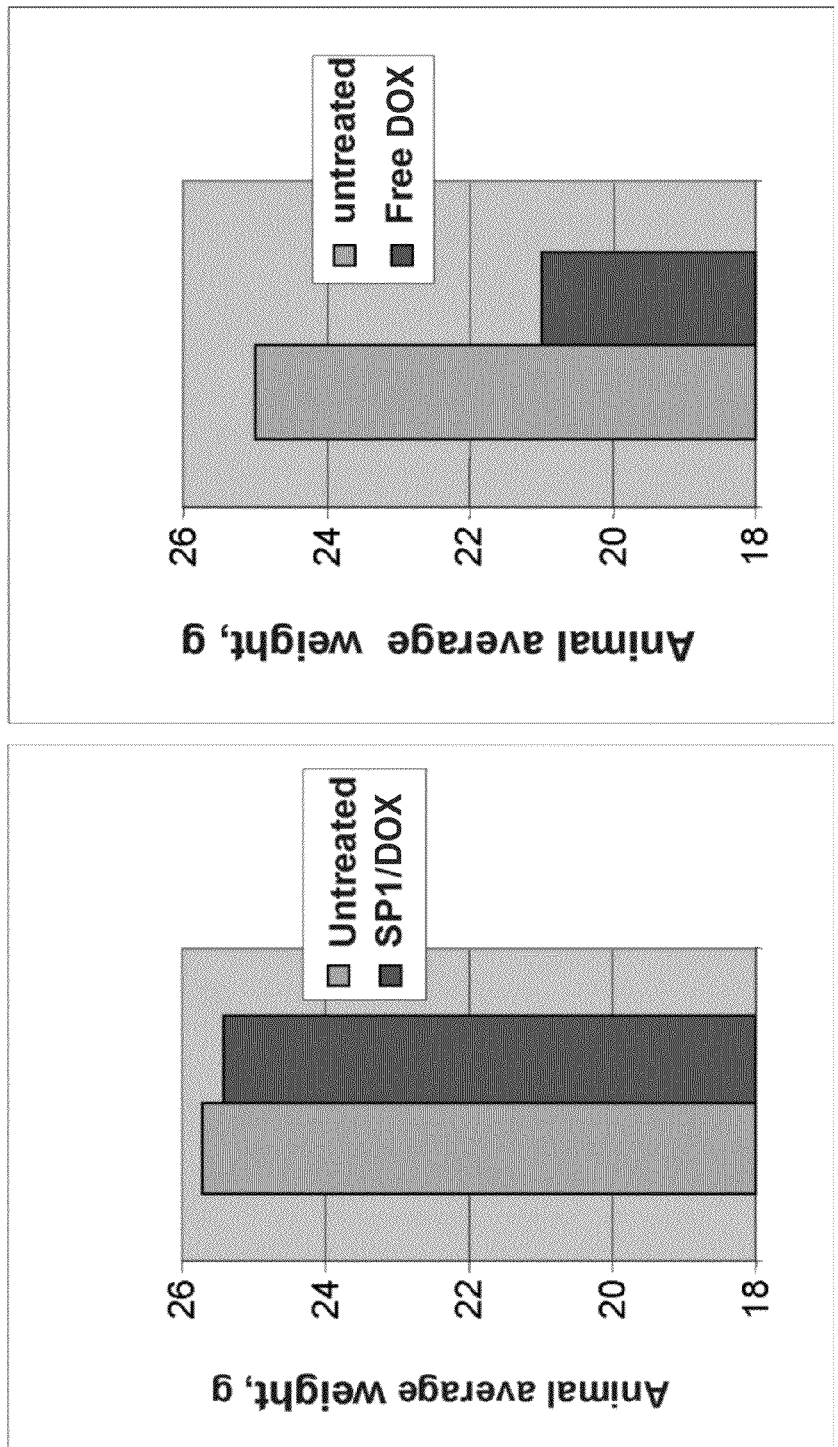

SP1 POLYPEPTIDES, MODIFIED SP1 POLYPEPTIDES AND USES THEREOF

RELATED APPLICATIONS

This Application is a National Phase of PCT Patent Application No. PCT/IL2006/000795 having International Filing Date of Jul. 9, 2006, which claims the benefit of U.S. Provisional Patent Application No. 60/696,779 filed on Jul. 7, 2005. The contents of the above Applications are all incorporated herein by reference.

FIELD AND BACKGROUND OF THE INVENTION

The present invention relates to denaturant and protease stable proteins, modified derivatives thereof, and uses thereof. More particularly, the present invention relates to the use of novel denaturant-stable, protease resistant, homo-oligomeric proteins, also referred to herein as stable proteins (SPs), and derivatives thereof designed for complexing, release and delivery of other molecules (ligands) and nanostructures.

Denaturant-Stable, Protease Resistant Proteins

A unique family of stress-induced, chaperone-like proteins having exceptional resistance to harsh conditions has been recently identified in widely diverse plant species. Exemplified by the SP1 protein of Aspen (SEQ ID NO: 1), this family of proteins is characterized by boiling-, denaturant- and protease-resistance, regions of conserved amino acid sequence homology, unique three-dimensional conformation, oligomer formation and a strong stabilizing effect on biologically active proteins.

The exceptional resistance of these stress-induced, chaperone-like proteins to harsh conditions in combination with their unique three dimensional structure allows the application of extreme condition to create stable, but selectively reversible complexes with the ligand.

SP1

SP1, isolated from aspen plants (*Populus tremula*), responds to a wide range of environmental stresses, including salinity, cold and heat stress and accumulates during stress recovery. No significant sequence similarity has been found with known protein families and SP1 homologues have been observed in a number of plant and bacterial species, either as putative proteins from genomic sequences or ESTs with unknown function.

Wang et al. (U.S. patent application Ser. No. 10/233,409) have isolated, cloned and characterized the Aspen SP1 protein (SEQ ID NO: 1), and uncovered it's chaperone-like activity in stabilizing other, biologically active proteins against denaturation. Wang et al (U.S. patent application Ser. No. 10/233,409) further disclosed other boiling and detergent-stable proteins from other, diverse plant species (Tomato, Pine, Rice, Corn and *Arabidopsis*) sharing similar functional characteristics, specifically, chaperone-like activity and stress-relatedness, sharing immune-cross reactivity, having at least 65% amino acid homology to the Aspen SP1, and sharing a conserved region of sequence homology.

Wang et al (U.S. patent application Ser. No. 10/233,409) disclosed SP1 proteins fused to other protein or non-protein molecules, for enhancement of binding properties of binding molecules, for stabilization of the fused molecules (such as enzymes) and for enhancement or alteration of immunological properties of the fused molecules. SP1 fusion proteins, as taught by 10/233,409, comprise recombinant SP1 molecules having additional polypeptide sequences added by genetic engineering techniques, and SP1 molecules having additional non-protein moieties added by chemical means, such as cross linking. Wang et al have further disclosed the therapeutic use of SP1 proteins for strengthening skin, hair, nails, etc. However, U.S. patent application Ser. No. 10/233,409 do not teach, nor imply, the use of native SP1, or SP1 variants as carriers for and means of controlled release of, agents (therapeutic, cosmetic, diagnostic, conductive, etc) reversibly complexed therewith.

Drug Carriers:

Many drugs employed to treat diseases are either insufficiently soluble in aqueous solutions or have adverse side effects in therapeutic concentrations. Thus, many medical applications suffer from a lack of suitable methods for efficiently delivery of effective concentrations of drugs to a target cell or tissue in an organism (e.g., mammal) in need of treatment.

Some considerations for efficacious use of drugs include:

Poor solubility, causing difficulty in achieving a convenient pharmaceutical format, as hydrophobic drugs may precipitate in aqueous media. However, the use of excipients for solubilization such as Cremphor (the solubilizer for paclitaxel in Taxol) is also associated with toxicity.

Lack of selectivity for target tissues, leading to toxicity to normal tissues, severely restricting the amount of drug that can be administered, as in the case of the cardiac toxicity of doxorubicin. Low concentrations of drugs in target tissues further results in suboptimal therapeutic effects.

Unfavorable pharmacokinetics, such as rapid renal clearance, rapid breakdown of the drug in vivo, or loss of activity at physiological conditions (e.g. loss of activity of camptothecins at physiological pH), can also lead to heightened dosing or a frequent administration regimen.

Development of drug resistance in target tissue, such as tumors, by induction of cellular transporters, detoxification pathways, or inhibition of apoptosis transduction pathways.

Tissue damage on extravasation of cytotoxic drugs, leading to tissue damage (i.e. necrosis caused by free paclitaxel).

A number of approaches have resolved some of these issues in specific cases, but there is yet no general solution to the problems of drug delivery. Some examples of existing approaches for solving these problems include (1) solublization of hydrophobic drugs in micelles formed from surfactants in aqueous media (Wiedmann and Kamel, J. Pharm. Sci. 2002, 91, 1743; MacGregor, et al., Adv. Drug Deliv. Rev. 1997, 25, 33), (2) encapsulation of drugs in polymeric matrices in the nanometer to micrometer size range which may be biodegradable and may contain bioadhesive functional groups or ligands (WO 02/15877, WO 02/49676), (3) encapsulation of hydrophilic drugs in liposomes (Anderson, et al., Pharm. Res. 2001, 18, 316; WO 99/33940), which may also display bioadhesive functional groups or ligands, (4) conjugation of drugs to molecules that are substrates for active transport systems (Kramer, et al., J. Biol. Chem. 1994, 269, 10621; WO 01/09163; US 2002/0098999; US 20060074225), (5) targeting using physiologically selective (pH, enzymatic, etc.) release of active drug components (i.e. prodrugs), (6) association of the drug with hydrogels and (7) chemical derivatization of protein drugs with hydrophilic polymers to protect them from degradation, immune recognition, or renal excretion (Belcheva, et al., Bioconjugate Chem. 1999, 10, 932; Zalipsky, Bioconjugate Chem. 1995, 6, 150; U.S. Pat. No. 4,002,531; U.S. Pat. No. 4,179,337). None of these approaches, however, offers a general solution for all cases of drug delivery problems. Control of particle size in micellar, liposomal, and polymeric nanoparticulate systems remains a serious problem. The inability of currently available drug delivery systems to incorporate all of the functions required for delivery into a single system is another problem with for example, micelles, nanoparticulate systems and targeted systems. Yet further, the release rate and storage life, especially of micelles and liposomes, is difficult to control and unpredictable, and amphiphylic components can produce toxic effects.

Other systems employed for drug delivery to a cell or tissue of an organism have similar drawbacks. Thus, there is a need for a method to deliver drugs that minimize or overcome the above-referenced problems.

The invention includes methods for the use of SP1 and SP1 variants for forming molecular complexes with other substances such as small molecules, peptides, nucleic acid fragments, inorganic nanostructures and other molecules (ligands). In addition the invention includes methods for the use of SP1 and SP1 variants for molecular complexing of drugs and delivery as well as control release of complexed ligands. There is thus a widely recognized need for, and it would be highly advantageous to have, SP1 and SP1 variants capable of forming molecular complexes devoid of the above limitation.

SUMMARY OF THE INVENTION

According to one aspect of the present invention there is provided an isolated polypeptide comprising an amino acid sequence of an SP1 polypeptide, said amino acid sequence being modified to be in a reversible molecular association with a substance.

According to yet another aspect of the present invention, there is provided an isolated polypeptide comprising an amino acid sequence as set forth in SEQ ID NO:2-30.

According to still another aspect of the present invention, there is provided an isolated polynucleotide comprising a nucleic acid sequence encoding a polypeptide having an amino acid sequence as set forth in SEQ ID NO: 2-30, or an isolated polynucleotide encoding an isolated polypeptide comprising an amino acid sequence of an SP1 polypeptide, said amino acid sequence being modified to be in a reversible molecular association with a substance.

According to another aspect of the present invention, there is provided a composition of matter comprising a plurality of self-assembled modified SP1 monomers.

According to yet another aspect of the present invention, there is provided an isolated composition-of-matter comprising a therapeutic, diagnostic or cosmetic agent being in molecular association with a modified SP1 polypeptide.

According to further features in the preferred embodiments of the invention described below, the SP1 molecule is translationally fused to the agent.

According to still another aspect of the present invention, there is provided an isolated composition-of-matter comprising an SP1 polypeptide in reversible molecular association with a therapeutic, diagnostic or cosmetic agent.

According to further features in the preferred embodiments of the invention described below, the SP1 molecule is not translationally fused to the agent.

According to yet another aspect of the present invention, there is provided an isolated composition-of-matter comprising a conductive or semi-conductive substance being in molecular association with a modified SP1 polypeptide.

According to yet another aspect of the present invention, there is provided an isolated composition-of-matter comprising an SP1 polypeptide in reversible molecular association with a conductive or semi-conductive substance.

According to yet another aspect of the present invention, there is provided a method of delivering a therapeutic, diagnostic or cosmetic agent to a subject in need thereof, the method comprising administering to the subject a therapeutically effective amount of the composition of matter of comprising a therapeutic, diagnostic or cosmetic agent being in molecular association with a SP1 polypeptide to the subject, thereby delivering said therapeutic, diagnostic or cosmetic agent to said subject.

According to further features in the preferred embodiments of the invention described below the SP1 polypeptide can be a modified SP1 polypeptide.

According to yet further features in the preferred embodiments of the invention described below, the molecular association is a reversible molecular association, and the method further comprising providing conditions for reversing said molecular association.

According to yet another aspect of the present invention, there is provided a method of stabilizing a substance, the method comprising contacting the substance with an SP1 polypeptide modified to reversibly form a complex with said substance so as to form a complex, thereby stabilizing the substance.

According to further features in the preferred embodiments of the invention described below, the stability comprises a property selected from the group consisting of temperature stability, ionic strength stability, protease stability and catalytic stability.

According to further features in the preferred embodiments of the invention described below, the method further comprising the step of contacting said complex with a solvent, so as to form a solution.

According to yet another aspect of the present invention, there is provided a method of enhancing the solubility of a substance in a solution. The method is effected by contacting the substance with an SP1 polypeptide capable of reversibly forming a complex with said substance so as to form a complex and dissolving said complex with a solvent so as to form a solution, thereby enhancing the solubility of the substance in the solution. The solvent can be an aqueous or organic solvent, and the substance can be a hydrophobic or hydrophilic substance.

According to further features in the preferred embodiments of the invention described below, the SP1 polypeptide is a boiling and detergent stable protein at least 65% homologous to SEQ ID NO: 1, said boiling and detergent stable protein having a chaperone-like activity and being capable of forming stable dimers.

According to yet further features in the preferred embodiments of the invention described below the SP1 polypeptide has at least one conserved amino acid sequence in at least one region corresponding to amino acids 9-11, 44-47 and/or 65-73, of SEQ ID NO:1, as determined using a Best Fit algorithm of GCG, Wisconsin Package Version 9.1, using a plurality of 10.00, a threshold of 4, average weight of 1.00, average match of 2.91 and average mismatch of minus 2.00.

According to still further features in the preferred embodiments of the invention described below the SP1 polypeptide is characterized by oligomer formation, and the SP1 oligomer is a heat stable and protease resistant oligomer.

According to further features in the preferred embodiments of the invention described below the SP1 polypeptide is an SP1 polypeptide having a modified amino acid sequence, and the modification comprises addition of at least one amino acid capable of forming disulfide bonds.

According to further features in the preferred embodiments of the invention described below the modification comprises addition of at least 2 histidine residues at a position corresponding to amino acid residue 2 of SEQ ID NO: 1.

According to still further features in the preferred embodiments of the invention described below the modification comprises the addition of at least one amino acid having at least one thiol group at a position corresponding to amino acid residue 40 of SEQ ID NO:1.

According to yet further features in the preferred embodiments of the invention described below, forming the molecular association or complex with the agent is redox-dependent.

According to still further features in the preferred embodiments of the invention described below the modification is an addition of a cysteine residue at a position corresponding to amino acid residue 2 or 40 of SEQ ID NO:1.

According to further features in the preferred embodiments of the invention described below the substance is a therapeutic agent, a diagnostic agent or a cosmetic agent. Yet further, the therapeutic agent, diagnostic agent or cosmetic agent is selected from the group consisting of a polypeptide agent, a nucleic acid agent, a lipid agent, a carbohydrate agent, a small molecule and a combination of same.

According to further features in the preferred embodiments of the invention described below, the substance is a conductive or semiconductive ionic substance. The conductive or semiconductive ionic substance can be any of metals, semiconductors and dielectrics.

According to further features in the preferred embodiments of the invention described below, the modified amino acid sequence is as set forth in SEQ ID NO:2-30.

According to further features in the preferred embodiments of the invention described below, the said amino acid sequence is modified to comprise a target recognition sequence. The target recognition sequence can be a cancer cell surface or cancer cell vasculature recognition sequence. The target recognition sequence can be any of the sequences of SEQ ID NOs: 31-62. The target recognition sequence can be a cancer cell vasculature recognition sequence is selected from the group consisting of SEQ ID NOs: 63-81. The cancer cell vascular recognition sequence can be a CRGD (SEQ ID NO: 151) sequence.

According to further features in the preferred embodiments of the invention described below, the molecular association is a covalent association or a non-covalent association.

According to yet another aspect of the present invention, there is provided the use of a composition of matter comprising a therapeutic, diagnostic or cosmetic agent being in molecular association with a native or a modified SP1 polypeptide for the manufacture of a medicament for delivering a therapeutic, diagnostic or cosmetic agent to a subject in need thereof.

According to still another aspect of the present invention, there is provided a of a composition of matter comprising a therapeutic, diagnostic or cosmetic agent being in molecular association with a native or a modified SP1 polypeptide for the delivering a therapeutic manufacture of a medicament for delivering a therapeutic, diagnostic or cosmetic agent to a subject in need thereof.

The present invention successfully addresses the shortcomings of the presently known configurations by providing isolated SP1 polypeptides and —SP1 variant polypeptides capable of forming molecular associations with substances for use in therapeutic, diagnostic, cosmetic and nano-technological applications, such as drug delivery, solubilization and stabilization.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is an electron micrograph of a negatively stained 2D crystal of SP1 oligomer, and a graphic representation of the 2D crystalline structure;

FIGS. 2a-2b are electron micrographs of recombinant SP1: 6HSP1 showing binding of NTA-Ni gold nano-particles to the 6H tags in the central cavity. FIG. 2a is a transmission electron micrograph (TEM); Note the alternating sequence of Protein-nanogold-Protein-nanogold . . . ; FIG. 2b is a graphic representation of the nanogold-6HS-SP1 conjugate;

FIG. 3 is a SDS-PAGE showing the self-assembly of two SP1 variants into hetero-oligomer SP1 complexes. Monomers of recombinant HIS-tagged SP1 (6H) and N-terminal deleted SP1 (ΔN) were co-electro-eluted (6HΔN), and purified on the Ni-NTA Agarose and subjected to Proteinase K (PK) digestion. Protein samples were prepared in SDS-sample buffer with excess ratio of SDS to the sample, either boiled (b) for 5 min, or without boiling (nb). Lane 1=WT: wild type SP1. Boiled, monomeric, gel purified forms of 6HSP1 (lane 2) and ΔNSP1 (lane 3) were visualized by Coomassie blue staining, excised and mixed at 1:1 ratio (v/v) (lanes 4 and 5). The proteins were co-eluted by electro-elution as described previously (Wang (2002)). The hetero-oligomeric complex was isolated on Ni-NTA Agarose beads (lanes 6 and 7). Proteinase K which digests monomeric SP1 but not SP1 complex, was employed to eliminate the monomeric form of 6HSP1 and ΔNSP1 from the Ni-NTA purified proteins (lanes 8 and 9). The composition of hetero-olimeric SP1 was determined by SDS-PAGE and visualized by silver staining;

FIG. 4 shows the multiple display of the tumor specific peptides CRGD (SEQ ID NO: 151) and RGDC (SEQ ID NO: 152) on SP1 surface. The peptides were inserted to SP1 N-terminus. Note that in both the CRGD (lanes 1-3 )(SEQ ID NO: 5), and the RGD-C (lanes 5-7)(SEQ ID NO: 6) variants form high molecular weight complexes (lanes 3 and 7). When the protein is boiled in the sample application buffer in the presence of reducing agent the complex is dissociated to lower molecular weight species (monomer, dimer and others). In the absence of reducing agents(lanes 1 and 5), and boiling under oxidizing conditions (in the absence of reducing agents) higher levels of dimers are observed (lane 2). Lane 4=molecular weight markers;

FIGS. 5a and 5b are photographs of PAGE analysis showing the expression, purification and refolding of recombinant variant SP1. Cys2loop1RGd SP1 variants not forming soluble protein during expression (found in inclusion bodies, IB) extracted by French press and sedimented by centrifugation (20 min. 17,000×g). The supernatant which does not contain soluble SP1 (FIG. 5a, lane 1) was collected, and the pellet which contain the SP1 IB (FIG. 5a, lane 2) was washed in dilute urea, and solubilized in 5M urea and 10 mM DTT, centrifuged (30 min. 20000×g). The pellet (FIG. 5a, lane 3) was discarded, and the supernatant was collected and dialyzed against buffer with 2 mM DTT for four days (FIG. 5a, lane 4). The dialyzed variant SP1 was stored in cold 3 weeks, (FIG. 5b, lanes 1 and 2), SP1 monomer as well as non specific proteins were removed by heat treatment for 30 min, digested by protease (alcalase, 10,000: dilution, FIG. 5b) and dialyzed (FIG. 5b, lane 4). MW=molecular weight markers (upper band=SP1 complex, lower band=SP1 monomer). Note the shift from uncomplexed lower molecular weight forms (FIG. 5a, lanes 2 and 4; FIG. 5b, lanes 1 and 2) to higher molecular weight, oligomeric forms (FIG. 5b, lanes 3 and 4);

FIGS. 6a-6c shows the purification of recombinant SP1 from the crude, heat-resistant extract of recombinant cells, using both Ion Exchange (FIG. 6a) and Hydrophobic Interaction Chromatography (FIG. 6b). FIG. 6c is a PAGE analysis of the crude recombinant cell extract (lane 1) and heat resistant fraction (lane 2), compared to the purified product of separation on a Source-Q hydrophobic interaction column;

FIG. 7 shows the characterization of pure SP1, eluting as a single peak on both gel filtration HPLC (TSK300 column) (upper) and reverse phase HPLC (C-18 column) (lower);

FIGS. 8a-8c are a graphic representation illustrating a hypothetical model of drug complex formation and controlled release by the Cys2 SP1 variant. FIG. 8a shows a model for redox-dependent opening and closing of the central cavity of the Cys2 variant, dependent on a dynamic equilibrium between free thiols and disulfide bonds: reducing agents shift the equilibrium towards the free thiols and oxidizing reagents shift the equilibrium towards the disulfide bond. FIG. 8a is a SDS-PAGE illustrating the predominance of Cys 2 SP1 monomers under reducing conditions (boiling for 10 min in LSB+2% b-mercaptoethanol) (lane 1), and Cys 2 SP1 dimers under non-reducing conditions (lane 2). FIG. 8c is a graphic representation illustrating the redox-dependent drug complex formation by the Cys2 SP1 variant.

FIG. 9 is a histogram showing redox-dependent complex formation with small molecules by Cys2 SP1. Pure Cys 2 mutant (1.5 mg/ml in Phosphate buffered saline, pH=7.5 (PBS)) was incubated for 2 hours at room temp, with 1 mM fluorescein-amine with or without glutathione (reduced form, GSH 3 mM). Binding reaction was stopped by adding hydrogen peroxide (0.01%), followed by ultra filtration (using a 30 kD cutoff filter) and extensive wash. Absorption analysis was conducted at both 278 and 492 nm, and the results expressed as the 492/278 ratio. Note that in the absence of the reducing agent (GSH), retention of the flourescein-amine is negligible;

FIG. 10 is a graphic representation of the redox-dependent fluorescein amine complex formation by Cys2 SP1, compared to the recombinant SP1. Fluorescein-amine was incubated with pure SP1 or Cys2 SP1 mutant (1.5 mg/ml in PBS pH=7.5) in the absence or presence of DTT (10 mM). Binding reaction was stopped by adding hydrogen peroxide (0.01%), followed by ultra filtration (using 30 kD cutoff filter) and extensive wash. Samples were analyzed by Gel filtration HPLC, and detected at both 228 and 490 nm. Calculated data is shown on the right. Note the superior retention of the fluorescein-amine by Cys2 SP1 mutant under reducing conditions (10 mM DTT);

FIG. 11 is a histogram illustrating the concentration dependent complex formation with fluorescein-amine by Cys2 SP1. Fluorescein-amine (10, 33, 100 or 333 mM) was incubated with Cys 2 SP1 or pure wild type SP1 in the presence of 10 mM DTT, and the bound and unbound fractions analyzed by ultra-filtration and HPLC as in FIG. 10. Note the superior binding by Cys2 SP1 of high concentrations of Cys2 SP1;

FIG. 12 is a histogram showing the superior, redox-dependent complex formation with Doxorubicin by Cys2 SP1. Pure wild type SP1 or Cys2 SP1 mutant (1.5 mg/ml in 20 mM Sodium Phosphate buffered, pH=6.8) were incubated overnight at room temp, with DOX 1 mg/ml in the presence of DTT (10 mM), with gentle rolling. Binding reaction was stopped by adding hydrogen peroxide (0.01%), followed by ultra filtration (using 30 kD cutoff filter) and extensive wash until follow-through become colorless. Optical density was measured at both 278 and 477 nm using nanodrop spectrophotometer. Note the dramatic effect of the reducing agent on drug binding by the Cys2 SP1, compared to the absence of effect on the wild type SP1.

FIG. 13 is a histogram illustrating the redox-dependent release of Doxorubicin by Cys2 SP1. Doxorubicin (DOX) was complexed within Cys2 SP1 as described in FIGS. 9-12 above. Release of the drug in the presence of 0, 2 and 20 mM GSH was measured by ultrafiltration and size exclusion HPLC analysis (detection at 228 and 475 nm);

FIG. 14 is a histogram illustrating the effect of oxidation on DOX complex formation by Cys2 SP1. Doxorubicin (DOX) was reacted with Cys2 SP1 and wild type SP1 as described in FIGS. 9-13 above. Oxidized protein indicates exposure to excess of $H_2O_2$ prior to treatment with GSH. DOX complex formation was measured by ultrafiltration and size exclusion HPLC analysis (detection at 228 and 475 nm). Right hand panel shows the detection of bound and free DOX on RP-HPLC, measured at 477 nm. 1=the retentate; 2=the flow through; and 3=a DOX standard 20 μg/ml.

FIG. 15 is a photograph of a SDS PAGE fluorescence analysis characterizing the SP1-DOX complex. DOX was complexed with Cys2 SP1 variant under standard conditions (see FIG. 11), and separated by SDS-PAGE, fixed, washed, and the DOX visualized by scanning with a fluorescence imager (FUJIFILM FLA-500, FUJI, Japan), at 473 nm using the green filter. Coomassie staining was used to compare protein content of samples. Note that DOX remained tightly complexed with all forms (complex, dimer and monomer) of the Cys 2 SP1 variant even under extreme conditions (SDS-PAGE gel);

FIG. 16 is a photograph of a fluorescent PAGE analysis illustrating the stability of the DOX-SP1 complex upon exposure to heat, reduction and serum. SP1 and DOX were reacted to form complexes as described in FIGS. 9-14 above. Samples received either heat treatment (30 minutes at 85° C.) (lanes 1-4), protease treatment (Alcalase diluted 1:000, 30 min at 45° C.) (lanes 1-3 and 5), with or without diluted mouse serum (1:10) (lanes 1 and 2). For SDS-PAGE analysis, all samples were boiled for 10 minutes in buffer (LSB) with 2% beta-mercaptoethanol. Note the superior resistance of the SP1-DOX complex to denaturing and proteolytic conditions.

FIG. 17 is a photograph of a fluorescent PAGE analysis illustrating effective complex formation with DOX by Cys2 and SP1 fusion proteins. Recombinant wild type (lanes 1 and 2), Cys2 (lanes 3 and 4), and SP1 fusion proteins having additional N-terminal tumor specific peptide RGD (CRGD, SEQ ID NO:151; fusion protein is SEQ ID NO: 5)(lanes 5 and 6), or RGD in reverse order (RGDC, SEQ ID NO: 152; fusion protein is SEQ ID NO: 6)(lanes 7 and 8) were reacted with DOX to form complex as described in FIGS. 9-14 above, and then separated on SDS-PAGE with (lanes 2, 4, 6 and 8) or without (lanes 1, 3, 5 and 7) denaturation by boiling in LSB. Note the strong fluorescence in the high molecular weight complexes (unboiled samples, lanes 1, 3, 5 and 7), indicating effective binding of the drug by all variant SP1 and to much lower extent by wild type;

FIG. 18 is photograph showing the resistance of SP1 high molecular weight oligomeric complex to organic solvents. Wild type SP1 (lanes 1-3) or Cys2 SP1 (lanes 4-6) (1 mg/ml in 10 mM sodium phosphate pH 7) were lyophilized and re-suspended in buffer (lanes 1 and 4) or solvent (10 minutes incubation time) (lanes 2 and 5=methanol; lanes 3 and 6=hexane). Samples were resuspended in water and analyzed for the presence of high molecular weight oligomeric complexes by SDS-PAGE. Note the persistence of oligomeric complexes under all conditions, and that the Cys2 SP1 variant is even more resistant than the wild type;

FIG. 19 is an HPLC analysis showing the soulblization of Paclitaxel (PTX) by complex with SP1. Purified recombinant, freeze-dried wild type-SP1 was mixed with Paclitaxel solution (0.1 ml, dissolved in acetone:hexane (1:2) 0.25 mg/ml), sonicated for 20 minutes, and solvents evaporated by speed vacuum. Following dissolving in water, additional sonication and vortex mixing, 50 μl samples were analyzed by RP HPLC. Top panel shows the HPLC peaks (at 225 nm) (SP1=black; SP1-PTX=red; PTX=blue; PTX in $H_2O$=magenta). Lower panel shows the results of ultrafiltration (at 30 kD) of the complexed SP1-PXT. Note the high percentage of PTX retained in solution by the SP1-PXT complex;

FIG. 20 is an HPLC analysis showing efficient ethanol extraction of PTX from the SP1-PTX complex. SP1-PTX complex prepared as in FIG. 19 above was precipitated (red line) and then extracted (yellow line) with 80% ethanol (2 hours at −20° C.), and then analyzed on HPLC (lower panel) (blue=untreated complex). Note the loss of PTX with protein precipitation, and the appearance of PTX in the extracted sample;

FIG. 21 is an HPLC analysis showing the effect of reducing conditions on PTX extraction. SP1-PTX complex prepared as in FIG. 19 above was extracted with 0-60% ethanol (under conditions not causing protein precipitation) in the presence (closed square-magenta) or absence (closed triangle-blue) of 10 mM GSH, and then analyzed on HPLC. Note the superior retention of PTX by the oxidized complex;

FIG. 22 is an HPLC analysis showing the effects of reducing conditions on PTX binding by SP1. SP1-PTX complex was prepared as in FIG. 19 in the absence or presence of reducing conditions (b-mercaptoethanol mM), separated by ultrafiltration (sterile 0.22 μm filter) and HPLC as described above. Note the superior water solubility of the complexes formed under reducing conditions;

FIG. 23 is a graph showing the complex formation of the drug Vinblastine to SP1. Left panel-emission spectra (excitation wavelength=286.00 nm) of pure SP1 (48 μM in MES) was determined using a fluorometer. Both native (left curves) and unfolded (6M Guanidinum HCl) (right curves) SP1 were tested. The net effect of Vinblastine on Tryptophan fluorescence of native protein was calculated by subtracting the relative quenching by the unfolded protein from those of the native protein at the respective maximal emission wavelength (340 nm and 321 nm respectively). Note that the tryptophan fluorescence of both the folded and unfolded SP1 protein is quenched by Vinblastine complexing, but in the case of the folded protein is also accompanied by a red shift);

FIGS. 24a and 24b are graphs illustrating the in-vitro cytotoxic effects of SP1-DOX complex. FIG. 24a—HT-29 cells cultured in 96 well microtiter plates were exposed to uncomplexed DOX (closed oval, magenta) or SP1-DOX complex (closed triangle, blue) prepared as described in FIGS. 9-15, at the indicated concentrations. FIG. 24b—HT-29 cells were exposed to uncomplexed SP1 (without DOX) (closed diamond, blue) or SP1-DOX complex (closed triangle, yellow) at indicated concentrations. Proportion of living cells was determined by MTT assay, and the $IC_{50}$ was calculated. Note the absence of cytotoxicity of uncomplexed SP-1 (FIG. 24b), and the equivalent $IC_{50}$ values for free DOX and for the SP1-complexed DOC;

FIGS. 25a and 25b are graphs showing the in-vitro cytotoxicity of SP1-PTX complex compared to free PTX. SP1-PTX complex was prepared according to FIGS. 19-22 above. HT-29 cells were prepared as in FIG. 24 above. FIG. 24a shows the $IC_{50}$ of HT-29 cells exposed to SP1-PTX and free PTX (in DMSO). The cells were exposed to free PTX (closed circles, green) or SP1-PTX complex (closed triangle, red), at the indicated concentrations. FIG. 24b shows the $IC_{50}$ of HT-29 cells exposed to uncomplexed SP1 (close triangle, blue) or SP1-PTX complex (closed triangle, red) at indicated concentrations. Note the absence of cytotoxicity of the uncomplexed SP1, and the similar $IC_{50}$ values for both free PTX and SP1-PTX complex.

FIG. 26 is an immunoblot analysis illustrating the superior pharmacodynamics and targeting of SP1 complex. C57Bl male mice bearing the B16-F10 (B16) melanoma tumor were divided into three groups: Group A—injected once (iv with fluoresceinamine-SP1 conjugate (10 mg/ml, 0.1 ml per mouse), n=5 mice;

Group B—injected once with unconjugated fluoresceinamine solution (34 mM in PBS, 0.1 ml per animal); n=5 mice; and Group C received no treatment. n=2 mice. Internal organs were harvested 24 hours post injection, and stored at 70° C. Blood was collected and left at room temperature to coagulate. Tumor extracts and serum samples were analyzed on SDS PAGE, and proteins were blotted onto nitrocellulose. Immunodetection of SP1 was with rabbit anti SP1 and HRP-conjugated second antibody. Note the abundance of SP1 in both tumors and serum at 24 hours post injection;

FIGS. 27a and 27b are histograms showing the superior anti-tumor effects of SP1 complexed DOX compared to uncomplexed DOX. CD1 nude mice bearing human LS147T colon cancer (one million cells per animal) subcutaneous xenografted tumors were divided into two groups (n=6), and received either SP1-Dox (50 mg/Kg in PBS, about 0.5 mg DOX equivalent/Kg) or PBS (FIG. 27a), or uncomplexed DOX (3 mg/Kg) or PBS (FIG. 27b) alone injected intravenously into the tail vein twice per week for four weeks. Tumors were removed and weighed 35 days post engraftment. Note the significantly greater anti-tumor effectiveness of the complexed SP1-DOX, as compared to free DOX;

FIGS. 28a and 28b are histograms showing the significant reduction in side effects with SP1-complexed DOX treatment, compared to free DOX. CD1 nude mice bearing s.c. xenografted human LS147T colon cancer tumors were treated with intravenous SP1-complexed DOC (FIG. 28a) or free, uncomplexed DOC (FIG. 28b) as described in FIGS. 27a and 27b hereinabove. PBS was injected to the controls. Animals were weighed before sacrifice (35 days post tumor injection). Note the severe weight loss with uncomplexed, free DOX, compared to the negligible weight loss in mice receiving SP1-complexed DOX;

FIG. 29 is a graph showing the detection of SP1-DOX complex by size-exclusion HPLC analysis. SP1-DOX complex is detectable at both 278 nm (characteristic for SP1) and 475 nm (characteristic for DOX).

FIG. 30 shows a typical SP1 standard curve on size exclusion chromatography (size exclusion HPLC) at 278 nm. SP1 is eluted from the column (TSK G3000 SWXL, Tosohaas) after 7 min and is detected at 278 nm only. Inset shows the quantitative detection of the SP1 over a range of concentrations.

FIG. 31 shows chromatograms of size exclusion chromatography (size exclusion HPLC) of FA standard profile at 490 nm. In contrast with free FA, which is eluted from the column in a distinctive peak, DOX is not eluted in a distinctive peak (FIG. 29). Inset shows the quantitative detection of the FA over a range of concentrations.

DESCRIPTION OF THE PREFERRED EMBODIMENTS

Figure 3:
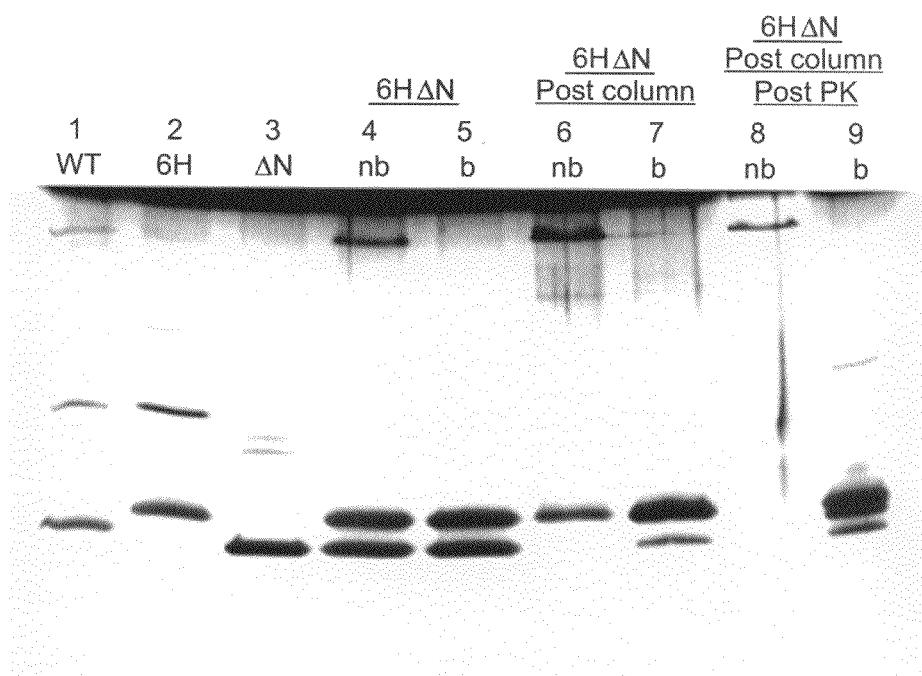

The present invention is of SP1 and SP1 variant polypeptides and polynucleotides encoding same capable of forming molecular complexes, which can be used for nanoparticles and selective complexing and release of substances.

Specifically, the present invention can be used to deliver, stabilize and solubilize therapeutic, diagnostic, cosmetic, conductive and semi-conductive agents and the like. The homo- and hetero-oligomeric complex formation characteristic of SP1 and SP1 variant polypeptides of the present invention can also be used to provide engineered self-assembling nanoparticles and nanostructures. Further, SP1 variants having a wide variety of complex-forming modifications (such as disulfide and other peptide linkages, carbohydrate, nucleic acids, etc, and combinations thereof) can be designed, producing large and varied possibilities for controlled complex and dissociation of hetero- and homo oligomeric SP1 structures, and of SP1 polypeptides complex formation with, and release of small molecules, drugs, agents, nanoparticles and the like. Additional aspects and applications of the invention are further discussed below.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

SP1 polypeptide is an exceptionally stable polypeptide, forming hetero- and homo-oligomers which are resistant to denaturation by heat and most chemical denaturants, resistant to protease digestion, and capable of stabilizing molecular interactions and forming three dimensional structures (Dgany et al, JBC, 2004; 279:51516-23, and U.S. patent application Ser. No. 10/233,409 to Wang et al)

The present inventors have previously uncovered SP1 proteins fused to other protein or non-protein molecules, for enhancement of binding properties of binding molecules, for stabilization of the fused molecules (such as enzymes) and for enhancement or alteration of immunological properties of the fused molecules (U.S. patent application Ser. No. 10/233,409 to Wang et al.). SP1 fusion proteins, as disclosed in U.S. patent application Ser. No. 10/233,409, comprise recombinant SP1 molecules having additional polypeptide sequences added by genetic engineering techniques, and SP1 molecules having additional non-protein moieties added by chemical means, such as cross linking. The present inventors have further disclosed the therapeutic use of SP1 proteins for strengthening skin, hair, nails, etc.

However, Wang et al. do not teach, nor imply native SP1, or SP1 variant polypeptides capable of controlled release of agents (therapeutic, cosmetic, diagnostic, conductive, etc) in molecular association therewith, the use thereof as carriers or the use of self-assembling SP1 monomers for the production of nanostructures.

While reducing the present invention to practice, novel SP1 variants were produced through laborious experimentation and drug design which are capable of hetero- and homo-oligomer formation, and formation of reversible molecular complexes with a variety of substances and molecules. The controllable nature of the SP1 molecular complexes of the present invention makes the SP1 polypeptides exceptionally useful as carriers for drugs, cosmetics, conductors and other small molecules. Further, specific moieties can be incorporated to add target recognition capabilities to the SP1 polypeptide, enhancing the specificity and efficacy SP1 as a drug carrier. Further, while reducing the present invention to practice, it was surprisingly uncovered that native SP1 and modified SP1 variants can self assemble to produce defined nanostructures, in a controlled and predetermined manner. Such nanostructures can be used for engineering, electrical and other nano-technological applications.

Thus, according to one aspect of the present invention there is provided an isolated polypeptide comprising an amino acid sequence of an SP1 polypeptide, the amino acid sequence being modified to be in a reversible molecular association with a substance.

As used herein the phrase "molecular association" refers to a chemical association or a physical association or both, which takes place on a molecular level. For example, an association can be a covalent bond, a non-covalent bond, a hydrophobic interaction, etc.

A "reversible association," as defined herein, is an association wherein the components can return to an original, pre-association, state, and reassociate, depending on the specific conditions. Preferably such association and reassociation does not include the formation and cleavage of peptide bonds. For example, a reversible association of the components of a SP1-therapeutic agent complex of the invention can disassociate and thereby return to original and distinct therapeutic agent and SP1 polypeptide components.

Types of reversible molecular associations suitable for use in the present invention are associations selected from the group consisting of electrostatic bonding, hydrogen bonding, van der Waals forces, ionic interaction or donor/acceptor bonding. The reversible association can be mediated by one or more associations between the substance and the SP1 polypeptide. For example, the reversible association can include a combination of hydrogen bonding and ionic bonding between the complexing substance and the SP1 polypeptide. Additionally, or alternatively, the reversible association can be in combination with, for example, covalent or other noncovalent interactions between components, such as between a substance and an SP1 polypeptide.

As used herein the phrase "SP1 polypeptide" refers to a protein having at least one of the following characteristic properties: boiling stability, protease stability or chaperone-like activity, from aspen and other plants, and belonging to the family of SP1 and SP1-like proteins (see SEQ ID NOs:123-148).

SP1 polypeptides are characterized by at least one of the following distinctive properties: stability, chaperone-like activity and excellent resistance to denaturing factors. SP1 polypeptides also share some regions of conserved sequence homology. Members of the SP1 family are preferably boiling and detergent stable proteins at least 65% homologous to SEQ ID NO:1, the boiling and detergent stable proteins having a chaperone-like activity and being capable of forming stable dimers. Yet more preferably, SP1 polypeptides have at least one conserved amino acid sequence in at least one region corresponding to amino acids 9-11, 44-46 and/or 65-73, of SEQ ID NO:1, as determined using a Best Fit algorithm of GCG, Wisconsin Package Version 9.1, using a plurality of 10.00, a threshold of 4, average weight of 1.00, average match of 2.91 and average mismatch of minus 2.00. Most preferably, the SP1 polypeptide has conserved consensus sequences: "HAFESTFES" (65-73, SEQ ID NO:1), "VKH" (9-11, SEQ ID NO:1) and "KSF" (44-46, SEQ ID NO:1). Most preferably, "wild-type" SP1 is the stress related SP1 protein from aspen (SEQ ID NO:1), as disclosed by Wang et al (U.S. patent application Ser. No. 10/233,409, filed Sep. 4, 2002, which is a Continuation in Part of PCT IL 02/00174, filed Mar. 5, 2002, both of which are incorporated by reference as if fully set forth herein).

In a preferred embodiment, the SP1 protein is 70%, more preferably 75%, yet more preferably 80%, more preferably 85%, more preferably 90%, preferably 95%, and most preferably 100% homologous to SEQ ID NO: 1.

As used herein the phrase "denaturant-stable" refers to major (above 50%) structural oligomeric stability following a denaturation treatment in aqueous solution. A denaturation treatment can include boiling and exposure to a chemical denaturant, such as, a detergent (e.g., SDS), urea, or guanidinium-HCl.

As used herein, the phrase "boiling stable" refers to major (above 50%) structural oligomeric stability following treatment at substantially 100° C. in aqueous solution for at least 10 minutes, as determined by a size fractionation assay.

As used herein, the phrase "detergent stable" refers to major (above 50%) structural oligomeric stability of an oligomeric protein following treatment in aqueous solution containing 1/2,000 molar ratio (monomer:SDS), as determined by a size fractionation assay.

As used herein in the specification and in the claims section that follows, the phrase "protease resistant" refers to major (above 50%) stability following treatment in aqueous solution containing 50 μg per ml proteinase K for at least 60 minutes at 37° C.

As used herein, the phrase "chaperone-like activity" refers to the ability to mediate native folding and native oligomerization of proteins, to prevent the formation of incorrect protein structures, to unscramble existing incorrect protein structures and to limit stress-related damage by inhibiting incorrect interactions that could occur between partially denatured proteins or their domains.

As mentioned hereinabove, the amino acid sequence of the isolated polypeptide of the present invention is modified to render it capable of forming reversible molecular associations with other molecules. Interestingly and surprisingly polypeptides of this aspect of the present invention retain the above-mentioned activities of native SP1 polypeptide such as ability of forming oligomers that are heat-stable and denaturant- and protease-resistant (see Example 2, FIGS. 4-6 hereinbelow).

Modified SP1 polypeptides of the present invention are designed to have a novel activity of interest (e.g, reversible association with a substance, cellular recognition, etc) which is not featured in wild type SP1 while still maintaining at least one of the above SP1 activities. Assays for testing such polypeptides are described hereinabove.

As used herein, the term "modified amino acid sequence" refers to an amino acid sequence having any deviation from the amino acid sequence of a native SP1 polypeptide, as described hereinabove. Modifications of SP1 polypeptide include, but are not limited to substitution of amino acids, addition of amino acids, deletion of amino acids, addition of di-, tri-, oligo- or polypeptides to the SP1 polypeptide, transposition of one or more amino acids from one portion of the amino acid sequence to another portion of the sequence, alterations of existing amino acids, such as cross-linking or elimination of portions of the side chains, addition of linkers, truncation of the amino acid sequence, addition of non-peptide moieties such as carbohydrates, lipids, nucleic acids and the like, introduction of substances having magnetic properties, etc. Examples of specific modifications are described in detail hereinbelow.

Modified SP1 variant polypeptides can be modified to impart specific properties to the SP1 variant, thereby rendering the molecular complexing with, and release of other substances more efficient and controllable, and adaptable to specific conditions. Thus, for example, addition of thiol (S—H) groups can produce SP1 variants having redox-sensitive molecular complex formation, between SP1 and complexing substances and between SP1 monomer, dimers, trimers etc. This can be useful for designing drug carriers improving the specificity of dosing and drug regimen. Further, modification of SP1 polypeptide amino acid sequence by addition of oligo- or polypeptide sequences capable of reversibly binding inorganic molecules such as metals and other ions can be useful for forming conductive compositions and altering the magnetic properties of molecular complexes formed by SP1 polypeptides. Modifications of the SP1 amino acid sequence altering interactions between the oligomer subunits, such as the dimer-dimer or monomer-monomer interactions, can serve to stabilize, or destabilize oligomer conformation, rendering the SP1 variants potentially more or less resistant to the chemical environment. Such increased, or decreased stability can be designed to affect the properties of modified SP1 variants as a carrier, for example, as a drug carrier. Such modifications in the subunit-subunit interactions of the SP1 variant can also be used to design and control the properties of SP1-based nanostructures.

It will be appreciated that the SP1-complex formation can also be based on intermolecular crosslinking mechanisms to bridge between two neighboring subunits. Examples include thiol-, amine, carboxyl and hydroxyl reactive crosslinking reagents. In such cases the controlled release mechanism can also be based on cleavage of the crosslinking by enzymatic activity as well as by using cleavable crosslinkers.

As mentioned above, the SP1 amino acid sequence can be modified to include additional peptide moieties. Thus, alternatively and additionally, the SP1 polypeptide can be modified to include at least one recognition sequence. Such recognition sequences include, but are not limited to target recognition sequences such as cell surface recognition sequences, specific ligands such as receptor binding ligands, antibodies or portions thereof such as antibody binding sites, organ- and tissue-specific recognition sequences, developmental stage-specific recognition sequences, species- and sex-specific recognition sequences, and recognition sequences correlating with specific diseases or conditions. A non-limiting list of suitable recognition sequences includes tumor surface specific peptides KNGPWYAYTGRO (SEQ ID NO: 31), NWAVWXKR (SEQ ID NO: 32), YXXEDLRRR (SEQ ID NO: 33), XXPVDHGL (SEQ ID NO: 34), LVRSTGQFV (SEQ ID NO: 35), LVSPSGSWT (SEQ ID NO: 36), ALRPSGEWL (SEQ ID NO: 37), AIMASGQWL (SEQ ID NO: 38), QILASGRWL (SEQ ID NO: 39), RRPSHAMAR (SEQ ID NO: 40), DNNRPANSM (SEQ ID NO: 41), LQDRLRFAT (SEQ ID NO: 42), PLSGDKSST (SEQ ID NO: 43), FDDARL (SEQ ID NO: 44), FSDARL (SEQ ID NO: 45), FSDMRL (SEQ ID NO: 46), FVDVRL (SEQ ID NO: 47), FTDIRL (SEQ ID NO: 48), FNDYRL (SEQ ID NO: 49), FSDTRL (SEQ ID NO: 50), PIHYIF (SEQ ID NO: 51), YIHYIF (SEQ ID NO: 52), RIHYIF (SEQ ID NO: 53), IELLQAR (SEQ ID NO: 54), CVFXXXYXXC (SEQ ID NO: 55), CXFXXXYXYLMC (SEQ ID NO: 56), CVXYCXXXXCYVC (SEQ ID NO: 57), CVXYCXXXXCWXC (SEQ ID NO: 58), DPRATPGS (SEQ ID NO: 59), HLQLQPWYPQIS (SEQ ID NO: 60), VPWMEPAYQRFL (SEQ ID NO: 61), TSPLNIHNGQKL (SEQ ID NO: 62). Suitable tumor vascular peptides for use with the modified SP1 polypeptide of the present invention include, but are not limited to CDCRGDCFC (RGD-4C) (SEQ ID NO: 63), ACDCRGDCFCG (SEQ ID NO: 64), CNGRCVSGCAGRC (SEQ ID NO: 65), CVCNGRMEC (SEQ ID NO: 66), NGRAHA (SEQ ID NO: 67), TAASGVRSMH (SEQ ID NO: 68), LTLRWVGLMS (SEQ ID NO: 69), CGSLVRC (SEQ ID NO: 70), CGLSDSC (SEQ ID NO: 71), NRSLKRISNKRIRRK (SEQ ID NO: 72), LRIKRKRRKRKKTRK (SEQ ID NO: 73), NRSTHI (SEQ ID NO: 74), SMSIARL (SEQ ID NO: 73), VSFLEYR (SEQ ID NO: 76), CPGPEGAGC (SEQ ID NO: 77), ATWLPPR (SEQ ID NO: 78), RRKRRR (SEQ ID NO: 79), ASSSYPLIHWRPWAR (SEQ ID NO: 80), CTTHWGFTLC (SEQ ID NO: 81).

As mentioned hereinabove, the SP1 polypeptide of the invention can be modified to form a reversible molecular association with a substance. Substances suitable for forming a reversible complex with the polypeptide of the present invention include, but are not limited to, a therapeutic, diagnostic or cosmetic agent. Suitable therapeutic, diagnostic or cosmetic agents include, but are not limited to a polypeptide agent, a nucleic acid agent, a lipid agent, a carbohydrate agent, and a small molecule.

Therapeutic agents suitable for use with the polypeptide of the present invention include, but are not limited to drugs and biologically active molecules such as anti-inflammatory drugs and anti-cancer (oncology) drugs). Anti inflammatory drugs that can be complexed in molecular association with SP1 of the present invention include but are not limited to Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Dndrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Momiflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

Anti-cancer drugs suitable for complexing and use with the polypeptide of the present invention include, but are not limited to Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Fluorocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, Mcgraw-Hill, Inc. (Health Professions Division).

Diagnostic substances that can be used with the SP1 polypeptides of the present invention include, but are not limited to radioactive substances, light emitting substances, radio-frequency transmitters and receivers, magnetic substances, pigmented substances, chemically active substances such as oxidizing, reducing, cross-linking, etc agents, FRET-pairs, QUANTUM dots, biochemical substances capable of molecular recognition such as nucleic acids, antibodies, etc, biologically active species such as enzymes, and the like.

According to another aspect of the present invention, the substance is a conductive or semi conductive agent. As used herein, a "conductive agent" refers to an agent capable of moving an electrically charged particle through a transmission medium. Examples of conductive agents include metals and many ionic substances. As used herein, a "semiconductive agent" refers to an agent having insulating properties, which can also, under given conditions, move an electrically charged particle through a transmission medium. Semiconductive agents behave as an insulator at very low temperatures, and have an appreciable electrical conductivity at room temperature although much lower conductivity than a conductor. Commonly used semiconducting materials are silicon, germanium, gallium arsenide, indium phosphide, and mercury cadmium telluride.

Modifications shown suitable for complex formation with conductive agents such as metal and other inorganic ionic substances include the 6H his tag for complex formation with Nickel and other metal ions (SEQ ID NO:122). Table 1 hereinbelow is a non-limiting list of additional peptides forming complexes with inorganic ionic substances that are suitable for modification of the SP1 polypeptide (adapted from Sarikaya et al., Ann Rev Mater Res 2004; 34:373-408).

TABLE 1

A list of inorganic-binding polypeptides selected by phage display (PD) and cell surface display (CSD)

| Metals and metal oxides | Sequence origin and reference | Sequences | SEQ ID |
|---|---|---|---|
| Au | CSD outer membrane | MHGKTQATSGTIQS<br>SKTSLGCQKPLYMGREMRML<br>QATSEKLVRGMEGASLHPAKT | 82<br>83<br>84 |
| Pt | PD: constrained 7aa (S. Dincer, C. Tamerler & M. Sarikaya, unpublished) | DRTSTWR<br>QSVTSTK<br>SSSHLNK | 85<br>86<br>87 |
| Pd | PD: constrained 7aa (S. Dincer, C. Tamerler & M. Sarikaya, unpublished) | SVTQNKY<br>SPHPGPY<br>HAPTPML | 88<br>89<br>90 |
| Ag | PD: 12 aa unconstrained | AYSSGAPPMPPF<br>NPSSLFRYLPSD<br>SLATQPPRTPPV | 91<br>92<br>93 |
| $SiO_2$ | PD:12 aa unconstrained | MSPHPHPRHHHT<br>RGRRRRLSCRLL<br>KPSHHHHHTGAN | 94<br>95<br>96 |
| | PD:12 aa unconstrained (D. Sahin, C. Tamerler & M. Sarikaya, unpublished) | YSDQPTQSSQRP<br>TYHSSQLQRPPL<br>SPLSIAASSPWP | 97<br>98<br>99 |
| | Silaffins | SSKKSGSYSGYSTKKSGSRRIL<br>SSKKSGSYSGSKGSKRRIL<br>SSKKSGSYSGSKGSKRRNL | 100<br>101<br>102 |
| | Silicatein α | SSRCSSSS<br>VRTRDDARTHRK | 103<br>104 |
| ZnO | CSD: flagella) | | |
| | CSD: fimbria) | PASRVEKNGVRR<br>NTRMTARQHRSANHKSTQRA<br>YDSRSMRPH | 105<br>106<br>107 |
| $Cu_2O$ | CSD: flagella) | RHTDGLRRIAAR<br>RTRRQGGDVSRD<br>RPRRSAARGSEG | 108<br>109<br>110 |
| Zeolites | CSD: outer membrane) | VKTQATSREEPPRLPSKHRPG<br>MDHGKYRQKQATPG | 111<br>112 |
| $CaCO_3$ | PD: 12 aa unconstrained) | HTQNMRMYEPWFG<br>DVFSSFNLKHMRG | 113<br>114 |
| $Cr_2O_3$ | CSD: fimbria) | VVRPKAATN<br>RIRHRLVGQ | 115<br>116 |
| $Fe_2O_3$ | CSD: outer membrane) | RRTVKHHVN | 117 |
| GaAs | PD: 12 aa unconstrained) | AQNPSDNNTHT<br>RLELAIPLQGSG<br>TPPRPIQYNHTS | 118<br>119<br>120 |
| ZnS | PD: 7aa constrained) | NNPMHQN | 121 |

Thus for example, the modified SP1 polypeptide of the present invention may be in reversible molecular association with a variety of therapeutic, cosmetic, diagnostic, conductive, etc substances.

As mentioned hereinabove, modified SP1 variant polypeptides can be modified to impart specific properties to the SP1 variant, thereby rendering the molecular complexing with, and release of other substances more efficient and controllable, and adaptable to specific conditions. It will be appreciated, that through intensive investigation into the properties of the SP1 polypeptide and oligomer complex, certain sequences of the SP1 polypeptide have been associated with one or more of the properties characteristic of the SP1 family (see, for example, Dgany et al, JBC 2004 279:51516-523). Thus, modifications within specific regions of the SP1 polypeptide can be introduced, which can in turn result in desired alterations in the properties of the SP1 variants, such as modes of molecular association, oligomer formation, etc. Dgany et al (JBC 2004 279:51516-523) have identified a number of structurally significant regions in the SP1 polypeptide:

The SP1 monomer protein chain has an α- and β-folding with three α-helices, H1 (residues 23-39), H2a (residues 74-81), and H2b (residues 84-93), and a β-sheet formed by four antiparallel β-strands, B3 (residues 9-17), B1 (residues 45-50), B2 (residues 65-71), and B4 (residues 97-108). The N-terminal segment points toward the solvent and is mobile. A long, largely unstructured loop is formed by residues 51-64, which may be involved in dimer contacts. Helices H1 and H2 define an external convex surface forming a central cavity with the opposing β-sheet. Hence, for example, modifications within the long loop may effect the stability (enhance or decrease) of dimer-dimer contacts, and oligomer formation, resulting in, for example, an SP1 variant drug carrier having a longer or shortened half-life after administration.

The dimer appears to be the smallest stable SP1 unit. The two molecules in the dimer are related by a 2-fold axis parallel to helix H1 and β-strands B3 and B4. The outer surface of the β-sheets of the two molecules forms a β barrel-like structure, defining a central pore. Modifications of this region of the SP1-polypeptide may affect the internal hydrophobic molecular environment, in turn either enhancing or decreasing the ability to complex with hydrophobic molecules.

In the oligomeric dodecamer, the interdimer contacts predominantly involve hydrophilic side chains and charged groups or are mediated by water molecules. These contacts take place mainly along the B1, H1, and the N-terminal tails. Table 2 shows a non-limiting list of novel SP1 variants produced having a modified amino acid sequence, including modifications in specific regions of the SP1 polypeptide described by Dgany et al. (JBC 2004 279:51516-523).

TABLE 2

Characterization of SP1 mutant proteins

| Location based on SP1 crystal structure | Modification[1] | Complex Formation[3] | Protease Resistance[4] | Resistance to 2M GHCl[5] | Heat stability[6] | Tm[7] | β-ME dependent Dimer formation[8] | SEQ ID NO: |
|---|---|---|---|---|---|---|---|---|
| | wild type | + | + | + | + | 107 | − | 1 |
| N-terminus modification | Δ2-6 | + | + | + | + | 104 | − | 2 |
| | Cys2 | + | + | ND | + | ND | + | 3 |
| | HH2 | + | + | ND | + | ND | − | 4 |
| | CRGD2 | + | + | ND | + | ND | + | 5 |
| | RGDC2 | + | + | ND | + | ND | + | 6 |
| | 6H2 | + | + | + | + | 109 | − | 7 |
| | Δ2-6 His2 | + | + | ND | + | ND | − | 8 |
| | Δ2-7 Cys2 | + | + | ND | + | ND | + | 9 |
| Loop1 modification (residues 18-22) | E20K | 9 | NA | NA | NA | NA | NA | 10 |
| | Cys2 K18R Gly19[2] | 10+ | + | ND | + | ND | + | 11 |
| Dimer-dimer interaction region modification | R23A | + | + | + | + | 108 | − | 12 |
| | D27A | + | + | + | + | N.D | − | 13 |
| | I30A | + | + | + | − | 98 | − | 14 |
| | N31A | + | + | + | + | 110 | − | 15 |
| | T34A | + | + | + | + | 114 | − | 16 |
| | D38A | + | + | + | + | 113 | − | 17 |
| Loop 2 modification (residues 40-44) | Δ2-6 I40C | + | + | + | + | ND | − | 18 |
| Monomer-monomer region interactions | E68A | + | + | + | + | 105.8 | − | 19 |
| Loop 4 modification (residues 72-73) | Δ2-6 E72C | 10 | + | + | + | ND | − | 20 |
| | Δ2-6 S73C | 11 | + | + | + | ND | − | 21 |
| The external perimeters of the dodecamerring | Δ2-6 L81C | 10+ | + | + | + | ND | − | 22 |
| Destabilization of Dimmer-dimer interactions | F106A 6XH2 | + | + | − | − | 75 | − | 23 |
| | Y108A | + | + | − | − | 68 | − | 24 |
| | N31A Y108A 6XH2 | ? 9 | NA | NA | NA | NA | NA | 25 |
| | T50A I52A 6XH2 | 9 | NA | NA | NA | NA | NA | 26 |
| | F106A | | NA | NA | NA | NA | NA | 27 |

TABLE 2-continued

Characterization of SP1 mutant proteins

| Location based on SP1 crystal structure | Modification[1] | Complex Formation[3] | Protease Resistance[4] | Resistance to 2M GHCl[5] | Heat stability[6] | Tm[7] | β-ME dependent Dimer formation[8] | SEQ ID NO: |
|---|---|---|---|---|---|---|---|---|
| | Y108A 6XH2 | 9 | | | | | | |
| | S73A S75A 6XH2 | + | + | + | + | NA | – | 28 |
| | D38A S75A 6XH2 | + | + | + | + | 112 | – | 29 |
| | N31A T34A 6XH2 | + | + | + | – | 96.6 | – | 30 |

ND not determined;
NA not applicable
[1]Standard nomenclature for mutation (amino acid position using wild type sequence including first Methionine residue).
[2]Insertion of Cys residue in position 2 and of glycine residue in position 19 K18R (Cys2loop1RGd).
[3]Tested by SDS PAGE when samples are not boiled in the application buffer Several SP1 mutants fail to form a soluble protein during expression and form inclusion bodies (IB). These IBs were unfolded with 0.5 M Urea, and refolded by dialysis.
[4]Tested by SDS PAGE after either proteinase K (50 ug/ml; 30 min; ° C.), or alkalase (1/1000 dilution 60 min; 45° C.) treatment, conditions under which SP1 monomer as well as most other proteins degrade.
[5]Complex stability following incubation 2M GHCl (1 h at room temp) was tested by SDS PAGE.
[6]Heat stable protein is defined as one that does not precipitate after heat treatment 10 min incubation at 100° C. or 30 min incubation at 85° C.
[7]Protein melting point was tested by DSC.
[8]Dimer formation is tested by SDS PAGE when samples are boiled for 10 min in the application buffer, in the absence or presence of b-mercaptoethanol.
[9]Inclusion Body (IB) refolding was not tested.
[10]Forms complex after IB refolding. Complex assembly was confirmed by eliminating the monomeric forms using proteinase digestion.

As shown in Table 2, for example, modifications including addition of amino acids having thiol groups characteristically have redox-dependent (β-ME) dimer formation and modifications in the amino acid sequence of the N-terminus portion of the polypeptide typically retain the ability to form oligomeric complexes, resistance to protease digestion, heat stability and resistance to guanidinium HCl denaturation.

Examples of modified SP1 variants such as SP1 6H (SEQ ID NO: 7), SP1 ΔN (SEQ ID NO:2), Cys2 SP1 (SEQ ID NO:3), CRGD SP1 (SEQ ID NO:5) and RGDC SP1 (SEQ ID NO:6) formed homo- and hetero-oligomeric complexes which showed characteristic stability and resistance.

Thus, while reducing the present invention to practice, it was uncovered that while some modified SP1 variants form boiling and protease stable complexes, others destabilize the oligomeric complexes. N-terminal truncated (ΔN) (SEQ ID NO:2) and 6H histidine tagged (SEQ ID NO:7) SP1 variants retained stable oligomeric complex formation (FIG. 3, Example 2). On the other hand, other substitutions led to the destabilizing of the complex formation, and decreased solubility (see FIG. 5, Example 3) of the recombinant protein.

Further, the modified SP1 variants retained the capability to form oligomeric, high molecular weight complexes. 6H tagged (SEQ ID NO:7) and N-terminal truncated (SEQ ID NO: 2), when dissociated into monomers by extreme conditions, regained oligomer form in both homo-oligomeric (ΔN-ΔN; and 6H 6H) and hetero-oligomeric conformations (ΔN 6H) (FIG. 5, Example 3).

Modification of the SP polypeptide amino acid sequence can be introduced by chemical, recombinant or other means. In one embodiment, modification of the amino acid sequence of SP1 is a chemical modification, such as carbodiimide conjugation, glutaraldehyde conjugation, SPDP conjugation, acylation, glycosylation, alteration of functional groups, cross-linking of amino acids, deletions and the like. The amino acid sequence can be modified by addition, usually covalent, of non-peptide molecules such as lipids, nucleic acids and carbohydrates. Other examples of peptide modification are described herein in detail.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2-NH, CH2-S, CH2-S═O, O═C—NH, CH2-O, CH2-CH2, S═C—NH, CH═CH or CF═CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

The SP1 polypeptides contemplated herein include, but are not limited to, modifications to side chains, incorporation of unnatural amino acids and/or their derivatives during peptide synthesis and the use of crosslinkers and other methods which impose conformational constraints on the peptides or their analogues.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5'-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH═CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1-2 below list all the naturally occurring amino acids (Table 3) and non-conventional or modified amino acids (Table 4).

TABLE 3

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Iie | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 4

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisoleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Due | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |

TABLE 4-continued

| Non-conventional amino acid | Code | Non-conventional amino acid | Code |
|---|---|---|---|
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododecleglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methyl-cyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylamino-isobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methylanapthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methyl-cyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methyl-aminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methyl-homophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methyltryptophan | Mtrp | L-α-methyltyrosine | Mtyr |
| L-α-methylvaline | Mval | L-N-methyl-homophenylalanine | Nmhphe |
| L-α-methylleucine | Nnbhm | | |
| N-(N-(2,2-diphenylethyl)carbamylmethyl-glycine | Nnbhm | N-(N-(3,3-diphenylpropyl)carbamylmethyl(1)-glycine | Nnbhe |
| 1-carboxy-1-(2,2-diphenyl ethylamino)-cyclopropane | Nmbc | | |

The peptides of the present invention may be utilized in a linear form, although it will be appreciated that in cases where cyclicization does not severely interfere with peptide characteristics, cyclic forms of the peptide can also be utilized.

The peptides of the present invention may be synthesized by any techniques that are known to those skilled in the art of peptide synthesis. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide and so forth. Further description of peptide synthesis is disclosed in U.S. Pat. No. 6,472,505.

One method of preparing the peptide compounds of the present invention involves solid phase peptide synthesis. Large scale peptide synthesis is described by Andersson Biopolymers 2000; 55(3):227-50.

Alternatively, and additionally, modifications can be introduced into the amino acid sequence of the SP1 polypeptide by genetic methods, by modifying the nucleic acid coding sequence (substitutions, deletions, insertions etc) and expressing the sequence in a transformed cell or organism, thereby producing a modified recombinant SP1 variant polypeptide. Methods of modification at the genetic level include, but are not limited to, site directed mutagenesis and random mutagenesis. Signals for post translational modification of the recombinant polypeptide, such as glycosylation, can also be introduced into the coding sequence.

Thus, according to another aspect of the present invention, there is provided an isolated polynucleotide comprising a nucleic acid sequence encoding a modified SP1 polypeptide having an amino acid sequence as set forth in any of SEQ ID NOs: 2-30). The nucleotide sequence encoding the wild-type *P. tremula* SP1 polypeptide is as set forth in SEQ ID NO: 149.

It will be appreciated that the polynucleotide of the present invention can be introduced into a vector for recombinant expression in a host organism. According to another aspect of the present invention there is provided a nucleic acid construct comprising the isolated nucleic acid described herein.

According to a preferred embodiment the nucleic acid construct according to this aspect of the present invention further comprising a promoter for regulating the expression of the polynucleotide in a sense orientation. Such promoters are known to be cis-acting sequence elements required for transcription as they serve to bind DNA dependent RNA polymerase which transcribes sequences present downstream thereof.

While the polynucleotide described herein is an essential element of the invention, it can be used in different contexts. The promoter of choice that is used in conjunction with the polynucleotide of the invention is of secondary importance, and will comprise any suitable promoter. It will be appreciated by one skilled in the art, however, that it is necessary to make sure that the transcription start site(s) will be located upstream of an open reading frame. In a preferred embodiment of the present invention, the promoter that is selected comprises an element that is active in the particular host cells of interest, be it a bacteria, yeast or a higher cell of a plant or animal.

A construct according to the present invention preferably further includes an appropriate selectable marker. In a more preferred embodiment according to the present invention the construct further includes an origin of replication. In another most preferred embodiment according to the present invention the construct is a shuttle vector, which can propagate both in *E. coli* (wherein the construct comprises an appropriate selectable marker and origin of replication) and be compatible for propagation in cells, or integration in the genome, of an organism of choice. The construct according to this aspect of the present invention can be, for example, a plasmid, a bacmid, a phagemid, a cosmid, a phage, a virus or an artificial chromosome.

The construct of the present invention can be used to express the polypeptide encoded thereby in a variety of species ranging from bacteria such as *E. coli*, yeast cells or higher cells such as the cells of a plant. Expression can be selected stable or transient.

For effecting plant transformation, the exogenous polynucleotides which encode enzymes capable of catalyzing proline production are preferably included within a nucleic acid construct or constructs which serve to facilitate the introduction of the exogenous polynucleotides into plant cells or tissues and the expression of the enzymes in the plant.

Since the polypeptides of the present invention retain their SP-1 activities (as mentioned hereinabove) they can be used in a myriad of applications such as previously described, and currently envisaged, as further described hereinbelow. It will be appreciated that where desirable, native SP-1 polypeptides may also be used in accordance with the present invention.

According to one aspect of the present invention, there is provided a method of delivering a therapeutic, diagnostic or cosmetic agent to a subject in need thereof, wherein the method comprises administering to the subject a therapeutically, cosmetically or diagnostically effective amount of a composition of matter comprising an SP1-polypeptide of the present invention in molecular association with the agent. In a preferred embodiment, the SP1 polypeptide is a modified SP1 polypeptide. In another embodiment, the molecular association with the agent is a reversible association.

As used herein, the phrase "therapeutic agent" refers to any agent, the administration of which is capable of causing an improvement in any aspect of a given condition. A therapeutic agent may be symptomatically effective, partially effective, may cure, treat, palliate, prevent the progression of, improve the prognosis for, etc any condition for which it is administered. Therapeutic agents can be effective alone, or as adjuncts to other agents. Therapeutic agents can be effective in short and/or long term, and can be broadly effective within a wide range of conditions, or narrow and specific in their effectiveness.

As used herein, the phrase "diagnostic agent" refers to any agent which is used in connection with methods for diagnosing the presence or absence of a disease or condition in a patient. Exemplary diagnostic agents include, for example, contrast agents for use in connection with ultrasound, magnetic resonance imaging or computed tomography of a patient.

As used herein, the term "cosmetic agent" refers to any agent, such as a pigment or fragrance, which may be topically applied to human skin for aesthetic effect and which preferably does not cause irritation. Cosmetic agents are well known in the art and are included in such products as lipsticks, eye shadows, rouges, foundations and other forms of "makeup", creams, pastes, lotions, balms, sprays, gels, foams, etc. that can be applied dermally or topically, such as creams, e.g., grease creams or dry creams.

As used herein, the phrase "subject in need thereof" refers to any subject which may derive benefit from the administration of the composition-of-matter of the present invention. Such a subject can be, for example, a subject having a specific condition, or at risk of having a specific condition, for which the administration of the composition of matter can have a therapeutic or beneficial effect.

The composition of matter of the present invention can be administered to an organism per se, or in a pharmaceutical composition where it is mixed with suitable carriers or excipients.

The composition-of-matter of the present invention can be a pharmaceutical composition. As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the SP1 or SP1 variant, alone or in molecular association with a substance or agent, accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (nucleic acid construct) effective to prevent, alleviate or ameliorate symptoms of a disorder (e.g., ischemia) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma or brain levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

While reducing the present invention to practice, it was uncovered that the introduction of disulfide bridges into SP1 amino acid sequence produces a variant SP1 polypeptide having unique properties. N-terminal cysteine residues (Cys 2 P1 variant, SEQ ID NO: 3) sensitizes the variant SP1 polypeptide to the redox state (FIG. 8*b*, Example 4). Thus, modified SP1 offers specific control over complexing and release (FIGS. 8, 9, 10 and 11, Example 4) of agents or substances, in this case the labeling substance FA. Indeed, release of drug molecules from SP1-drug complexes such as Cys 2 SP1-DOX, and fluorescent label from Cys 2 SP1-FA complexes was shown to be sensitive to redox state (FIGS. 9-11, 14, 16, Example 4). It will be appreciated that the previously unattainable control of complex formation can be advantageous in designing modified SP1 polypeptide drug carriers, diagnostic tools, nanostructures, etc. For example, SP1-complexes with substances such as therapeutic agents, cosmetic agents, fragrance agents, diagnostic agents, etc. can be induced to formation by exposure to reducing conditions, and at a later point, induced to release by competition for the thiol bearing residues (see schematic, FIG. 8*a*-*c*).

While reducing the present invention to practice, SP1 modified with specific tumor vasculature recognition peptides showed characteristic oligomer complex formation, heat stability and protease resistance (FIG. 4, Ex 2). Thus, SP1 can be modified to comprise a target recognition sequence or moiety, and further modified to form a reversible complex with a substance (therapeutic, diagnostic, conductive agent, etc). Thus, such a modified SP1 polypeptide can be used to target the delivery of a substance in reversible complex with SP1.

It will be appreciated that complexing of cytotoxic drug to nanoparticles such as the SP1 oligomer may also assist passive targeting to tumors. Several model tumour systems are now known to display increased vascular permeability compared with normal tissues, permitting their selective targeting using macromolecular drug carriers. Preliminary clinical observations suggest that increased vascular permeability is characteristic of some types of human cancer, and this may have important implications for the use of carriers such as SP1 in facilitating macromolecular drug treatments, including cytotoxic drugs, antibody targeting and delivery of DNA for gene therapy.

The modified SP1 polypeptides of the present invention can be used to stabilize a substance. As used herein, the term "stabilize" refers to increasing the chemical, physical or biochemical stability of a molecule, composition, compound, etc. Stability can be further defined in the context of specific properties. In a preferred embodiment, stability is temperature stability, ionic strength stability, protease stability and catalytic stability. Examples of assays for measuring such stability are described in detail hereinbelow.

While reducing the present invention to practice, it was shown that complexing of molecules with SP1 greatly enhanced solubility and stability in solution. As used herein, the term "solubility" refers to the ability of a solute to be evenly dispersed and dissolved in a solvent, in order to form a solution comprising the solvent and solute. It will be appreciated that all solutes are, in theory, soluble in all solvents. However, poorly or negligibly soluble (immiscible) solutes do not form solutions of any significant concentration with given solvents.

Thus, as used herein, "enhancing the solubility of a substance in a solution" refers to increasing the concentration of said substance, as a solute, in a solution with a solvent. In a preferred embodiment, the substance is a hydrophobic substance, typically insoluble or poorly soluble in water, and the solvent is an aqueous solvent.

The stability of unmodified, and modified SP1 polypeptide oligomeric complex to organic solvents was shown in FIG. 18 hereinbelow. When combined with hydrophobic molecules such as PTX in organic solvents, dried and reconstituted in aqueous solvent, molecular association and complex formation between the SP1 and the hydrophobic molecule rendered the PTX water soluble (FIGS. 19 and 20). Thus, SP1 can be used to enhance the solubility of a substance in a solution. In a preferred embodiment, the substance is a hydrophobic substance, and the solution is an aqueous solution. Such substances, such as hydrophobic drugs, volatile esters and other molecules, fragrance molecules, cosmetic molecules, oils, pigments, vitamins, organic molecules, etc. can be solubilized for mixing with water and aqueous solvents. Further, while reducing the present invention to practice, it was shown that the lyophilized SP-PTX complex remains stable after reconstitution (see Example 5 hereinbelow). Thus, molecular association and complex formation with SP1 and modified SP1 variants can be used for more effective storage of hydrophobic, volatile, labile, etc. molecules such as PTX.

As mentioned hereinabove, the modified SP1 polypeptides of the present invention can bear more than one modification in the amino acid sequence. Thus, for example, SP1 polypeptides modified capable of complexing with inorganic molecules (e.g. metal ions; see Table 1 hereinabove) can be further modified to form a reversible molecular association with a second substance, and used to deliver the second substance to any surface comprising the inorganic molecule. Such an association can be useful in nanotechnology and solid-state engineering applications, wherein the modified SP1 complex can be used to deposit a layer of the second substance, evenly and of a predetermined molecular thickness. Such a method of delivery of, for example, doping or insulating substances, would be particularly advantageous for use over uneven surfaces.

The modified SP1 polypeptides of the present invention can be used for controlled delivery and release of inorganic molecules in biomimetic applications. SP1 has been shown to self assemble in ordered geometric conformations (see FIG. 1 and FIG. 2), which can be altered by modification of the amino acid sequence. Further modifications to provide carrier capability (such as reversible binding of inorganic molecules) can produce SP1 molecules modified to serve as molecular carriers in biomimetic processes, such as controlled crystal formation, etc. Such modified SP1 polypeptides can be useful for accurate delivery and release of, for example, inorganic molecules, to prevent uncontrolled aggregation in nanoscale processes, and as coupling molecules having well-defined and controllable properties (see Sarikaya et al., Ann Rev Mater Res 2004; 34:373-408 for a recent review of the subject of biomemtics).

The SP1 polypeptides of the present invention can be used to make and operate nanoscale structures and devices. Polypeptides have an advantage in nanoscale technology, since binding peptides and proteins are selected and designed at the molecular level and through genetics, allowing control at the lowest dimensional scale possible. Also, such proteins can be used as linkers or "molecular erector sets" to Join synthetic entities, including nanoparticles, functional polymers, or other nanostructures on molecular templates. Further, biological molecules self- and coassemble into ordered nanostructures, ensuring a robust assembly process for the construction of complex nanostructures, and possibly hierarchical structures, similar to those found in nature.

As mentioned hereinabove, the SP1 polypeptides of the present invention can self-assemble to form regular and predictable nano-scale structures. Thus, there is provided a composition-of-matter comprising a plurality of self assembled modified SP1 monomers useful as, for example, molecular linkers and complex nanostructures.

The SP1 polypeptides of the present invention can further be used for affinity binding (through specific fused peptides or polypeptides) of ligand and ligand binding molecules, surface coating of any compounds and/or molecules capable of molecular association and complexing with SP1 oligomers, nanocircuitry through controlled association of conducting molecules or semiconductors in molecular association with SP1 oligomers, magnetic particles or nanoparticles associated with SP1 oligomers, controlled association and release of any biologically active molecules, such as herbicides, insecticides, volatile and odoriferous compounds, etc., nano-computing, lithography and printing with conductive inks, nanoarchitecture through controlled association and dissociation of three dimensional nanostructures. Yet further, the SP1 polypeptides of the present invention can be incorporate as a component of a conductive device such as an electronic device.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Experimental Methods

Expression of recombinant SP1—A 567-bp cDNA clone was isolated by screening 7_10$^5$ recombinant phage plaques from a lambda expression library derived from water-stressed aspen shoots, using anti-SP1 antibodies (Wang et al, U.S. patent application Ser. No. 10/233,409). E. coli strain BL21 (DE3) was transformed with a plasmid carrying the sp1 gene (pET29a, kanamycin resistance conferred) (Wang, et al. Plant Phys 2002; 130:865-75). Wild type SP1 as well as its variants were generated and expressed in E. coli: a full length SP1 without any additional tag, designated as SP1 (SEQ ID NO:1); a six-histidine tag was introduced to the N-terminal of SP1 to generate 6HSP1 (SEQ ID NO:7), and a cysteine residue was introduced in position 21 of SP1 to generate Cys2 SP1 (SEQ ID NO:3), and the ΔNSP1 (SEQ ID NO:2) was generated by a deletion of amino acid 2-6 at SP1 N-terminus. The expression of these recombinant SP1 proteins followed standard recombinant procedures, as described in Wang et al., (Acta Crys 2003; D59:512-14).

Protein purification—Recombinant SP1 was produced from E. coli as described in Wang et al 2003. 6HSP1 was further purified on Ni-NTA Agarose beads (P-6611, Sigma Chemicals St Louis Mich.) according to the supplier's protocol except for the fact that the elution buffer contained 400 mM imidazole. The boiling stable fraction of ΔNSP1 was dialyzed against 2×20 volumes of 15-20 mM piperazine at pH 5.9 as preparation to the anion exchange column SOURCE-15Q (Amersham Biosciences UK). Buffer A in the mobile phase was 20 mM piperazine pH 5.1 and the same buffer with 1M NaCl was used as buffer B. The ΔNSP1 was eluted by 23-25% buffer B. Ammonium sulfate at a final concentration of 1M and NaOH to a 7.5 pH were added to the purified ΔNSP1, and then loaded to a HiTrap phenyl sepharose HP column (Amersham Biosciences UK) that was prewashed with 50 mM phosphate buffer containing 1M Ammonium Sulfate at pH 7.5. The ΔNSP1 eluted at 47-48% 50 mM phosphate pH 7.5 (buffer B). The ΔNSP1 was then concentrated and diafiltered by 30 kDa cut-off ultra filtration concentrator using 25 mM phosphate pH 7.5).

Analytical ultracentrifugation—Equilibrium sedimentation studies were carried out using a Beckman Optima™ XL-1 analytical ultracentrifuge (Beckman Instruments, INC.). Aspen SP1 was dialysed overnight against 200-fold 20 mM Tris-HCl, pH 8.0. The samples were then diluted with dialysate to generate protein solutions of approximately 202, 152, 68, 22.5 and 6.5 μM. The samples were spun in a six-sector cell at rotor speeds of 6000 and 7000 rpm at 20° C. Data were collected at 280, 220 and 254 nm and were analyzed using the following equation: $M=[2RT/(1-v)\rho\omega^2][d(\ln(c))/dr^2)]$ with a typical $v=0.73$ cm$^3$ g$^{-1}$ and $\rho=0.9994$ g cm$^{-1}$.

Transmission electron microscopy (TEM) study—SP1 (0.05 mg/ml) was applied to glow-discharged, carbon and nitrocellulose-coated copper 400-mesh grids, and stained with 2% uranyl acetate. Images were taken with an FEI Tecnai-12 microscope and recorded on Kodak S0163 film or on a Megaview III digital camera (Soft Imaging Systems, Münster, Germany). Micrographs were digitized with an Imacon Flextight II scanner. Image processing for averaging of top-view wild-type SP1 particles was done with the SPIDER program suite (Frank et al., 1996) and consisted of an initial reference-free alignment (translational and rotational) followed by three rounds of reference-based alignment. Cryo-negative stained images of SP1 were prepared by placing 4 μl of SP1 (1 mg/ml) on lacey grids (SPI Supplies, West Chester Pa.), applying 16% ammonium molybdate (Adrien et al. 1998), and plunging in liquid ethane. Imaging under low dose cryo-conditions was done on an FEI Tecnai F20 microscope and recorded on a TVIPS (Gauting, Germany) 1 k×1 k Biocam camera.

Chemical cross-linking of SP1 and mass spectrometry-SP1 at 1 mg/ml was incubated at room temperature with 0.25% gluteraldehyde (GA) in 50 mM Triethanolamine buffer (pH 5.7, 72 hr). The non-cross-linked and cross-linked SP1 products were subjected to mass spectrometry analysis. Matrix-assisted laser-desorption time-of-flight mass-spectrometry (MALDI-TOF-MS) was performed on a Micromass TofSpec 2E reflectron mass-spectrometer (The Protein Research Center, Technion, Haifa, Israel).

SP1 stability following exposure to SDS and heating-SP1 (20 μg) was prepared in SDS sample buffer at different SP1-monomer:SDS molar ratios and boiled (or not) (5 min) prior to SDS-PAGE analysis. Heat stability of SP1 oligomer (10 μg) was tested in the same buffer at SP1-monomer:SDS=1: 1733 and heated for 1 to 10 min at different temperatures.

Protease susceptibility examination of SP1-SP1 (10 μg) prepared either in V8 protease digestion buffer (125 mM Tris-HCl, pH 6.8, 10% glycerol, 0.5% SDS) or standard buffer (20 mM Tris-HCl, pH 7.5, 1 mM EDTA, 50 mM NaCl), was boiled for 2 min or not boiled prior the addition of protease (Staphylococcus aureus V8 protease, trypsin, proteinase K, Sigma Chemicals Inc., Israel). Proteases were added to a final concentration of 50 μg/ml (SP1: protease equal to 1:20, w/w). The digestion was performed at 37° C. for 1 hr. The samples were then prepared in SDS sample buffer, and boiled or not before being subjected to 17% tricine-SDS-PAGE.

Purification of SP1 by boiling and proteolysis-Plant total soluble proteins or concentrated total boiling-soluble proteins were incubated with 50 μg/ml proteinase K (37° C., 1 hr). Similar procedures were applied to total recombinant bacterial proteins. PK was inactivated by boiling (10 min) followed by centrifugation (15,000×g, 10 min). SP1 was concentrated by ultrafiltration (10 kDa cut-off, VIVASCIENCE, Binbrook Lincoln, England).

Engineering disulfide bridges to SP1 complex. Cys 2SP1 gene was constructed by site directed mutagenesis of the N terminal alanine to cysteine. Both wild type and Cys 2 SP1 (SEQ ID NO:3) (2 mg/ml) were incubated in the presence or absence of 10 mM DTT overnight and preboiled with a 2% SDS sample buffer prior to SDS-PAGE analysis.

Resistance of SP1 complex to various organic solvents. 150 ul of 1 mg/ml samples in 10 mM sodium phosphate pH 7 were lyophilized overnight and resuspended in 150 µl organic solvents for 10 minutes. Following a 30 minutes speed vac the samples were resuspended in 150 µl water and analyzed by SDS-PAGE.

Reassembly of SP1 Hetero-Oligomers.

Purified 6HSP1 and ΔNSP1 were first denatured to the monomeric forms by boiling the proteins in SDS sample buffer. The denatured proteins were then separated in preparative SDS-PAGE, and visualized by Coomassie blue staining. The monomeric forms of two recombinant protein bands were excised. Gel slices that carried monomeric form of 6HSP1 (SEQ ID NO:7) and ΔNSP1 (SEQ ID NO:2) were mixed at 1:1 ratio (v/v). In order to enhance the surface/volume ratio, the gel slices were pulverized using a pestle and mortar in the presence of liquid nitrogen. Then the proteins were co-eluted by electro-elution as described previously (Wang et al., 2002). The hetero-oligomeric complex was isolated by subjecting the eluated protein to Ni-NTA Agarose beads and the bound proteins were eluted by 400 mM imidazole using a standard procedure (Sigma protocol for P 6611). Proteinase K which digests monomeric SP1 but not SP1 complex (described in this paper), was employed to eliminate the monomeric form of 6HSP1 (SEQ ID NO:7) and ΔNSP1 (SEQ ID NO:2) from the Ni-NTA purified proteins. The composition of hetero-oligomeric SP1 was determined by SDS-PAGE and visualized by silver staining.

Ultrafiltration: Ultrafiltration was used for the detection of complex formation with the water soluble ligands FA and DOX which have a distinctive absorption properties and can be determined by spectroscopic measurements. Free FA and DOX are much smaller than SP1 (0.35, and 0.58 versus 150 kDa, respectively): while the free FA and DOX pass through a molecular weight cutoff membrane of 30 kDa (flow through-fraction), both free SP1 and SP1 complexes are retained above the membrane (retained fraction). Several additional washing cycles remove all remaining free FA and DOX, and the ligand-SP1 complex remains in the retained fraction.

Size exclusion chromatography: Size exclusion chromatography is a common method for separation of molecules of different sizes under mild conditions and was employed to test FA and DOX complex formation under mild conditions. SP1 is eluted from the column after 7 min and is detected at 278 nm only, and free FA is eluted from the column (TSK G3000 SWXL, Tosohaas) after 16 min and is detected at 490 nm. The SP1-FA and SP1-DOX complexes also eluted at the same time but is detected also at 490 and 475 nm, respectively. SP1 is eluted from the column after 7 min and is detected at 278 nm only. DOX/SP1 ratio is determine from the standard curve obtained in solution.

C-18 Reversed phase HPLC: Reverse phase HPLC (RP-HPLC) analysis separates between free DOX, PXT, and SP1. Both compounds bind to the resin (C-18) and are eluted at different acetonitrile concentrations, and detected at both 278 and 225 nm (SP1), 225 nm (PTX) and 477 nm (DOX).

SP1-DOX complexes together with uncomplexed SP1 and are detected at 477 nm, as well as 278 nm. Quantification of SP1-DOX, and free DOX is directly calculated from the absorbance in their peaks at 477 nm. However to estimate the amount of protein in the SP1-DOX peak, absorption at 278 nm is corrected for DOX according to the following equation (ODP278−0.77*OD$_{477}$). In contrast with FA and DOX, complexed PTX cannot be detected, but it is detected in the same elution as free PTX.

The C18 RP HPLC separation, and detection of DOX and PTX compounds is outlined in below. Solvent A=water+0.1% TFA. Solvent B=Acetonitrile+0.1% TFA. Program was 0-5 min 75% A, 0% B; 5-15 min 25%-75% B. SP1 was detected at 225 and/or 278 nm; DOX at 477 and/or 278 nm; and PTX at 225 nm.

DOX-SP1 complex: Pyrogen free Cys2 SP1 variant (SEQ ID NO:3) in 20 mM (Na Phosphate buffer pH-6.7) final 2 mg/ml was diluted with DOX solution (Teva, Israel) 1:2 dilution final 1 mg/ml. Where indicated, GSH was added, and the solution is mixed overnight. Where indicated (oxidized), $H_2O_2$ is added to 0.1%, buffer added to 3× volume, and the solution is sonicated (3×22 sec. 1:1 pulse/pause at 3% amplitude 0.5 min. pause, using a Vibra-Cell 750 W sonicator).

Ethanol precipitation of free DOX: Solution diluted 5× (V:V) with ethanol, incubated −20° C. for 3 hours, centrifuged 30 minutes at 1250×g, room temperature. Pelleted material is washed and resuspended in cold ethanol, repelleted, resuspended and analyzed by HPLC.

Removal of unbound DOX: The SP1-DOX solution was washed by ultrafiltration 30K cut-off microcon filter (Millipor Ltd., Billerica, Mass.), then washed with Na Phosphate buffer (pH 6.7), and PBS, until flow-through is colorless.

SP1-PTX Complex: 3 mg SP1 (25 mg/ml, 120 ul in PBS) was freeze dried for 6 h in 15 ml plastic tubes. 300 ul PTX (1 mg/ml in dry aceton/hexan 1:1+0.1% betamercaptoethanol) was added, and aceton/hexan+0.1% betamercaptoethanol added to a final volume of 4 ml. The mixture was sonicated (1 sec pulse, 3 second pause, 45" sonication time, total 3 min, 35% intensity, on ice). The organic solvents were evaporated by dessication overnight, 0.4 ml PBS added, the mixture sonicated (1 sec pulse, 3 sec pause, 30" sanitation time, total 2.5 min, 35% intensity, on ice). Debris was pelleted by centrifugation (5 min, 14000 RPM). For tissue culture experiments, aliquots were filtered.

Cell growth conditions: Human colon adenocarcinoma (HT-29) cells. The cells were grown in 50-ml flasks containing DMEM medium (Biological Industries, Bet Haemek), supplemented with 10% fetal calf serum, 1% glutamine and 1% Antibiotic-Antimicotic solution (Biolab, Israel). The cells were trypsinized, and 2 ml medium containing $5 \times 10^4$ cells were plated in each well of a 6-wells plate. SP1, drugs or SP1-complexed with drugs was added at the indicated concentrations. The cells were incubated at 37° C. in a humidified atmosphere containing 5% $CO_2$. After 48 hours the medium in the presence or absence of drugs was replaced in each well respectively, to maintain a constant supply of ingredients and drugs. After four days the medium was removed and the number of viable cells in the cultures was determined by spectroscopy.

In vivo effects of SP1-DOX and SP1-PTX in B16 melanoma model; B16-F10 (B16) melanoma tumor C57B1 male mice bearing the B16-F10 (B16) melanoma tumor were prepared and cared for as described by Kalechman (Int J Cancer 2000; 86:281-8). B16F10 melanoma cells ($5 \times 10^5$ or $5 \times 10^6$ cells/mouse) were injected into the lateral tail vein of the mice and the presence of cancer tumors was evaluated at day 14 following melanoma cell injection by an overall view of the mouse and/or histopathology examinations. Mice were divided into three groups: Group A—injected once (iv with Fluoresceinamine-SP1 complex solution (SP1-FA conjugate, 10 mg/ml in PBS; 0.1 ml per animal). N=5 mice. Group B received FA once, at 1 week. N=5 mice. Group C received no injections N=2 mice. 24 h post injection internal organs were collected and stored at −70° C. Blood was collected, coagulated at room temperature, sera separated and frozen.

Organs and tumors were homogenized, and extracts and diluted (3× in PBS) sera were heat treated (85° C. for 30 minutes), and separated on SDS PAGE. For immunodetection, separated proteins were transferred from gel to nitrocellulose paper by electroblotting. Nitrocellulose blots was blocked by immersion in Tris-buffered saline+0.05% Tween 20, pH=7.7 (TBST) containing 3% skimmed milk. After washing the skimmed milk with TBST, the nitrocellulose blot was immersed in primary rabbit anti SP1-antibody in TBST. After washing primary antibody with TBST, the nitrocellulose blot was immersed in secondary Goat anti-Rabbit antibody HRP conjugate in TBST. After washing excess secondary antibody with TBST, the nitrocellulose blot was contacted with the HRP chemiluminescent substrate (ECL).

Photographic film is exposed to the wrapped nitrocellulose paper, then developed and fixed.

In vivo effects of free DOX and SP1-DOX on tumor size: Human LS147T colon cancer (one million cells per animal) were grafted sub cutaneously to CD1 nude mice, (3-4 weeks old, 18-20 g) (Meyer et al. 1995 Am J Dermatopath; 17:368-73). 8 days later a 3-10-mm tumor appeared in the point of injection. At this time the animals were divided into two groups (6 animals in each), average tumor size and animal weight were similar.

8 days after tumor grafting SP1-DOX (50 mg/Kg in PBS, about 1 mg DOX equivalent/Kg), free DOX (3 mg/Kg in PBS) or PBS alone, six mice in each group, were injected iv to the tail vein twice a week for four weeks. Tumor dimension was determined by caliper measurements by the standard equation (Kalechman et al. Int J Cancer 2000; 86:281-8). At 35 days post tumor grafting the animal were sacrificed. Tumors were removed and their weight was determined.

EXPERIMENTAL RESULTS

Example 1

Structure of the SP1 Protein

SDS gel electrophoresis analysis of both native SP1 and its recombinant form shows that SP1 appears in two forms: a monomer (12.4-kDa) which appears when the sample is boiled in the gel application buffer in the presence of SDS and in an oligometric form (116-kDa protein) which appear when SP1 is not boiled prior to application on PAGE (see Wang et al 2002, Dgany 2004, Wang et al 2006, U.S. patent application Ser. No. 10/443,209). Several methods have been employed to demonstrate that SP1 in solution forms a dodecamer with a molecular weight of 150 kDa. Equilibrium analytical ultra-centrifugation was employed to analyze the SP1 oligomeric state. As SP1 concentration approached zero, the measured molecular mass of the SP1 particles in solution (144 kDa at 5.6 µM monomer concentration) approached the value calculated for a dodecamer (148 kDa).

SP1 was subjected to MALDI-TOF-MS. The data revealed 12 protein peaks, of which the first (12338 Da) was close to the predicted molecular weight of the monomer (12369 Da). The other peaks corresponded to SP1 dimer up to a dodecamer with a molecular interval of about 12.4 kDa. MALDI-TOF-MS analysis of cross-linked SP1 revealed 12 clear peaks with molecular mass ranging from 12998 to 154706 Da, corresponding to the monomer, and up to a dodecamer. Gel filtration HPLC analysis using TSK3000 column also shows that SP1 forms a dodecamer. The oligomeric form was further estimated on an electro-eluted high-molecular mass SP1 (116 kD) appeared as a single peak at about 9.8 min. This peak, as calculated from a standard curve, corresponded to a molecular mass of 144.9±1.54 kD, which is 11.7 (about 12 units) of SP1 monomer (12.369 kD).

While reducing the present invention to practice, electron microscope study of SP1 was undertaken. Electron microscopy studies showed that SP1 is a ring-like protein with a central cavity.

In order to determine conditions under which SP1 forms two dimensional crystals, SP1 was mixed with phospholipids (DOTAP/DOPC 1:1, w/w, in Hexane Chloroform). FIG. 1 shows a TEM image of phospholipid induced two dimensional SP1 crystal monolayer, indicating the ability to form two dimensional crystals of SP1. Thus, indicating that that the particles can arrange in different ways and SP1 can self assembled into higher order structures.

SP1 monomer: X-ray crystallography studies (see Dgany et al 2004), showed that SP1 chain has α- and β-folding with three α-helices, H1 (residues 23-39), H2a (residues 74-81), and H2b (residues 84-93), and a β-sheet formed by four antiparallel β-strands, B3 (residues 9-17), B1 (residues 45-50), B2 (residues 65-71), and B4 (residues 97-108). The N-terminal segment points toward the solvent and is mobile as evidenced by the lack of interpretable electron density for the first two residues and the large temperature factors for Thr-3 and Lys-4. The long loop formed by residues 51-64 is largely unstructured. This loop projects away from the molecule and is involved in dimer contacts. Helices H1 and H2 define an external convex surface with numerous hydrophilic and acidic side chains facing toward the solvent.

The inner side of this surface and the opposing β-sheet enclose a hydrophobic central cavity rich in aromatic and hydrophobic residues. Most of the phenylalanines in the SP1 molecule occupy this cavity (Phe-17, -46, -67, -71, -89, and -93). Trp-48 and Tyr-33, Tyr-63 and Tyr-80, together with the two histidines (His-11 and His-65), and Arg-100 block access of the solvent to the cavity. Without wishing to be limited to a single hypothesis, we believe that this cavity may serve as binding site for small hydrophobic molecules.

It should be noted that SP1 structure is similar to the structure of its *Arabidopsis thaliana* analog (gene locus At3g1721050, accession no: AY064673, SEQ ID NO: 150)) as resolved by both X-ray crystallography and NMR (Bingman et al. Proteins 2004; 57:218-20; Lytle et al. J Biomol NMR; 28:397-400).

Figure 6A:
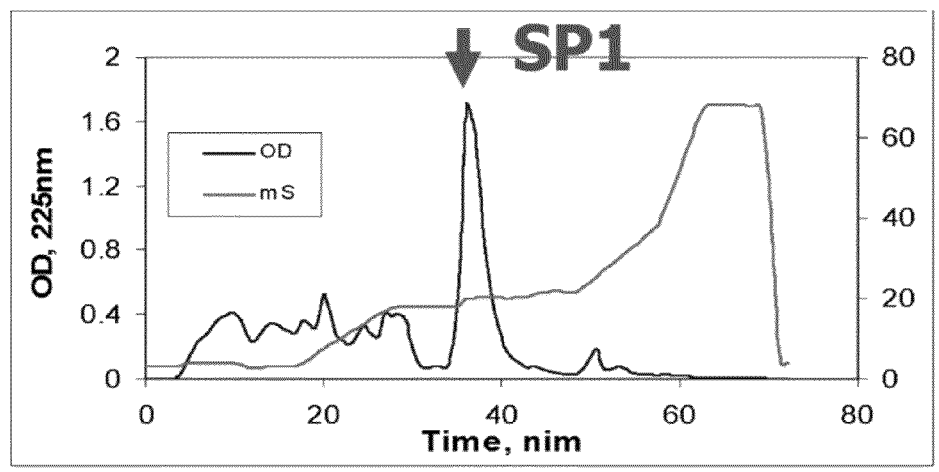
Figure 6B:
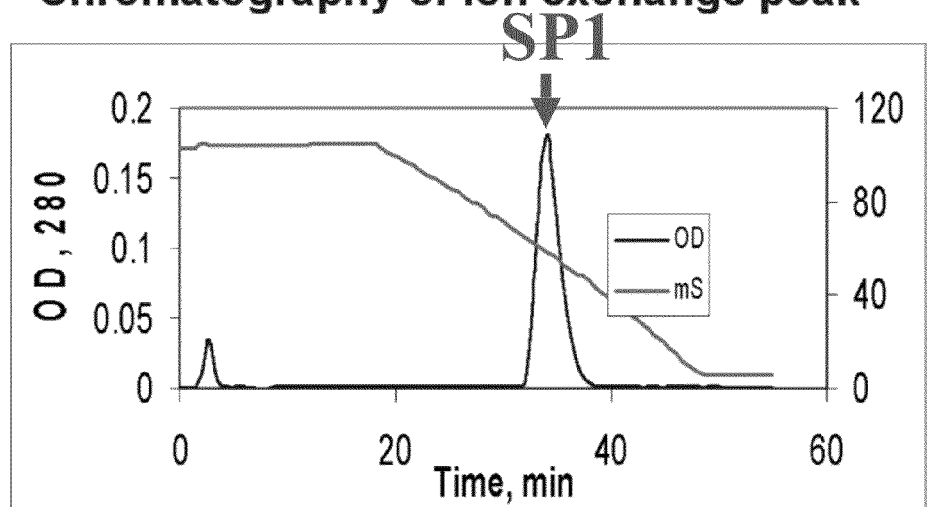
Figure 6C:
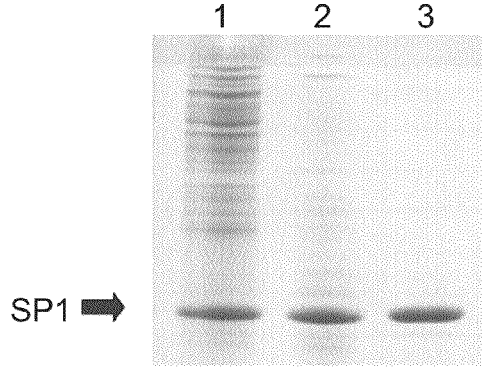
Figure 8:
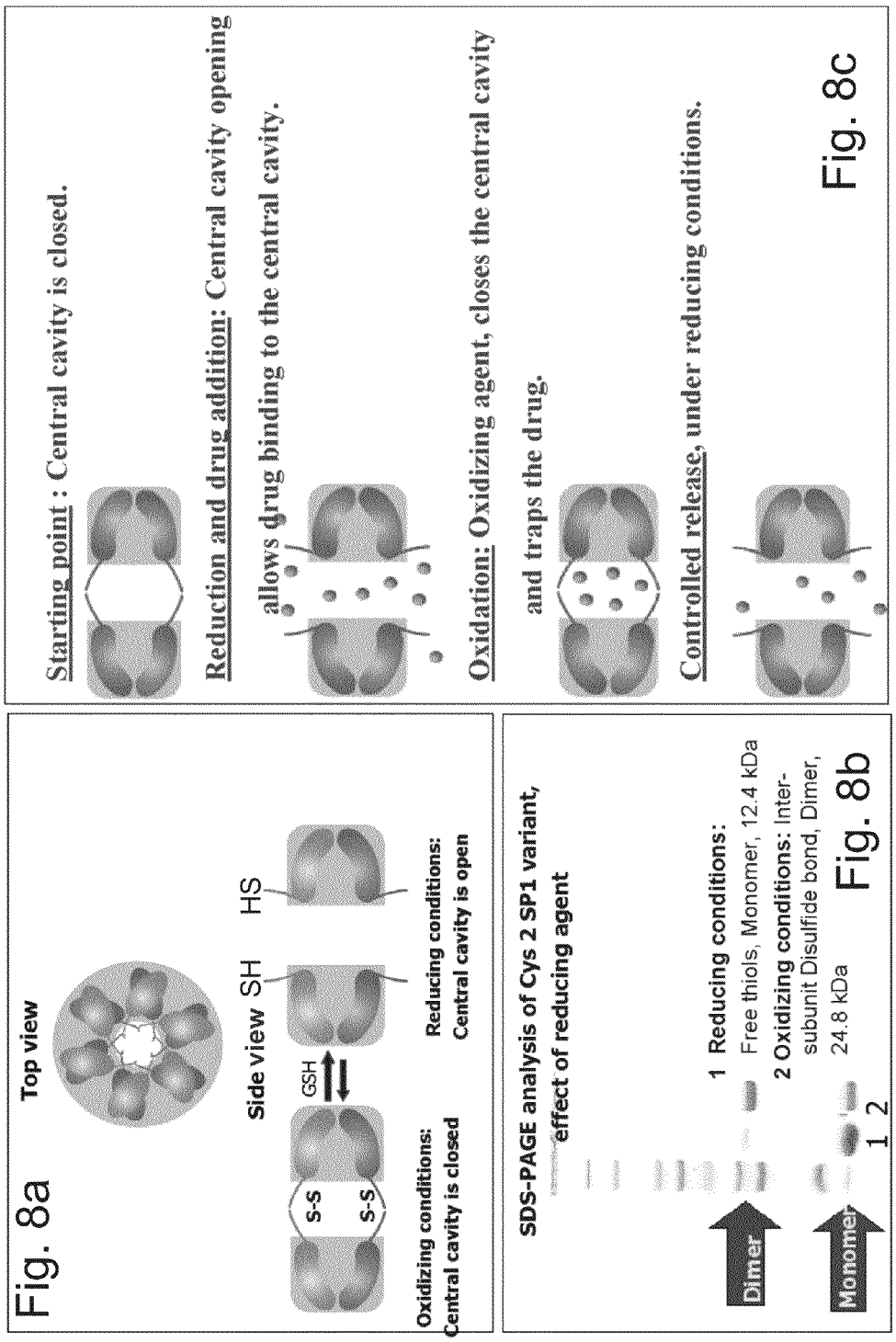
Figure 9:
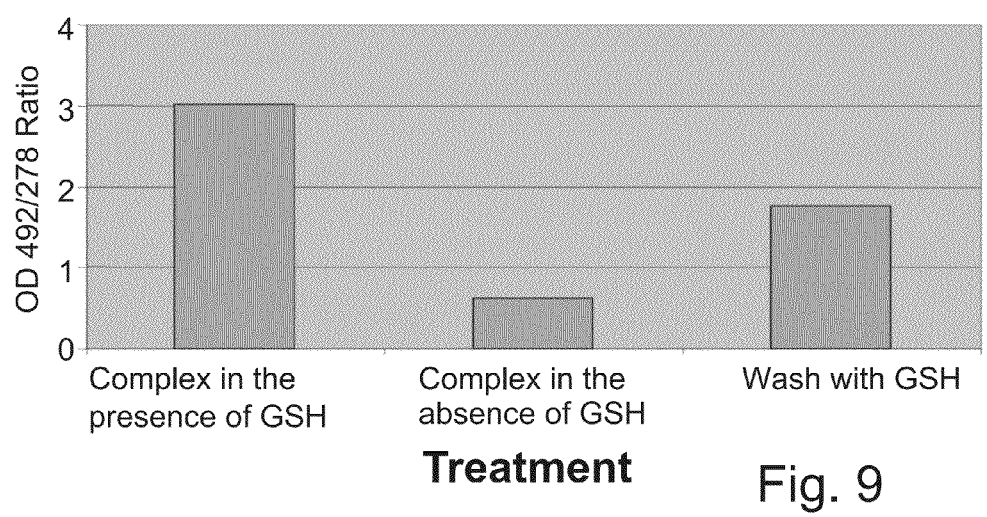
Figure 30:
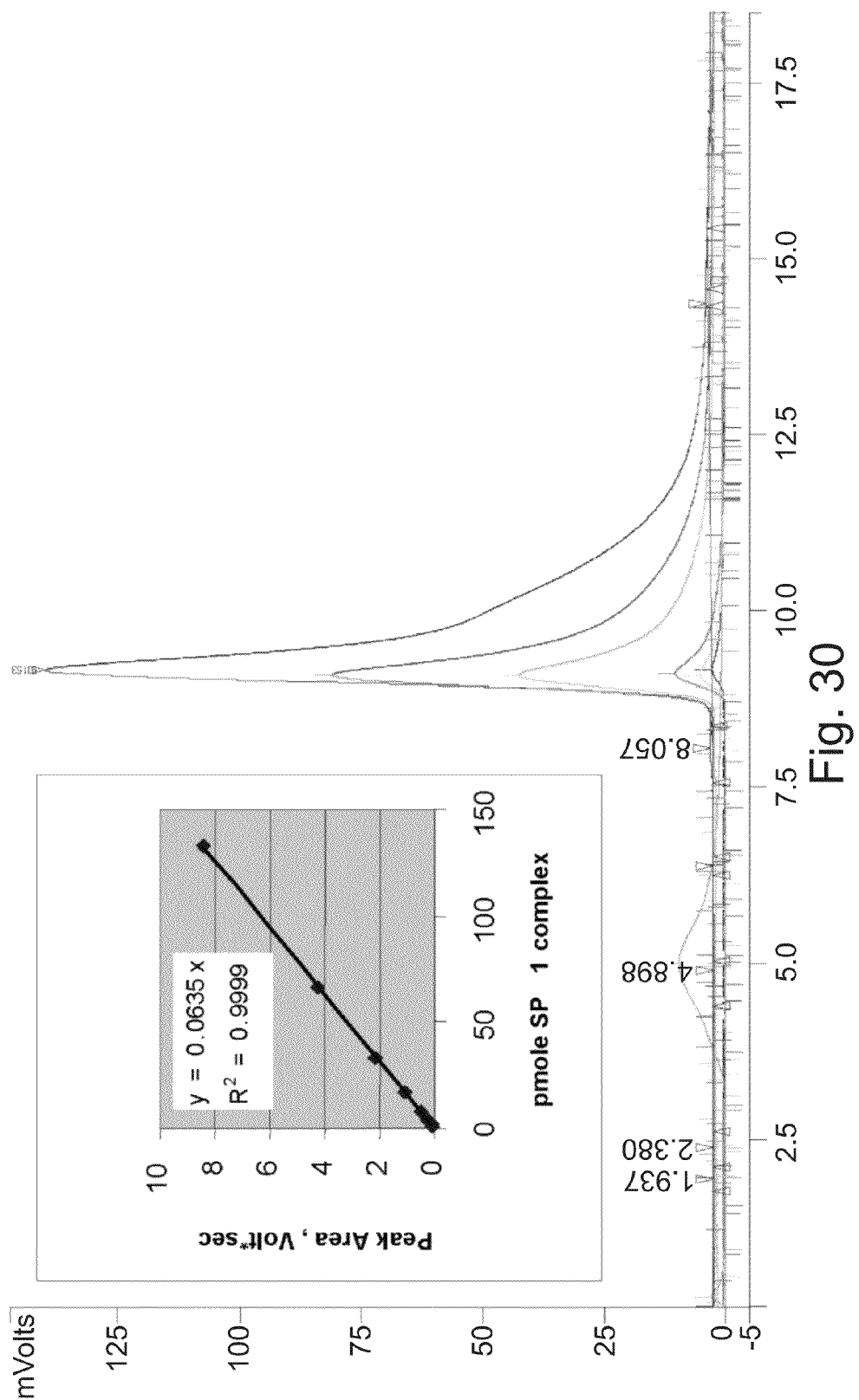

Purification of SP1 protein is enabled by virtue of its exceptional stability, which allows partial extraction by heat treatment (see Methods, hereinabove). The resultant heat resistant fraction is 30% pure (FIG. 6, lanes 1 and 2). Further purification yields a chromatographically pure preparation of SP1, which can be detected as a single peak on reverse phase HPLC and size exclusion chromatography (FIG. 6, lane 3, FIG. 7 and FIG. 30).

SP1 Dodecamer: The dimer-dimer contacts predominantly involve hydrophilic side chains and charged groups or are mediated by water molecules. These contacts take place mainly along the B1, H1, and the N-terminal tails (see Dgany, 2004). As a result of the interdimeric interactions six dimers create a ring-like structure around a pseudo 6-fold axis. The ring-like structure of the dodecamers has an outer radius of ~50 Å and an inner radius of ~15 Å. The loop including residues 18-22 in each dimer protrudes toward the solvent, whereas the arms of the N-terminal are extending toward the inner part of the ring-like structure. The 6-fold symmetry is broken, because the contacts between equivalent molecules in neighboring dimers are not identical (Dgany 2004).

Example 2

SP1 is a Boiling- and Denaturing-Stable, and Protease-Resistant Molecule

The stability of the SP1 complex in the presence of SDS was examined by incubating purified SP1 with SDS at different molar ratios and at different temperatures. Dissociation of the SP1 complex to monomers required a molar ratio greater than 600:1 (SDS:SP1-monomer) accompanied by boiling before loading onto the gel. Without boiling, even at a ratio of 3467 to 1, SP1 remained as a complex on SDS-PAGE. Incubation of SP1 with 1734-fold SDS (1%) at temperatures of 80° C. or lower did not cause significant disassociation of the complex (Wang 2006).

SP1 protein exhibits exceptional heat stability, which allows partial extraction of crude cellular preparations by heat treatment, as mentioned in Example 1 hereinabove. FIG. 6 shows the degree of purity achieved by heat treatment.

Figure 5A:
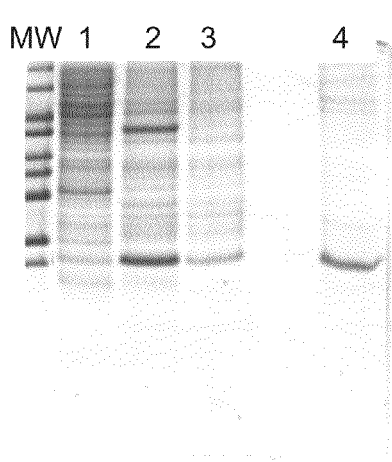
Figure 5B:
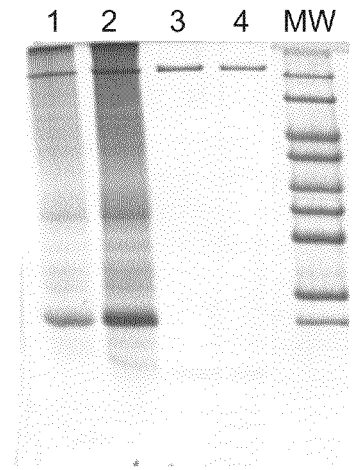

Differential scanning calorimetry study of SP1 indicates in a Tm of 107° C. for SP1. These results further support our previous findings that SP1 is a boiling stable protein and that the high oligomeric form dissociates only upon boiling in the presence of 2% SDS (Dgany 2004). Further, folding and refolding of inclusion bodies including insoluble SP1, and the heat stability of the unfolded proteins indicate that the intact monomer, as well as the oligomer, is heat resistant (FIG. 5).

SP1 is vulnerable to V8 protease or subtilysine (alcalase, Novo Industries) digestion when disassociated to its monomeric form (boiled in 0.5% SDS, or dissolved inclusion bodies). However, V8 protease was unable to digest the intact oligomer (see FIG. 5). When the oligomer-protease mixture was further boiled in SDS sample buffer, only the SP1 monomer was observed and no peptide fragment was detected on the gel. When the same mixture was subjected to SDS-PAGE analysis without boiling, an intact complex was observed. Similar results were obtained with trypsin and proteinase K and subtilysine, indicating the superior resistance of the SP1 complex to a wide variety of proteases (Wang 2002, Wang 2006). Thus, whereas properly folded SP1 protein is protease resistance, unfolded protein, susceptible to protease, can be removed by protease and heat treatment (FIG. 5).

Figure 18:
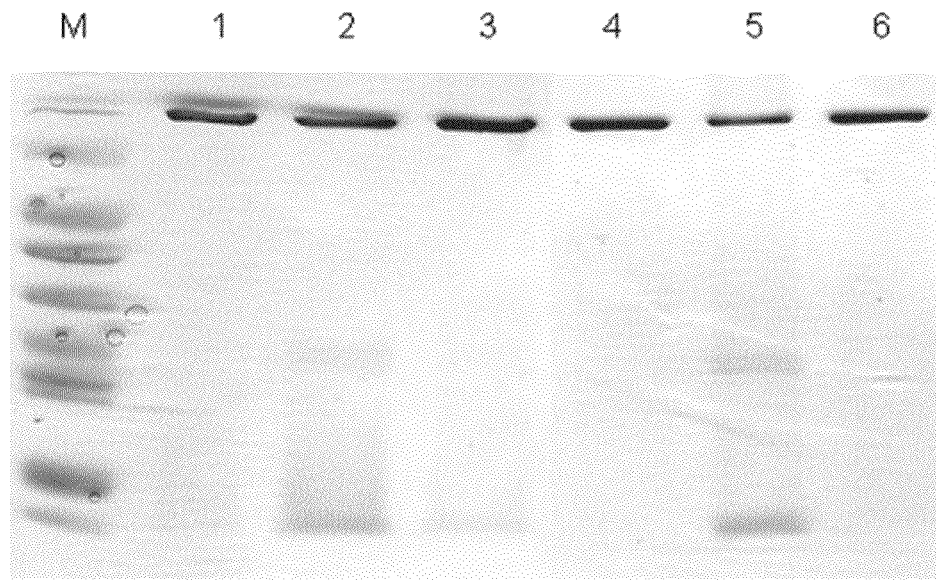
Figure 20:
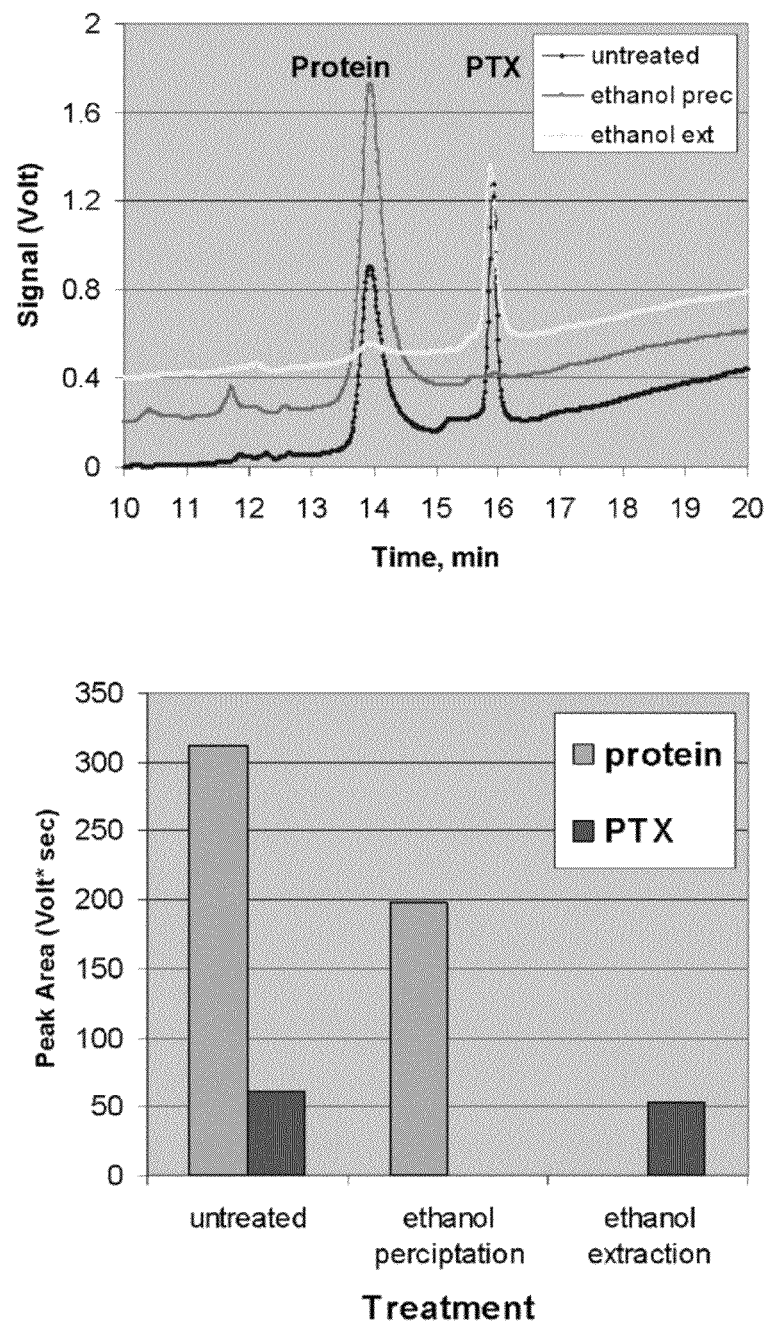
Figure 21:
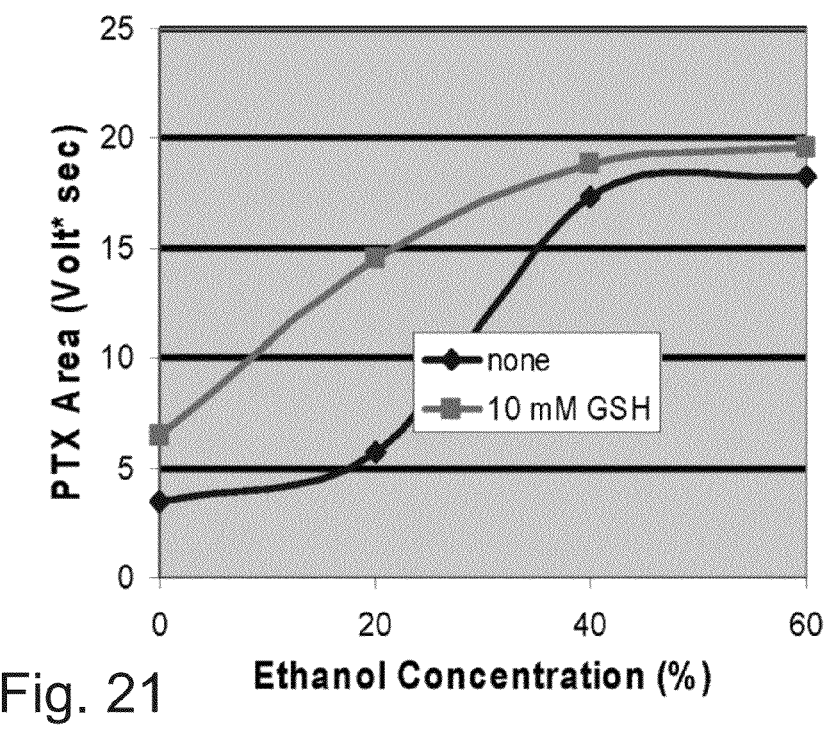
Figure 22:
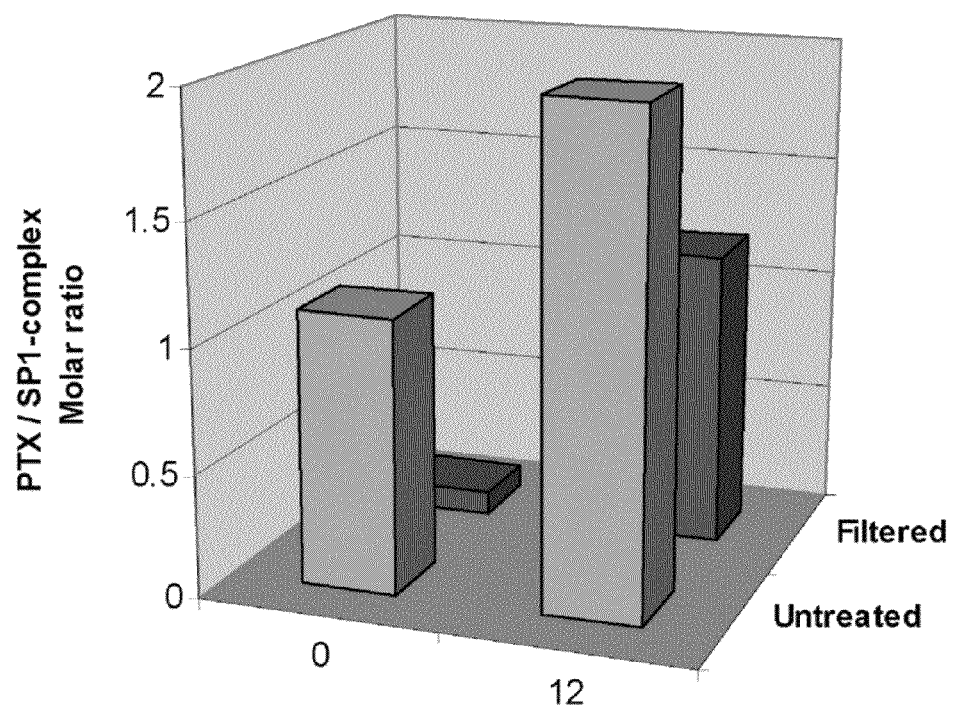
Figure 23:
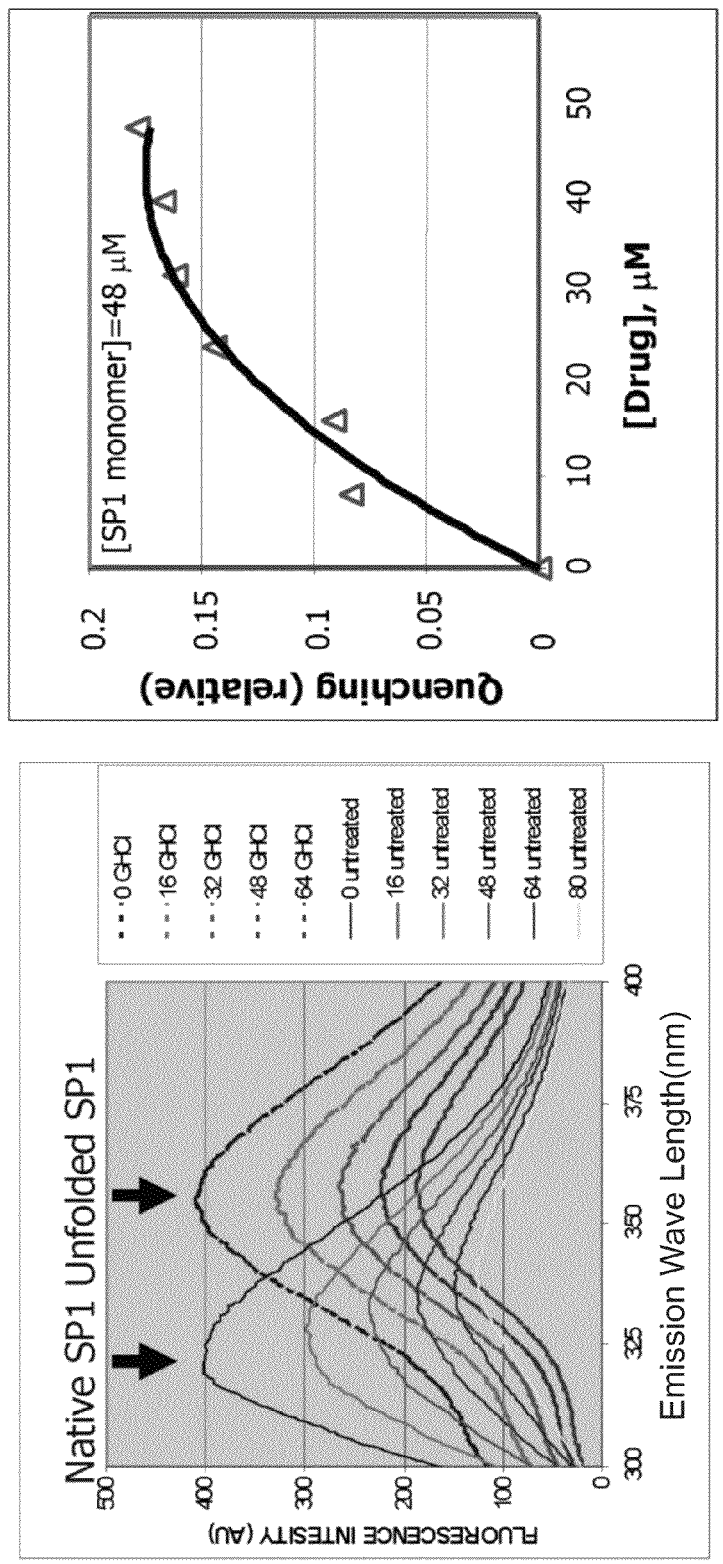

In order to further test the stability of SP1 and SP1 oligomeric complexes, wild type SP1 and the SP1 variant Cys2 SP1 were dissolved in buffer, exposed to organic solvents methanol and hexane, and analyzed by SDS-PAGE (FIG. 18). Predominantly high molecular weight oligomer complex form was detected in all samples treated (FIG. 18, lanes 1-3), indicating that the SP1 complex is resistant to denaturation by organic solvents.

Thus, the SP1 complex shows surprisingly strong resistance to temperature and detergent denaturation, organic solvents and to proteolytic degradation.

Example 3

SP1 Variants

SP1 variants can be constructed to enhance, or otherwise alter SP1 stability, capabilities for oligomerization and/or binding and/or complexing with other molecules and/or ability to form inter-subunit disulfide bonds and/or change the dimension of the central cavity. Numerous SP1 variant proteins were constructed to investigate the effects of specific alterations on properties of SP1.

Figure 4:
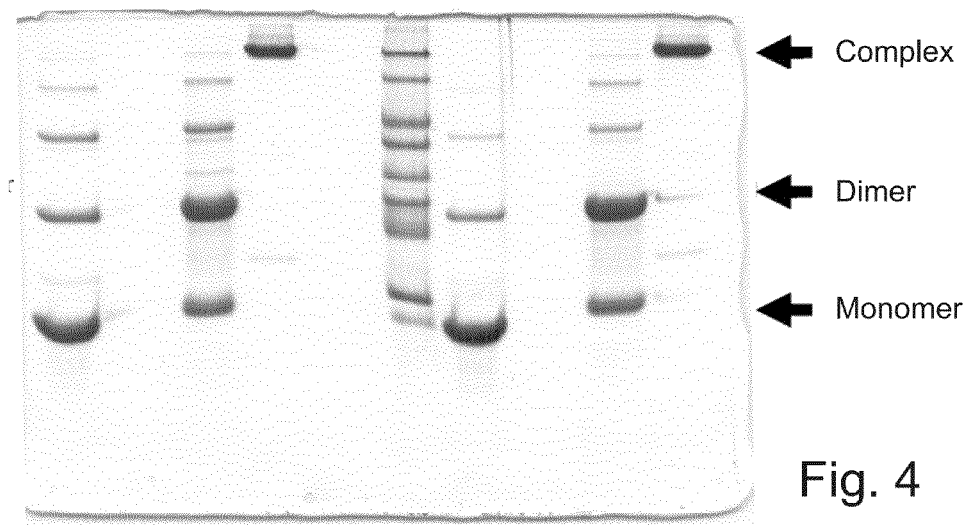

The N-terminal segment points toward the solvent and apparently is not involved in protein folding or stability. Therefore it was predicted that N-terminus mutations would not alter protein structure or its stability. In agreement with this prediction all the N-terminus mutants including a mutant protein carrying deletion of the entire N-terminus Δ2-6 assembled into a stable complex (FIG. 3). Further, it was surprisingly uncovered that when the tumor recognition peptides CRGD (SEQ ID NO:5) and RGDC (SEQ ID NO:6) and RGD loop (SEQ ID NO:10) were inserted into the SP1 N-terminus, the fusion proteins formed a boiling stable and protease resistant dodecamer (FIG. 4).

To confirm the localization of the N-terminus a cysteine residue was inserted in position 2 of SP1 (Cys 2 variant, SEQ ID NO:3) (wild type SP1 does not contain any Cys residue). SDS PAGE analysis of the Cys2 variant shows that Cys2 variant readily forms intra molecular disulfide bonds within the complex. To confirm the specificity of the Cys2 insertion we substituted two cysteine residues located in both Loop 2 (40-44) (SEQ ID NO: 18) and Loop 4 (72-73) (SEQ ID NO: 20) which are also exposed towards the central cavity. Table 1 shows that in contrast with the Cys 2 SP1 variant, these mutant proteins fail to form disulfide bonds (under similar conditions). It should be noted that several recombinant SP1 variants fail to form a soluble protein during expression and form inclusion bodies (IB). However, it was uncovered that these inclusion bodies can unfolded with 0.5 M Urea, and refolded by dialysis (FIG. 5).

X-ray crystallography studies (see Dgany et al 2004) indicated numerous putative monomer-monomer and dimer-dimer interactions stabilize the complex, and it is unlikely that one amino acid substitution would dramatically destabilize the protein. Site directed mutagenesis was performed to find the most critical residues for destabilization of dimer-dimer and monomer-monomer interactions. Table 1 hereinabove shows that most substitutions did not destabilized the protein. However, residues 130A (SEQ ID NO: 14), N31A/ T34A (SEQ ID NO: 30), F106A (SEQ ID NO:23) and Y108A (SEQ ID NO:24) (highlighted in Table 1), which are very close to each other in the protein three dimensional structure, were identified as hot spots involved in protein stabilization.

Loop1 (residues 18-22) (SEQ ID NO:6) and L81C (SEQ ID NO:22) are exposed towards the external perimeters of the ring are good candidate for multiple presentation of specific peptide involved in protein-protein interaction as well as interaction with other molecules or surfaces.

N-terminus modifications did not effect the protein structure or stability (for example, dimer formation), but these modifications provided an opportunity to effect changes in the binding and complexing characteristics of the SP1 variants (see Table 1, "N-terminal mutations"), such as complex formation with metal and metal-associated particles and redox-dependent small molecule complex formation.

Some loop 2 modifications (see Δ2-6I40C) can be used for binding of gold nanoparticles through thiol groups in the central cavity (Table 1), without significantly altering the resistant character of the molecule.

Thus, while not wishing to be limited to a single hypothesis, while reducing the present invention to practice, the inventors believe to have uncovered locations and types of modifications of SP1 molecules resulting in SP1 molecules having specific, altered properties.

SP1 variants can assemble into heterodimer: In order to determine whether different variant SP1 monomers can self-assemble to form functional oligomeric complexes, heterodimer formation between variants was tested.

In order to produce the heterodimers, the monomeric form of SP1 was isolated by two methods: electro-elution from SDS PAGE, and by dissolving inclusion bodies.

When SP1 variant Cys2loop1RGd is expressed in recombinant bacteria, the recombinant protein is found in insoluble proteinaceous inclusion bodies. Solubilization of the SP1 variant Cys2loop1RGd inclusion bodies by 5M urea results in release of soluble monomers (see FIG. 5*a*, lanes 1-4), which are capable of spontaneously reassembling to the high oligomeric form (FIG. 5*b*, lanes 1-4).

The ability of SP1 to assemble into a hetero-oligomeric complex was also demonstrated using a similar method. Two variant recombinant SP1 polypeptides were expressed, a six histidine N-terminal tagged SP1 (6His2, SEQ ID NO: 7) and an N-terminal deletion SP1 (ΔNSP1) SEQ ID NO: 2). Monomers of the two SP1 variants were generated by boiling them in the presence of SDS and separation on preparative SDS-PAGE (FIG. 3, lanes 2 and 3). Monomers electro-eluted from the gel were mixed to facilitate the formation of hetero-oligomers (FIG. 3, lanes 4 and 5). To verify the presence of the two SP1 variants in the self-assembled hetero-complex, the co-electroeluted protein mixture was further subjected to nickel affinity column purification (FIG. 3, lanes 6 and 7). Only the histidine tagged protein and its associated proteins were isolated. The SDS-PAGE analysis showed that, the 6HSP1 complex contains two variants of SP1 (see FIG. 3, lanes 5 and 7). The assembly of hetero-oligomer was finally confirmed by eliminating the monomeric forms using Proteinase K digestion, (only the oligomeric form resist the PK digestion) (FIG. 4, lanes 8 and 9).

These results clearly show that monomers of two SP1 variants can indeed retain the ability to self-assemble to a hetero-oligomer complex form.

Example 4

Binding Properties of SP1 Variants

In order to determine the binding properties of the SP1 variants, and to test the capacity of SP1 and variants to stabilize molecules complexed thereto, wild type and variant SP1 was exposed to a variety of biologically active agents, and the resulting complexes tested for activity, stability and bioavailability of complexed agents.

Cys2-SP1 variant: In order to demonstrate the ability to modify and control complexing of agents to SP1, a Cys2 SP1 variant bearing a cysteine residue was inserted in position 2 of SP1 (wild type SP1 does not contain any Cys residue), in the N-terminus which faces the central cavity (Cys 2 variant). SDS PAGE analysis of the Cys2 variant (mixed with sample application buffer and subjected to boiling for 10 min in the presence or absence of 2% β-mercaptoethanol) shows that Cys2 SP1 variant forms disulfide bonds (FIG. 8*b*). Reduced Cys2 SP1 variant (treated with 10 mM DTT) is readily oxidized upon removal of the reducing agent (FIG. 8*b*). The specificity of disulfide binding in Cys-2 SP1 is further evidenced by its failure to react with free sulfhydryl specific reagents such as 5-5'-Dithio-bis(2-nitrobenzoic acid) (DTNB or Ellman's reagent) and fluorescein maleimide (data not shown).

Thus, availability of reactive sulfides in the monomers of the Cys2 SP1 variant can be controlled by alterations in redox conditions. In order to determine the effect of redox-dependent changes on complex formation with agents and other ligands, the dynamics of Cys 2 SP1 complexing with such agents was investigated. FIG. 8 shows one possible model for redox-dependent ligand complexing and release. Without wishing to be limited to one hypothesis, it is proposed that reducing agents such as the reduced form of glutathione (GSH), DTT or β-mercaptoethanol can cleave the disulfide bonds and makes Cys2-SP1 available for complex with the ligand. The complexed ligand can be bound by oxidation, and can be dissociated upon reduction FIG. 18 *b*, and below). This is of special consideration, since solid tumors are characterized by hypoxia, and they accumulate large amounts of cellular reducing equivalents (Kim, 2003). Furthermore it was suggested that high GSH concentration is involved in drug resistance. Thus, therapeutic or other agents complexed with Cys2-SP1 under oxidation, can be stabilized and transported by the SP1 variant, until reaching the target tissues, whereupon reducing equivalents will enhance release of the agent(s), as is illustrated in FIGS. 8*b* and 8*c*.

Controlled complexing and release of agents and ligands by Cys2 Sp1 variants was tested using the complexing of fluoresceine amine fluorophore (FA) as a water soluble marker ligand, and doxorubicin (DOX) and paclitaxel (PTX) as models for water soluble and insoluble therapeutic agents, respectively. Ultrafiltration, size exclusion chromatography and reverse phase HPLC analysis (see Methods hereinabove) were used to demonstrate agent-SP1 variant complexing and release, with respect to the following considerations:

1. Efficiency of ligand complexing by Cys2 SP1 variant compared to wild type.

2. Can protein reduction increase ligand complex formation by Cys2 SP1 variant but not wild type SP1 complexing?

3. Can Cys2 SP1 variant oxidation, prior to ligand addition, eliminate ligand complexing?

4. Can reduction of the Cys2 SP1 variant-ligand complex increase ligand dissociation?

5. Can complexed ligand be stabilized by association with the Cys2 SP1?

Fluoresceine amine (FA): FA absorption peak is at 490 nm and at much lower extend at 278 nm (for a given FA concentration $OD_{278}/OD_{490}=0.19$) (see FIG. 31), when SP1 absorption peak is at 278 nm (see FIG. 30), and it is not detected at 490 nm. Cys2 SP1 has absorption peaks at 225 nm and 278 nm (see FIG. 32). FA complexing with the Cys2 Sp1 variant was determined following incubation of FA and Cys2 SP1 variant in the absence or presence of GSH, followed by protein oxidation, ultra filtration (30 kDa cutoff) and exhaustive wash of the retained fraction with PBS with or without GSH. Absorption analysis at both 278 and 490 nm. (FIG. 9) shows that protein reduction with GSH increases complexing of FA and Cys2 SP1, and that reduction of the FA-Cys2 SP1 complex increases FA dissociation.

Size exclusion chromatography (see Methods hereinabove) was used to compare redox-dependent FA complexing with Cys SP1 variant and wild type SP1. FIG. 10 shows that wild type SP1 hardly forms complexes with the FA marker, in the presence or absence of reducing agents. In contrast, Cys2 SP1 variant complexes with the FA marker with greater than 3-fold efficiency in the presence of reducing agents (FIG. 10).

The superior control of FA complexing with Cys2 SP1 is shown in FIG. 11. At low ligand concentrations (10 μM), no discernable FA complexing was detected for wild type SP1, whereas Cys 2 SP1 variant showed efficient complexing. At greater concentrations (≥100 μM), the Cys2 SP1 variant complexes with the FA marker with an efficiency greater than 3-fold that of wild type SP1. These results show that Cys2 SP1 variant can efficiently complex with ligands and agents, compared to wild type and that protein reduction increases ligand complex formation by the Cys2 SP1 variant, but not the wild type SP1.

Complex formation and covalent modification of SP1: Chemical modification of SP together with a small molecule allows creation of two types of new complexes: the small molecule can create both a covalent bond with the protein or a non-covalent bond by creating a new site for molecular association.

This was shown with fluorescein amine complexing with SP1 using the carboxylic acid residue modification reagent, 1-ethyl-3-(3-dimethylaminopropyl)carbodiimide (EDAC) as a covalent reactive group (Table 5, hereinbelow). Similarly to native SP1, the SP1-FA complex, is resistant to elevated temperatures. Non-covalent bound FA dissociates from the protein only upon boiling in the presence of SDS. Table 5 shows the effect of heat and protease treatment on fluorescence intensity of SP1-bound FA, showing that about 80% of fluorescein amine is associated with the protein through non-covalent association. It is also shown that complexed SP1-FA retains the characteristic heat-stability and protease resistance of the wild-type SP1.

TABLE 5

Stable SP1-FA complex formation using (EDAC) covalent binding

| SP1-FA conformation | Fluorescence intensity of SP1-FA (% of control) Treatment | | |
|---|---|---|---|
| | Control (none) | Protease | Heat |
| Oligomer Complex | 100% | 90% | 95% |
| Monomer | 22% | 21% | 19% |

Doxorubicin (DOX): The anthracycline antibiotic doxorubicin is one of the most useful antineoplastic agents, active against several solid tumors as well as hematological malignancies. It is used to treat neoplastic conditions such as acute lymphoblastic leukemia, acute myeloblastic leukemia, Wilms' tumor, neuroblastoma, soft tissue and bone sarcomas, breast carcinoma, ovarian carcinoma, transitional cell bladder carcinoma, thyroid carcinoma, gastric carcinoma, Hodgkin's disease, malignant lymphoma and bronchogenic carcinoma. Furthermore, many colloidal carriers of doxorubicin, such as liposomes and polymeric nanoparticles, have been studied with the aim of reducing cardiac toxicity and improving therapeutic efficacy.

In order to determine the ability of SP1 to form complexes with DOX, concentrations of both SP1 and the SP1-DOX complex (in the retained fraction) and free DOX (in the flow-through fraction) were determined spectroscopically at both 477 and 278 nm. DOX has a unique optical properties, its absorption peak is at 477 nm, and to lower extend at 278 nm (for a given DOX concentration $OD_{278}/OD_{477}=0.77$) (see FIG. 29), while SP1's absorption peak is at 278 nm, and it is not detected at 477 nm (FIGS. 30 and 32).

Wild type SP1 and the Cys2 SP1 variant were tested for their ability to complex with DOX in the presence and absence of DTT, as determined by ultrafiltration. FIG. 12 shows that DOX forms complexes with DTT-reduced Cys2 SP1 variant to a much greater extent that with DTT-treated wild type SP1, and that exposure to DTT greatly enhances DOX complexing by the Cys2 SP1 variant. Reduction with glutathione (reduced form) instead of DTT improves DOX complexing by the Cys2 SP1 variant (data not shown).

In order to determine whether other manipulations of the redox state of the chemical environment of the Cys2 SP1 provided additional control of DOX complexing, DOX complexing to wild type and Cys2 variant SP1 in the presence or absence of an oxidizing agent was assessed. FIG. 14 clearly shows that oxidation of Cys2 SP1 variant prior to DOX addition eliminates DOX complexing. Thus, without wishing to be limited to a single hypothesis, the oxidation dependent inhibition of DOX-Cys2 SP1 variant complex formation could indicate that reduction of the disulfide bonds in Cys2 SP1 variant facilitates DOX complex formation.

In order to further determine the character of Cys2 SP1-DOX complexing, Cys2 SP1 complex formation with DOX was determined by size exclusion chromatography at both 475 and 278 nm. FIG. 13 shows the Cys2 SP1-DOX peak eluting at 7 min, detected at both 278, 475 nm. Extensive wash with PBS, without added reducing agent (FIG. 13, no GSH) does not disrupt the Cys2 SP1-DOX complex. Addition of a reducing agent (GSH), however, results in loss of the DOX peak (475 nm) without loss of any of the Cys2 SP1 protein peak (278 nm). Without wishing to be limited by a single hypothesis, this may be understood to mean that DOX displays a high affinity to the SP1 complex, and is dissociated from the complex only upon extensive wash (at low free ligand concentration). Evidence that DOX binds tightly to the SP1 was also provided by the observation that DOX does not dissociate from the SP1-DOX complex after 7 days incubation at room temperature (under oxidizing conditions, data not shown). It also should be noted that the SP1-DOX complex stays intact even after ethanol precipitation (see FIG. 35), indicating high stability of the complex, and ease of removal of free DOX and the purification of complexed SP1-DOX.

Analysis of Cys2 SP1-DOX complex by reverse phase HPLC analysis can be accomplished by eluting the bound species from the resin (C-18, Pharmacia-Biotech, Uppsala, Sweden) at different acetonitrile concentrations, and measuring the absorption at both 477 and 278 nm. In order to test the effect of further manipulation of the redox state on Cys2 SP1 DOX complexing, wild type SP1 and the Cys2 SP1 variant were tested for their ability to complex with DOX under reducing conditions (GSH, reduced protein) or oxidizing conditions (peroxide, oxidized protein). FIG. 14 shows that the reduced, and not oxidized Cys2 SP1 variant forms complexes with DOX, and that no complexes are formed between wild type SP1 and DOX.

FIG. 14 further shows that free, uncomplexed DOX can be found in association with the SP1 protein under certain conditions. Although the samples were extensively washed by ultra-filtration before application to the column, a significant portion of free DOX is observed in the reduced (DTT treated) Cys2 SP1 sample, indicating that some DOX remains associated with the Cys2 SP1, and it can become dissociated from the protein when subjected to harsh conditions (75% acetonitrile+0.1% TFA).

The association of DOX with Cys2 SP1 variant was further investigated by SDS PAGE analysis, and fluorescence imaging. FIG. 15 shows that the DOX remains associated with all forms of Cys2 SP1 (116 kDa complex, 12.4 kDa monomer and 24.8 kDa dimer), even under harsh (reduction and boiling) conditions. Further, comparison of free DOX detected with or without reducing agents (FIG. 15, lanes 2 and 4) shows that complex reduction stimulates DOX released from the Cys2 SP1-DOX complex. It will be noted the relative intensity of the bands in this gel does not necessarily reflect the absolute amount of DOX, possibly due to a self quenching phenomenon. Further SDS PAGE analysis uncovered that the Cys2 SP1-DOX complex is resistant to protease (lanes 1-3, 5), heat (85° C./30 min) (FIG. 16, lanes 1-4) treatments, and incubation in serum (37° C./24 h) (FIG. 16, lanes 1 and 2). The superior resistance of the Cys2 SP1-DOX complex to dissociation in harsh conditions is significant for storage, purification, in-vivo longevity and other uses of SP1-drug complex.

Paclitaxel (TAXOL PTX): A common problem in clinical use is the poor solubility of many drugs. As shown by Dgany et al (Dgany, 2004), the x-ray crystallography data for SP1 predicts that Helices H1 and H2 define an external convex surface with numerous hydrophilic and acidic side chains facing toward the solvent. The inner side of this surface and the opposing β-sheet enclose a hydrophobic central cavity rich in aromatic and hydrophobic residues. In order to determine whether this effects solubilization of small hydrophobic molecules, SP1 was complexed with Paclitaxel.

The diterpenoid derivative paclitaxel has broad antineoplastic activity (ovarian cancer, breast cancer, non-small cell lung cancer, AIDS-related Kaposi's sarcoma) and a unique mechanism of action promoting the polymerization and stabilization of tubulin to microtubules. One of the major clinical problems of using paclitaxel is its very low solubility in water, due to its extremely hydrophobic nature. In order to enhance paclitaxel's solubility, a mixture of 50:50 Cremophor EL (CrEL, a polyoxyethylated castor oil) and ethanol is used in the current clinical formulation with serious side effects for 25-30% of treated patients.

To circumvent these problems, a great deal of effort has been directed to developing new systemic paclitaxel formulations, Cremophor-free with enhanced circulation time. However, none of the present formulations have overcome the problems.

In order to determine the stability of the SP1 complex in organic solvents, SP1 and Cys2 SP1-variant (SEQ ID NO: 3) were dissolved in organic solvents, dried, reconstituted with aqueous solvent, and separated on SDS-PAGE. FIG. 18 shows the persistence of high molecular weight oligomer complexes in both aqueous (Sodium phosphate, lanes 1 and 4) and organic solvents (lanes 2, 3, 5 and 6). Further, hexane-treated SP1 or Cys2 SP1 variants are resistance to protease treatment (data not shown).

Figure 25B:
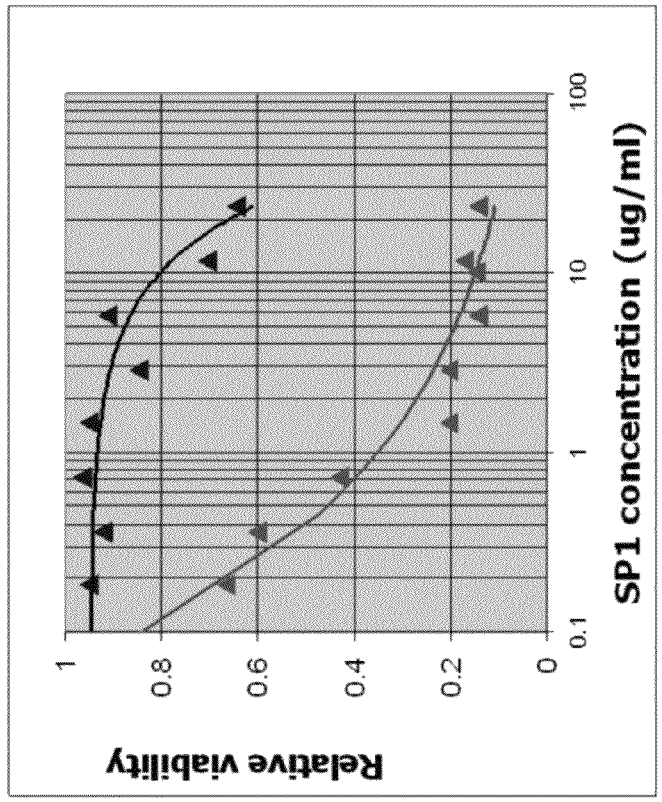
Figure 25A:
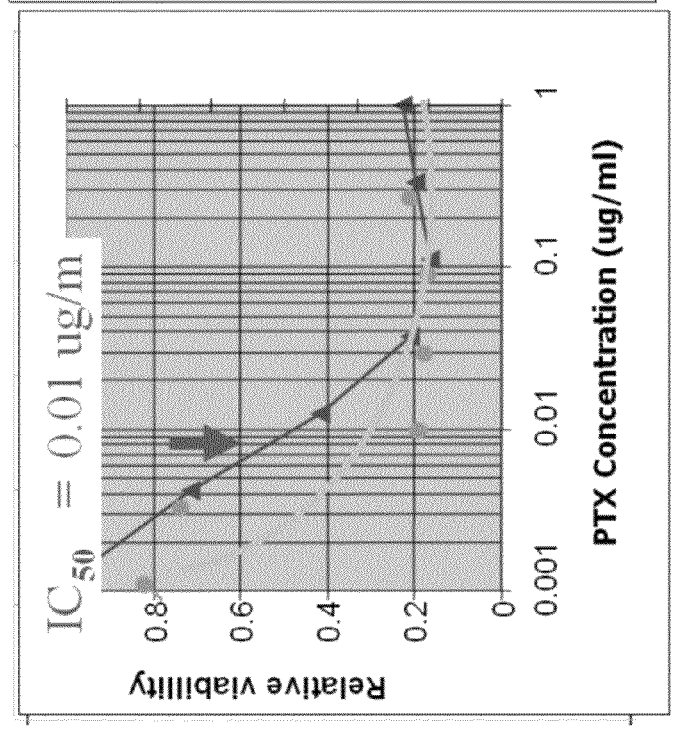

Next, the poorly soluble PTX was mixed with lyophilized SP1, in an organic solvent, in the presence of a reducing agent. Following evaporation of the organic solvent, the PTX-SP1 complex was tested for solubility in an aqueous solvent. FIG. 19 shows a RP HPLC analysis of the enhanced solubility of the SP1-PTX complex, as compared to free PTX (in DMSO) and uncomplexed SP1. The HPLC results emphasize the poor solubility of PTX in water (magenta), with the SP1-PTX complex (red) appearing as the SP1 and PTX peaks (at 15.8 and 17.4 min, respectively). Ultrafiltration of the SP1-PTX complex (through a molecular weight cutoff membrane of 30 kDa) shows that the complexed PTX is retained over the membrane, indicating strong complexing with the SP1.

PTX does not have a unique absorption spectrum and bound PTX cannot be detected. PTX dissociates from the SP1-PTX complex in the presence of high acetonitrile concentrations and it can be detected in the same elution as free PTX. To demonstrate that all PTX is eluted from the SP1-PTX complex on the column, PTX was extracted from the complex using 80% ethanol (FIG. 20), precipitating the SP1 protein. FIG. 20 shows that all PTX can be recovered in solution, (in contrast with SP1-DOX complex, which precipitates under similar conditions). At lower ethanol concentrations, PTX can also be extracted, allowing separation of the complexed SP1-PTX and the free PTX by ultrafiltration (FIG. 20 and FIG. 21, lower plot).

In order to determine the efficacy of Cys2 SP1 variant complex formation with poorly soluble molecules, and the effect of reducing conditions on the formation of PTX-Cys 2 SP1 variant complex, PTX was extracted at increasing concentrations of ethanol from the Cys 2 SP1 variant-PTX complex, in the presence or absence of 10 mM GSH. FIG. 21 shows that the reducing agent induces PTX extraction at a lower ethanol concentration. The effect of reduction on complex formation was also tested. FIG. 22 shows that the presence of the reducing agent β-ME (12 mM) significantly enhances Cys2 SP1-PTX complex formation. Unexpectedly, Cys2 SP1-associated PTX was detected in the absence of the reducing agent, but the associated PTX was removed by filtration.

These results clearly show that SP1 and SP1 variants form stable oligomeric complexes in organic as well as aqueous solvents, that SP1 and SP1 variants can form complexes with poorly soluble molecules, and that the solubility of poorly water soluble molecules, such as PTX, is significantly enhanced by association with the SP1 and SP1 variants. Such solubilization capability of SP1 has great importance for clinical and other applications of SP1 and SP1 variants, for example, for drug delivery.

Vinblastine: Vinblastine, a vinca alkaloid, is mainly useful for treating Hodgkin's disease, lymphocytic lymphoma, histiocytic lymphoma, advanced testicular cancer, advanced breast cancer, Kaposi's sarcoma. Vinblastine binding to SP1, was determined by Intrinsic Tryptophan fluorescence measurements.

SP1 has only one Tryptophan residue (Trp 48). Trp 48 maximal excitation and emission wavelength are 286 nm and 321 nm respectively. Upon protein unfolding in 6M Guanidinum HCl, the maximal emission wavelength is shifted from 321 to 340 nm. FIG. 23 shows that association of SP1 with Vinblastine caused fluorescence quenching accompanied by a red shift (upon addition of 80 μM Vinblastine its maximal emission wavelength is shifted to 356 nm). Unfolded protein fluorescence is also quenched by Vinblastine (FIG. 23), but unlike the native protein it is not accompanied by red shift. Thus, folded SP1-Vinblastine association can be detected, and quantified by changes in its Intrinsic Tryptophan fluorescence.

Example 5

Enhanced Biological Activity of SP1-Associated Drugs

In order to evaluate the efficacy of SP1 as a drug delivery agent, or carrier, biological activity of the SP1 and SP1 variant-complexed drug molecules was determined. Thus, SP1-complexed drug and marker molecules were tested in in-vitro models and animal models of neoplastic growth.

SP1-DOX in colorectal cancer cell line: The human colorectal adenocarcinoma cell line, HT-29, was used to evaluate the biological activity of the SP1-DOX complex, compared to that of the free drug and un-complexed SP1 protein. The inhibition concentration 50% ($IC_{50}$), defined as the dose of compound that inhibited 50% of cell growth, for free doxorubicin and the SP1-DOX complex (prepared by either ultrafiltration or ethanol precipitation) were similar (FIG. 24*a*, 0.6 ug/ml), while uncomplexed protein was inactive. Thus, the SP1-DOX complex is at least as biologically active as free DOX.

When the IC$_{50}$ values for free PTX (in DMSO) and the SP1-PTX complex were compared, the value for both preparations were similar (0.01 ug/ml, FIG. 25), while the unloaded protein (prepared in parallel to PTX-SP1) was inactive (FIG. 25). However, SP1-PTX complex remained biologically active ever after at least 3 weeks storage in aqueous solution, conditions under which free PTX becomes inactive. Thus, the complexing of PTX with SP1 clearly increases the stability of the drugs biological activity.

In order to determine whether SP1-PTX cytotoxicity is associated with trans-membranal transport of SP1, cells were exposed to both free and SP1-complexed PTX along with a 10-fold accesses of uncomplexed SP1. No competition was observed in either case (data not shown). While not wishing to be limited by a single hypothesis, it is noted that the absence of competition can indicate either very fast uptake of the SP1-drug complex by the cells, or that the drugs dissociate from the complex outside the cell exert their cytotoxic effects in an uncomplexed manner. The latter explanation can be associated with high extracellular GSH concentrations, affecting the redox state of the immediate cellular environment.

Figure 26:
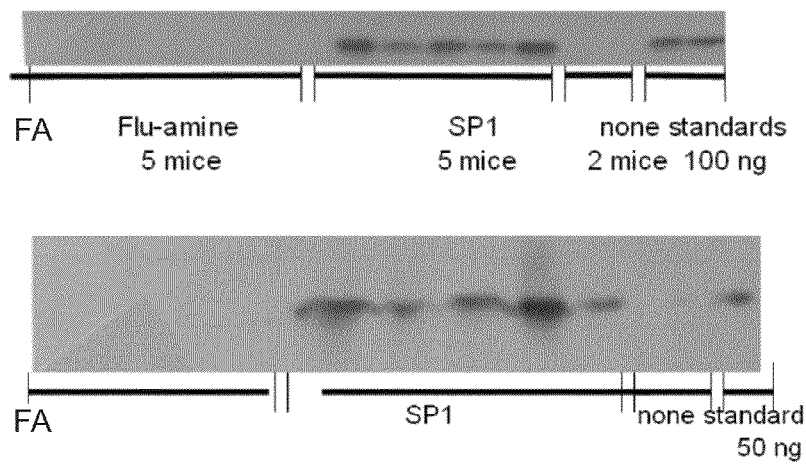

Biodistribution of SP1 in vivo: To follow the rate of accumulation in a tumor, and the clearance of administered SP1-complexed molecules from the circulation, Fluoresceine and SP1-Fluoresceine complex was injected to C57B1 male mice bearing the B16-F10 (B16) melanoma tumor. 24 hours after the SP1-Fluoresceine injection, the mice were bled, the animals sacrificed, tumors removed and homogenized in buffer, and the tissue extracts heat-treated to remove none-specific proteins. In order to detect accumulation of the SP1-FA complex in the target tissue, the samples were subjected to SDS-PAGE analysis and immuno-blot detection with an anti SP1 antibody. FIG. 26 shows that about 2-5% of injected SP1 complex is found in the tumor, and about 3-15% of injected SP1 remains in circulation 24 hours post injection, while the free Fluoresceinamine is rapidly cleared.

Repetitive injections of SP1 to wild type mice were conducted to demonstrate that SP1 does not induce any significant immunological response or toxicity. 35 mg/Kg SP1 or PBS control were injected iv (tail vein) to C57B1 mail mice on days 0, 9, 16, 23, 37 and 53 (6 and 5 animals in the SP1 and PBS groups, respectively). 55 days past the first injection the animals were sacrificed and their livers were subjected to histopathology analysis. Four out of six SP1 treated animals did not show any pathological response, all through the experiment, up to the 55 days. Histopathology analysis demonstrated that the liver of all animals from both groups appeared normal. Two out of 6 animals died after 17 days from an unknown reason. Five out of five PBS treated animals also showed no pathological response throughout the experiment. Histological examination of the liver did not show any signs of pathology.

In order to determine the degree of immunogenicity of SP1, anti SP1 antibody production in both PBS- and SP1-treated animals was detected using ELISA, using either directly immobilized SP1 or rabbit anti SP1 antibodies (second antibody was HRP conjugated anti mouse IgG). Serum obtained from both PBS- and SP1-treated animals had negligible anti-SP1 antibody reaction, with no difference between the two groups. It should be noted that the rabbit anti-SP1 reacts significantly better with the monomer than with the SP1 oligomer complex, even though the animals were immunized against the SP1 complex.

Thus, these results clearly show a biodistribution of SP1 extremely well suited for carrier and drug delivery applications, and the surprisingly non-toxic and non-immunogenic properties of SP1 protein in vivo.

Figures 27A, 27B:
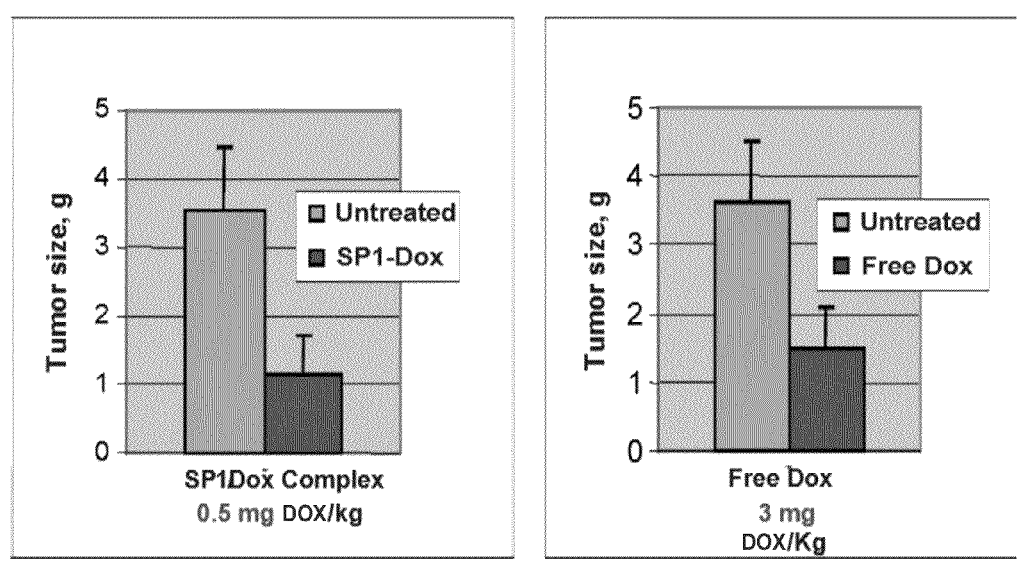

In-vivo anti-tumorogenic activity of an SP-1-drug complex: The effect of SP1-complexing on the anti-tumorogenic activity of DOX was determined in vivo using the LS147 (human colon cancer) model in CD1 nude mice (Meyer 1995). Tumor growth rate of animals receiving SP1-DOX complex or free DOX were (0.5 and 3 mg DOX/kg, respectively, iv to the tail vein two times a week) was compared (FIGS. 27a and 27b). This dose (3 mg/Kg) of free DOX comparable to the maximal tolerate dose in mice. At 35 days past tumor grafting, the animals were sacrificed, tumors were removed and their weight recorded (FIGS. 27a and 27b). Since weight loss is a common side effect of DOX, the animal's weight was also determined (FIGS. 28a and 28b).

Although the free DOX dose was 6-fold higher than that of the SP1-DOX complex dose, the inhibition of tumor growth by SP1-DOX complex, even at 6 times less concentration than the free DOX, was comparably significant. In both cases the average tumor size in the end of the experiment was much smaller than in the PBS-treated animals. Moreover, histological examination of the tumors showed extensive necrosis in the DOX and SP1-DOX complex treated animals.

However, the DOX-treated animals suffered from serious side effects, manifested in over 16% weight lose; surprisingly, the SP1-DOX complex-treated animals did not exhibit any weight loss.

Thus, the results brought hereinabove clearly show that complexing drugs with SP1 enhances important aspects of the drug's effectiveness, such as solubility and stability in solution, and can enable reduction in dosage and undesirable side effects, without concomitant reduction in effectiveness.

Example 6

RP- and Size Exclusion HPLC Profiles of Free and Sp1-Complexed Molecules

Reverse phase (RP) and size exclusion HPLC were used to detect and quantitate molecules complexing with SP1 and P1 variants, such as DOX. PXT and FA.

Figure 29:
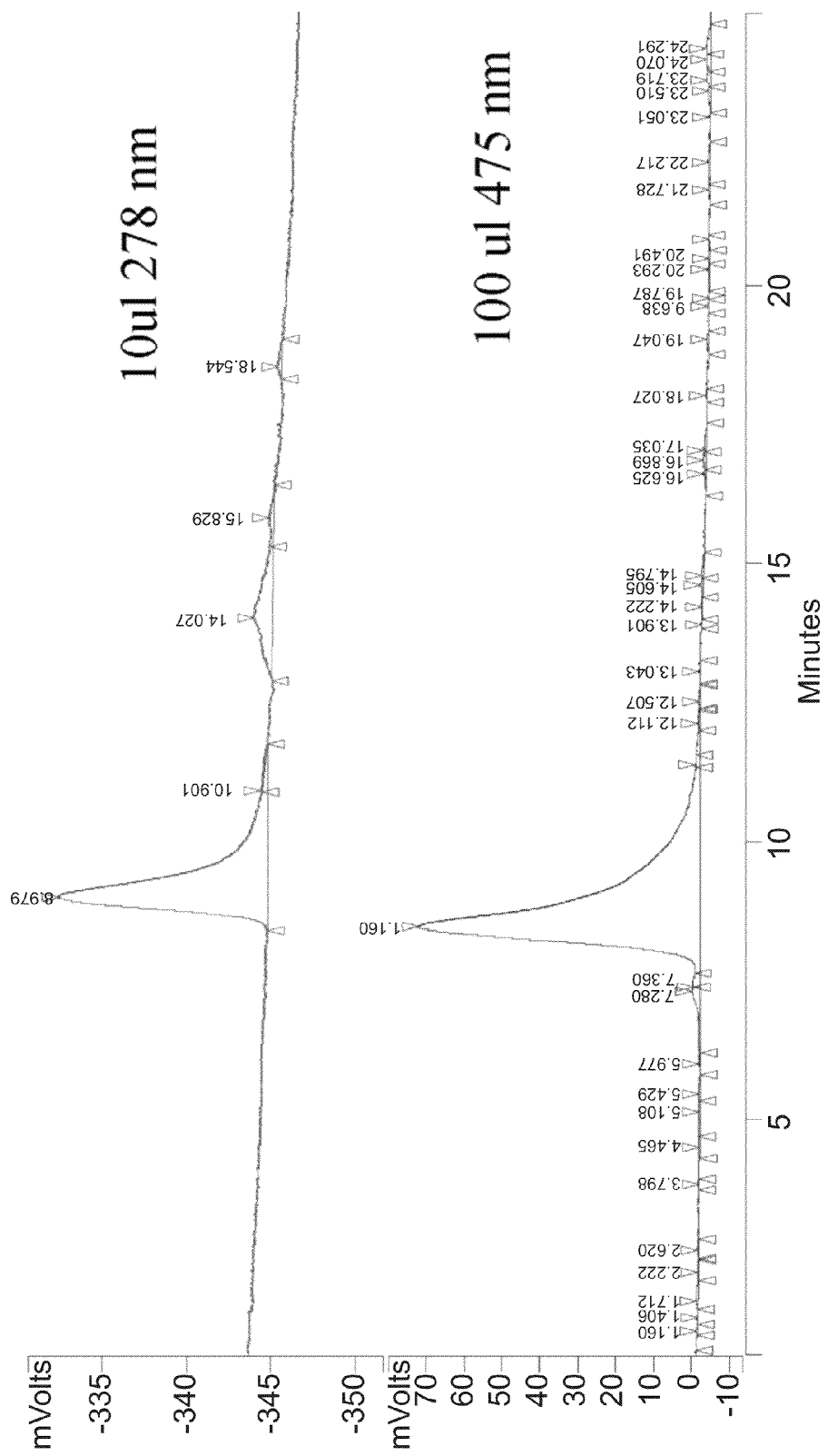
Figure 31:
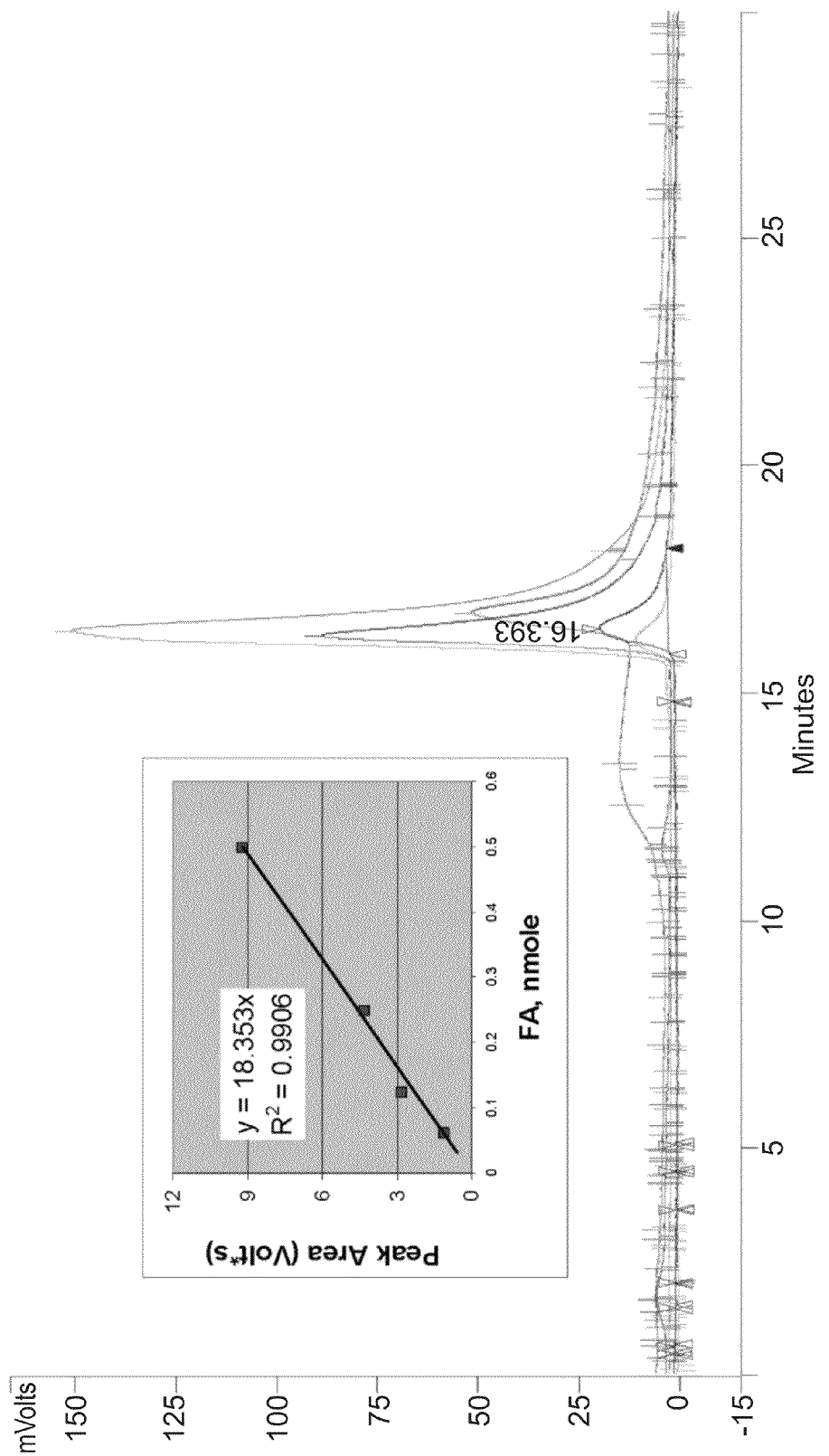
Figure 32:
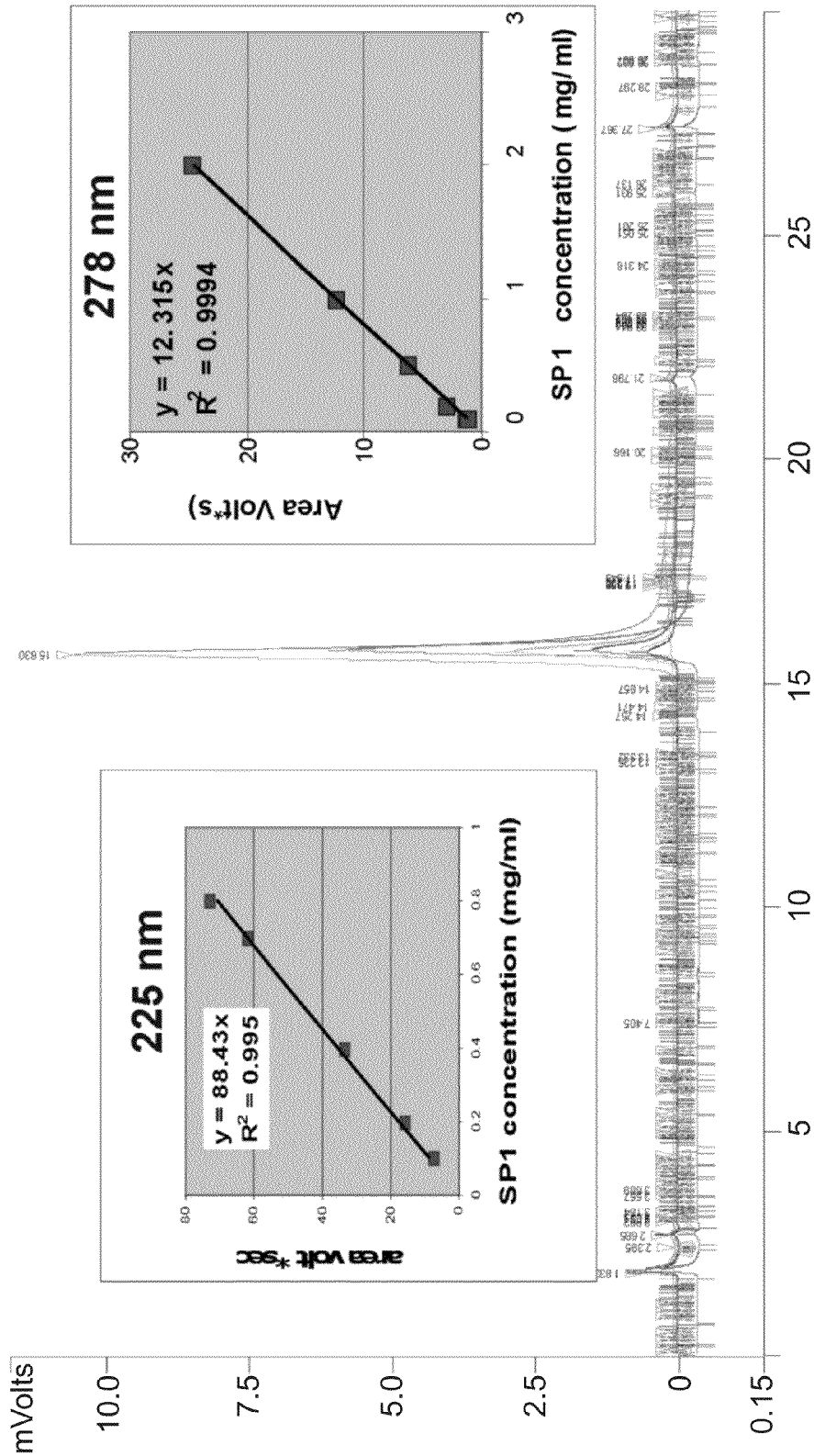
FIG. 32 shows the standard profiles of Cys2 SP1 (determined at both 278 (left panel) and 225 (right panel) nm) on RP-HPLC. Insets show the quantitative detection of the Cys2 SP1 over a range of concentrations.

Size exclusion chromatography is a common method for separation of molecules of different sizes under mild conditions and was employed to test FA and DOX complexing with SP1 under mild conditions. SP1 is eluted from the column after 7 min and is detected at 278 nm only (FIG. 30), and free FA is eluted from the column after 16 min and is detected at 490 nm (FIG. 31). The SP1-FA and SP1-DOX complexes also eluted at the same time, but were detected at 490 and 475 nm, respectively (FIGS. 29 and 31). FIG. 32 shows a typical SP1 standard curve on size exclusion chromatography at 278 nm. SP1 is eluted from the column (TSK G3000 SWXL, Tosohaas) after 7 min and is detected at 278 nm only. FIG. 31 shows chromatograms of size exclusion chromatography of FA standard profile at 490 nm. In contrast with free FA, which is eluted from the column in a distinctive peak, DOX is not eluted in a distinctive peak (FIG. 29). Although DOX standard curve shows an absorption peak at 477 nm, this is in reality not available for detection. DOX/SP1 ratio can be determined from their standard curves in solution.

Figure 10:
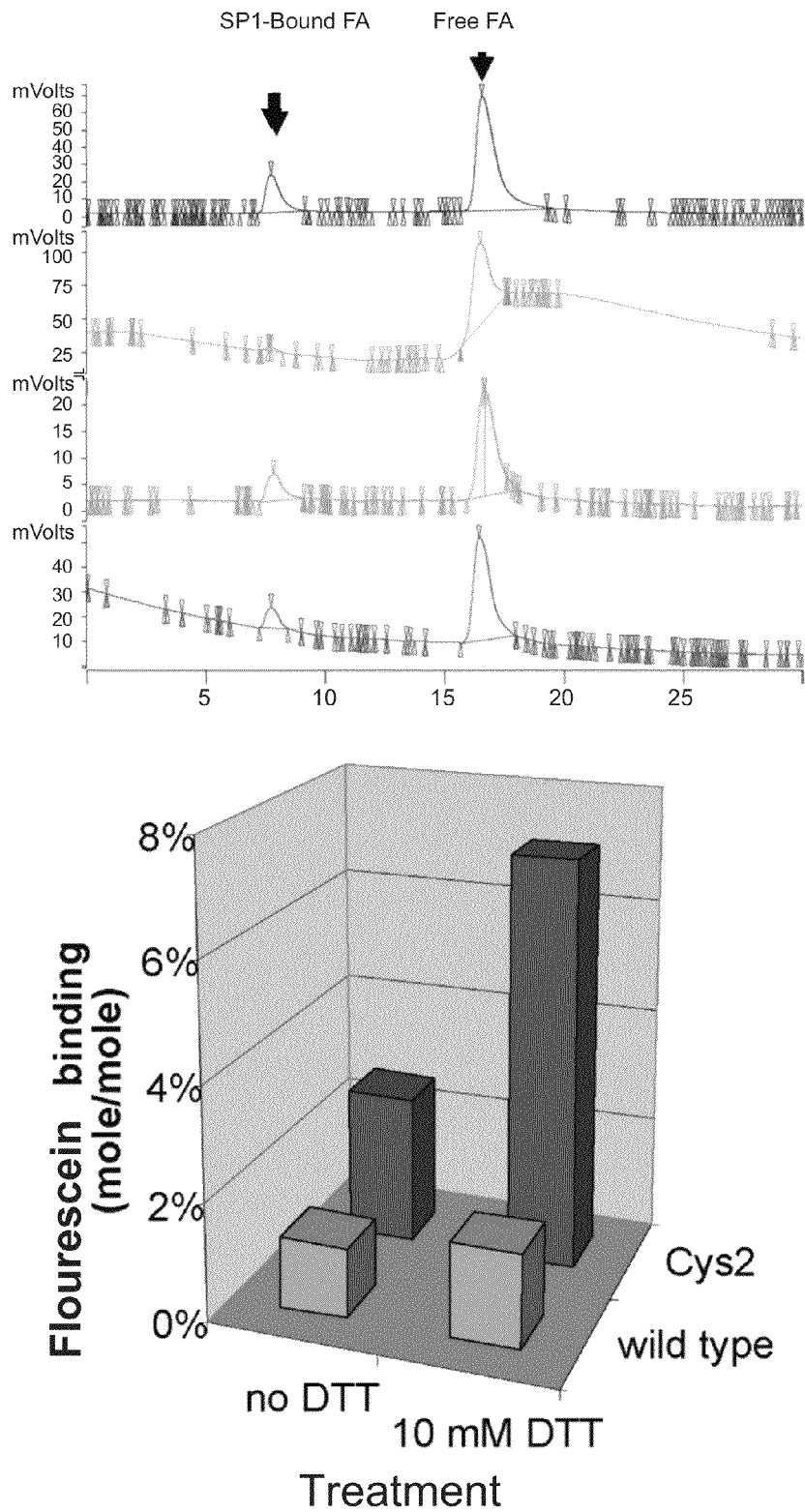
Figure 11:
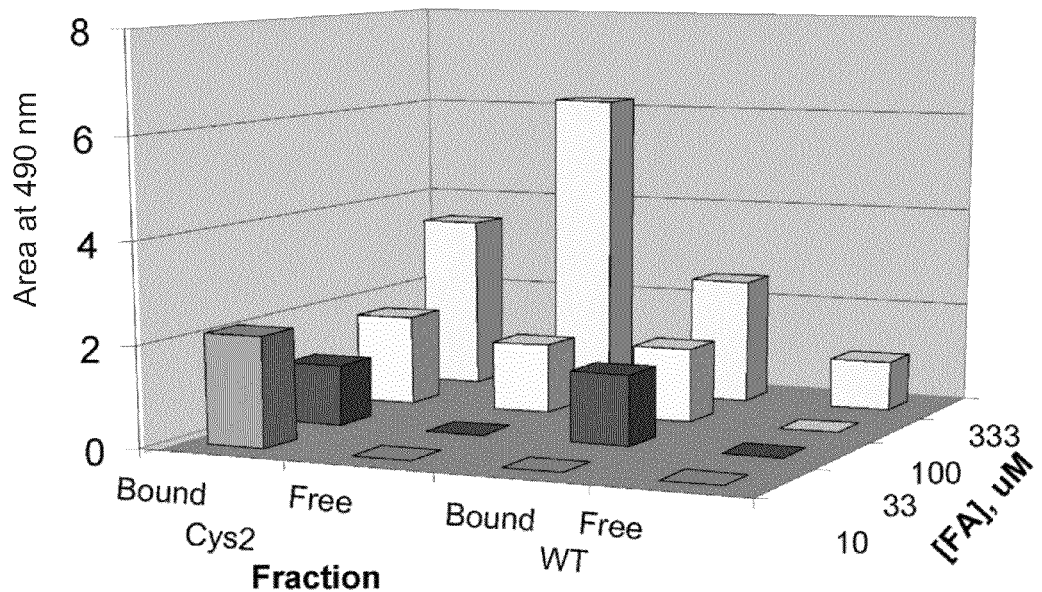
Figure 12:
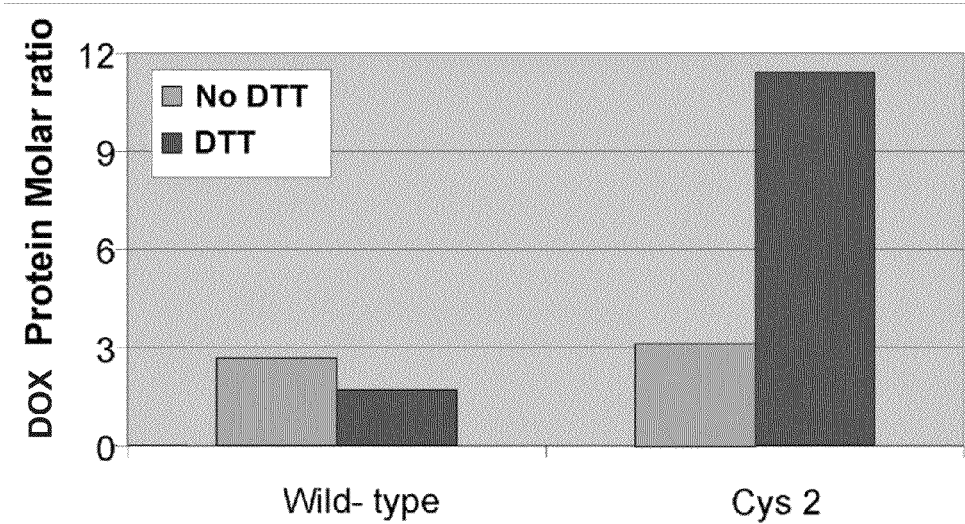
Figure 13:
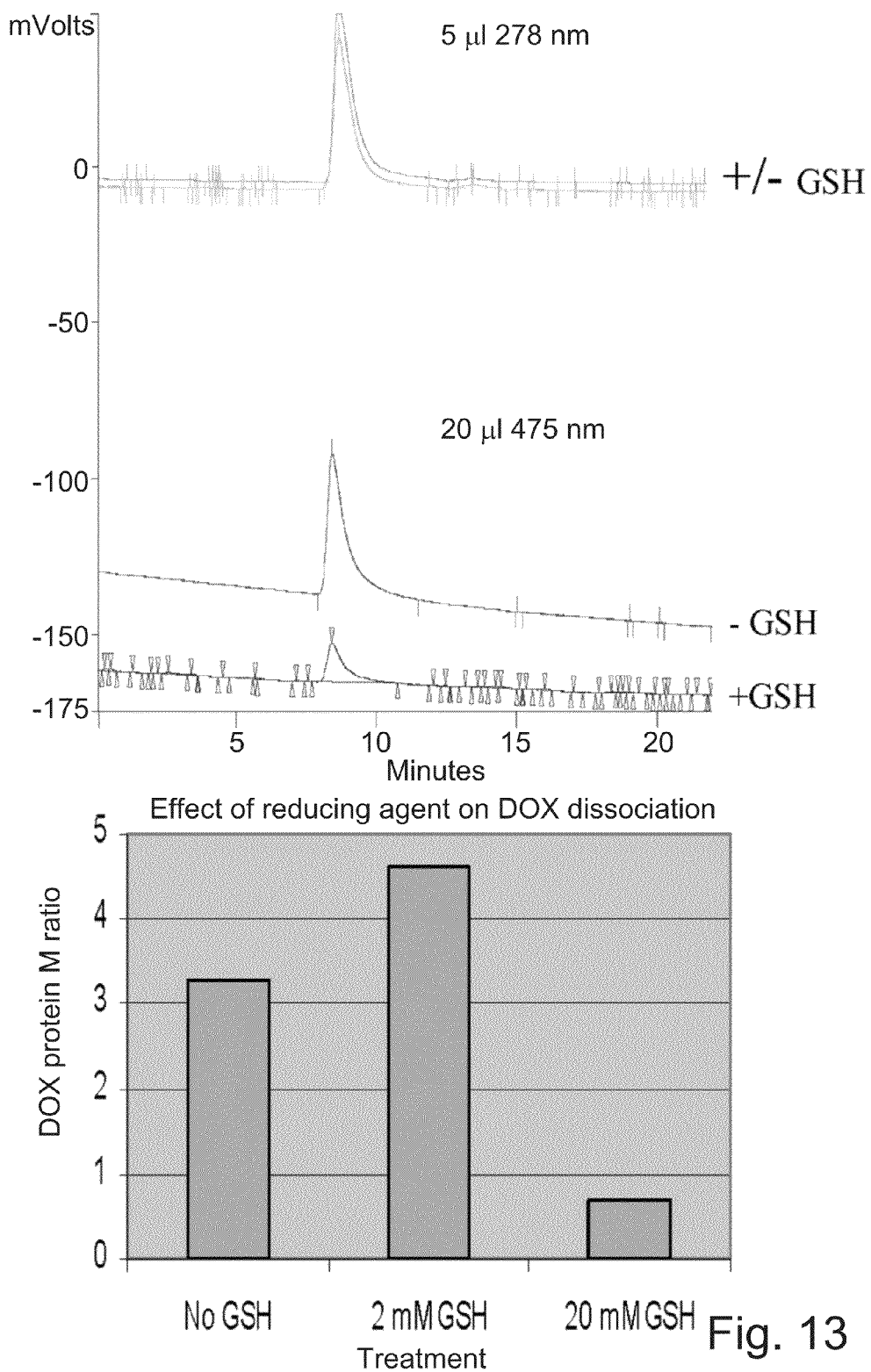
Figure 15:
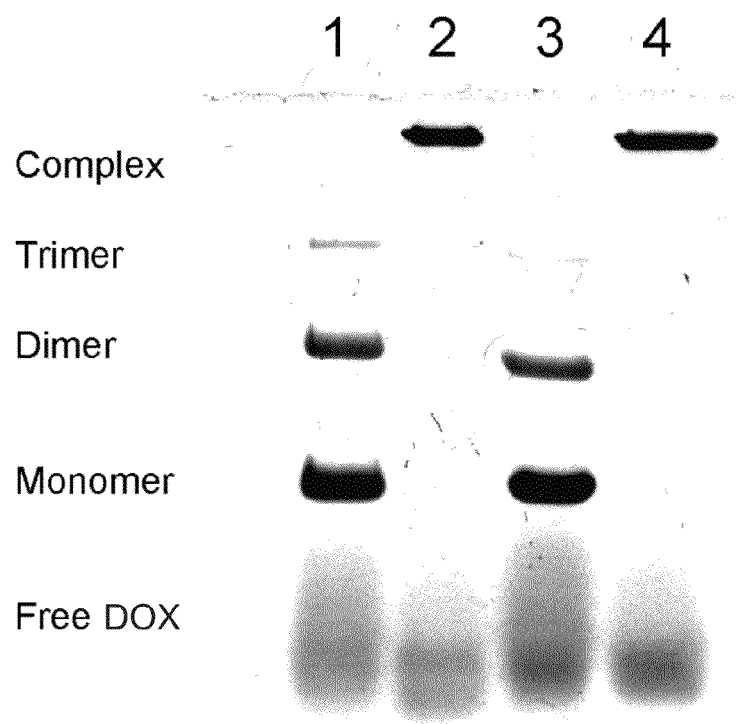
Figure 17:
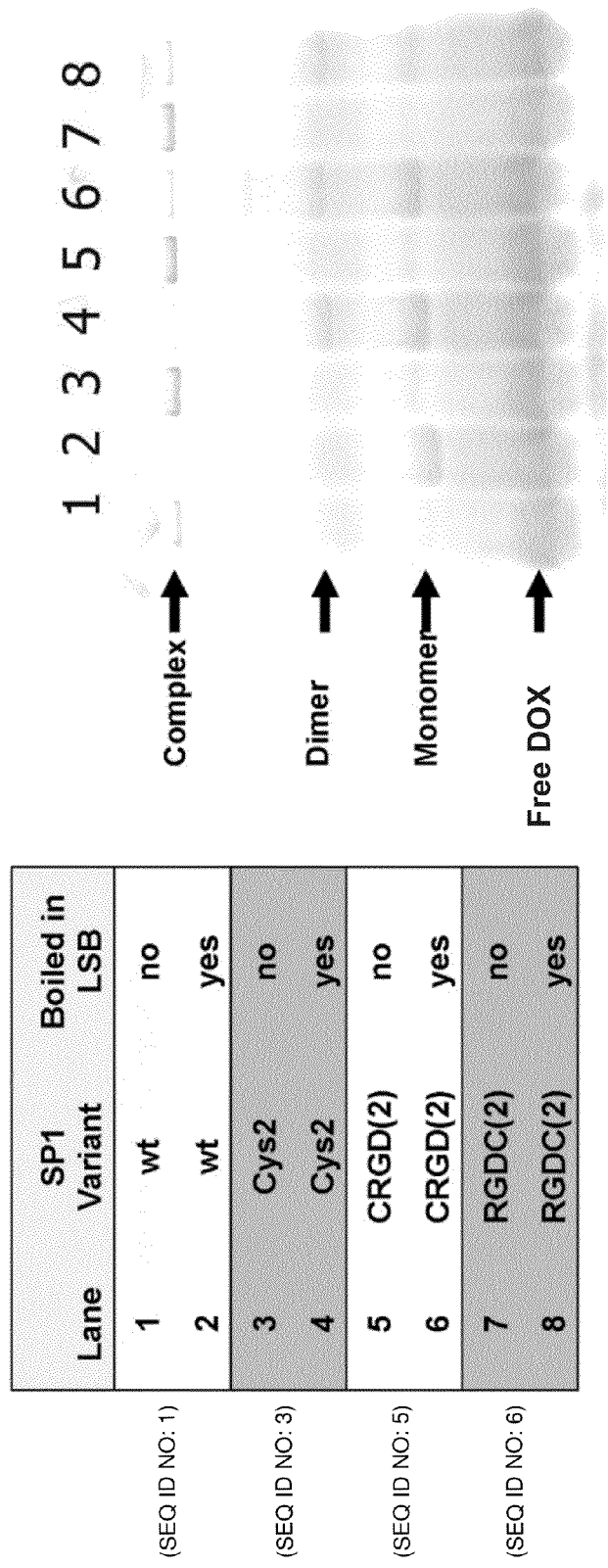
Figure 33:
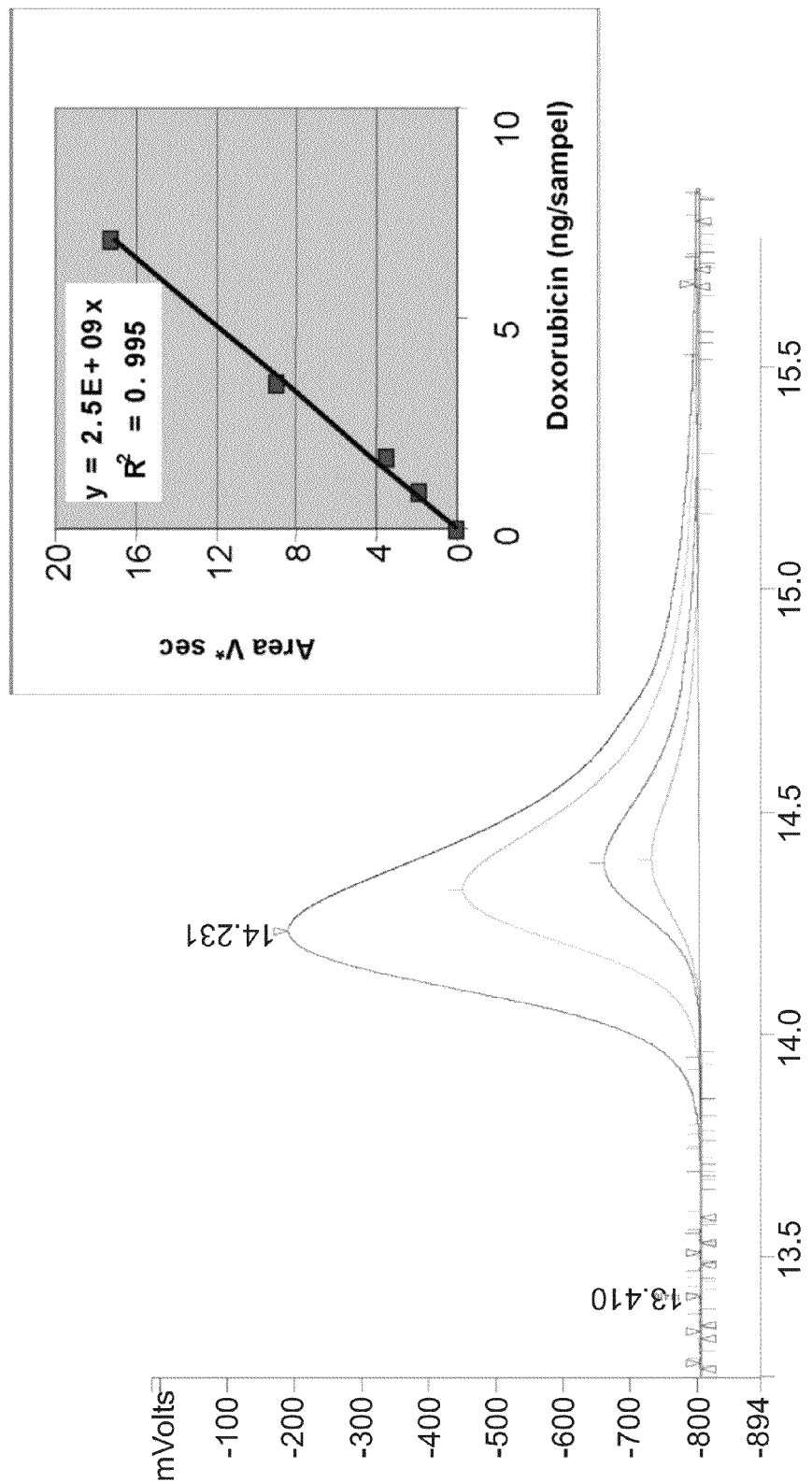
FIG. 33 shows the standard profile of DOX (determined at 477 nm) on RP-HPLC. Inset show the quantitative detection of the DOX over a range of concentrations.
Figure 34:
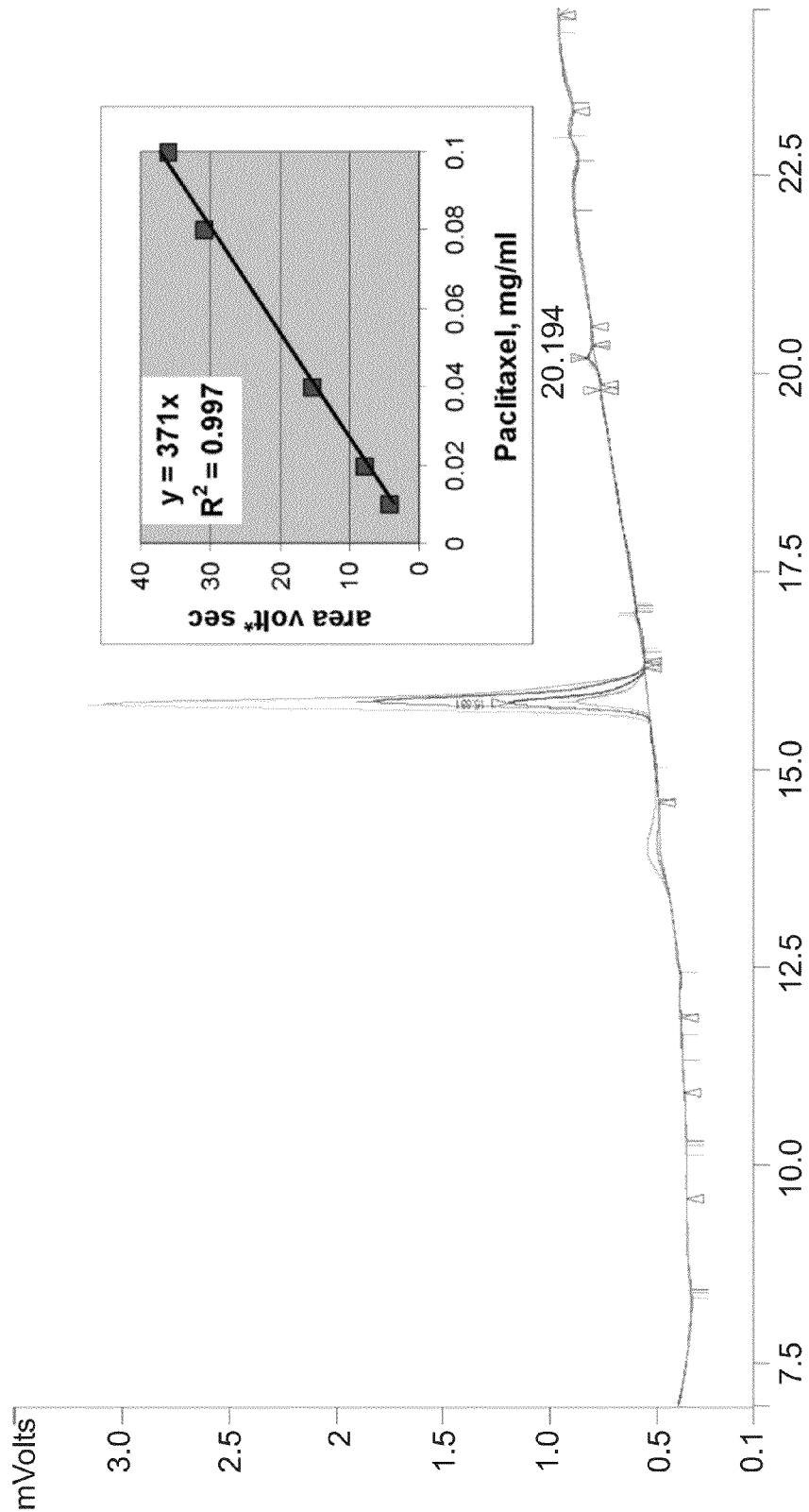
FIG. 34 shows the standard profile for PTX (determined at 225 nm) on RP-HPLC. Inset show the quantitative detection of the PTX over a range of concentrations.

Reverse phase HPLC (RP-HPLC) analysis also separates between free ligand and SP1 (see FIGS. 10, 11, 13). This method was used to test complexing of Doxorubicin and the water insoluble drug Paclitaxel (PTX). In this case both complexed compounds bound to the resin (C-18) and were eluted at different acetonitrile concentrations. FIG. 32 shows the standard profiles of Cys2 SP1 (determined at both 278 and 225 nm). FIG. 33 shows the standard profile of DOX (determined at 477 nm). FIG. 34 shows the standard profile for PTX (determined at 225 nm).

Similar to the results using size exclusion chromatography the SP1-DOX complexes also eluted at the same time as unloaded SP1 and are detected also at 477 nm, as well as 278 nm. Quantification of SP1-bound DOX as well as free DOX can be directly calculated from the absorbance in their peaks at 477 nm because uncomplexed SP1 does not absorb light at this wave length. Estimation of the amount of protein in the SP1-DOX peak, at 278 nm can corrected for DOX absorption at 278 nm according to the following equation (OD278-0.77*$OD_{477}$). In contrast to FA and DOX, PTX does not display unique absorption properties and complexed PTX cannot be detected. Apparently PTX dissociates from the SP1-PTX complex in the presence of high acetonitrile concentrations and it can be detected in the same elution as free PTX.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An isolated composition of matter comprising a therapeutic agent non-covalently complexed with an oligomer of stable protein 1 (SP1) polypeptides,
wherein the SP1 polypeptide consists of an amino acid sequence at least 95% identical to SEQ ID NO: 1 having: (i) a mobile N-terminal tail located N-terminally to the B3 domain of said SP1 polypeptide and (ii) one amino acid of said mobile N-terminal tail having a cysteine residue, and wherein said SP1 polypeptide is a boiling and detergent stable protein, forms stable SP 1 dimers, and forms redox-dependent dimers.

2. The isolated composition of matter of claim 1, wherein said SP1 polypeptide of claim 1, consists of the amino acid sequence as set forth in SEQ ID NO: 3.

3. The isolated composition of matter of claim 1, wherein said non-covalent complex is a reversible complex.

4. The isolated composition of matter of claim 1, wherein said therapeutic agent non-covalently complexed with said oligomer of SP1 polypeptide is an anticancer drug.

5. The composition of matter of claim 1, wherein the SP1 polypeptides are heat stable and protease resistant.

6. The isolated composition of matter of claim 1, wherein said non-covalent complex between said therapeutic agent and the oligomer of SP1 polypeptides is redox-dependent.

7. The isolated composition of matter of claim 1, wherein said mobile N-terminal tail has the peptide CRGD (SEQ ID NO: 151) which is a target recognition sequence.

8. The isolated composition of matter of claim 1, wherein said mobile N-terminal tail has a cancer cell surface or cancer cell vasculature recognition sequence comprising the peptide CRGD (SEQ ID NO: 151) target recognition sequence.

9. The isolated composition of matter of claim 8, wherein said mobile N-terminal tail has a cancer cell vasculature recognition sequence selected from the group consisting of SEQ ID NO: 63-80 and 81.

10. The isolated composition of matter of claim 1, wherein said mobile N-terminal tail has a cancer cell surface recognition sequence selected from the group consisting of SEQ ID NO: 31-61 and 62.

11. The isolated composition of matter of claim 1, wherein said mobile N-terminal tail has the peptide RGDC (SEQ ID NO: 152) which is a target recognition sequence N-terminally to said B3 domain.

12. The isolated composition of matter of claim 1, wherein said therapeutic agent is selected from the group consisting of doxorubicin, paclitaxel, and fluorescene amine.

13. The isolated composition of matter of claim 1, wherein said therapeutic agent is non-covalently complexed with said oligomer of SP1 polypeptides under oxidizing conditions and is released from said complex under reducing conditions.

14. The isolated composition of matter of claim 1, wherein said non-covalent complex is redox dependent and said agent is a chemotherapeutic agent.

15. The isolated composition of matter of claim 14, wherein said non-covalent complex formation is redox dependent and said agent is doxorubicin or paclitaxel.

16. The isolated composition of matter of claim 1, wherein said oligomer of SP1 polypeptides is in a stable homo-oligomeric complex conformation.

17. The isolated SP1 polypeptide of claim 1, wherein said SP1 polypeptide consist of the amino acid sequence set forth in any one of SEQ ID NO: 5, 6 or 9.

18. A method of delivering a therapeutic agent to a subject in need thereof, the method comprising administering to the subject a therapeutically effective amount of the isolated composition of matter of claim 1 to said subject, thereby delivering said therapeutic agent to said subject.

19. The method of delivering a therapeutic agent to a subject in need thereof according to claim 18, wherein said therapeutic agent is a diagnostic and/or a cosmetic agent, thereby delivering said diagnostic and/or cosmetic agent to said subject.

20. A method of stabilizing a therapeutic agent with SP1 polypeptides, the method comprising contacting a therapeutic agent with an oligomer of SP1 polypeptides, and producing the isolated composition of matter of claim 1, thereby stabilizing the therapeutic agent with SP1 polypeptides.

21. The method of claim 20, further comprising the step of contacting the isolated composition of claim 1 with a solvent, so as to form a solution thereof.

22. The method of claim 20, wherein the isolated composition of claim 1 comprises a stability property selected from the group consisting of temperature stability, ionic strength stability, protease stability and catalytic stability.

23. A method of enhancing the solubility of a therapeutic agent with an oligomer of SP1 polypeptides in a solution, the method comprising:
dissolving said isolated composition of matter of claim 1 with a solvent so as to form a solution; thereby enhancing the solubility of the isolated composition of matter of claim 1 in the solution.

24. The method of claim 23, wherein said solvent is an aqueous or organic solvent.

* * * * *

SEQUENCE LISTING

```
<160> NUMBER OF SEQ ID NOS: 152

<210> SEQ ID NO 1
<211> LENGTH: 108
<212> TYPE: PRT
<213> ORGANISM: Populus tremula
<220> FEATURE:
<221> NAME/KEY: misc_feature
<223> OTHER INFORMATION: Wild type Sp1 polypeptide

<400> SEQUENCE: 1

Met Ala Thr Arg Thr Pro Lys Leu Val Lys His Thr Leu Leu Thr Arg
1               5                   10                  15

Phe Lys Asp Glu Ile Thr Arg Glu Gln Ile Asp Asn Tyr Ile Asn Asp
            20                  25                  30

Tyr Thr Asn Leu Leu Asp Leu Ile Pro Ser Met Lys Ser Phe Asn Trp
        35                  40                  45

Gly Thr Asp Leu Gly Met Glu Ser Ala Glu Leu Asn Arg Gly Tyr Thr
    50                  55                  60

His Ala Phe Glu Ser Thr Phe Glu Ser Lys Ser Gly Leu Gln Glu Tyr
65                  70                  75                  80

Leu Asp Ser Ala Ala Leu Ala Ala Phe Ala Glu Gly Phe Leu Pro Thr
                85                  90                  95

Leu Ser Gln Arg Leu Val Ile Asp Tyr Phe Leu Tyr
            100                 105

<210> SEQ ID NO 2
<211> LENGTH: 103
<212> TYPE: PRT
<213> ORGANISM: Artificial sequence
<220> FEATURE:
<223> OTHER INFORMATION: Sp1 mutant variant: amino acid 2-6 deleted

<400> SEQUENCE: 2

Met Lys Leu Val Lys His Thr Leu Leu Thr Arg Phe Lys Asp Glu Ile
1               5                   10                  15

Thr Arg Glu Gln Ile Asp Asn Tyr Ile Asn Asp Tyr Thr Asn Leu Leu
            20                  25                  30

Asp Leu Ile Pro Ser Met Lys Ser Phe Asn Trp Gly Thr Asp Leu Gly
        35                  40                  45
```

```
Met Glu Ser Ala Glu Leu Asn Arg Gly Tyr Thr His Ala Phe Glu Ser
 50                  55                  60
Thr Phe Glu Ser Lys Ser Gly Leu Gln Glu Tyr Leu Asp Ser Ala Ala
 65                  70                  75                  80
Leu Ala Ala Phe Ala Glu Gly Phe Leu Pro Thr Leu Ser Gln Arg Leu
                 85                  90                  95
Val Ile Asp Tyr Phe Leu Tyr
            100
```

```
<210> SEQ ID NO 3
<211> LENGTH: 109
<212> TYPE: PRT
<213> ORGANISM: Artificial sequence
<220> FEATURE:
<223> OTHER INFORMATION: Sp1 mutant variant: Cys in position 2

<400> SEQUENCE: 3
```

```
Met Cys Ala Thr Arg Thr Pro Lys Leu Val Lys His Thr Leu Leu Thr
 1               5                  10                  15
Arg Phe Lys Asp Glu Ile Thr Arg Glu Gln Ile Asp Asn Tyr Ile Asn
                 20                  25                  30
Asp Tyr Thr Asn Leu Leu Asp Leu Ile Pro Ser Met Lys Ser Phe Asn
                 35                  40                  45
Trp Gly Thr Asp Leu Gly Met Glu Ser Ala Glu Leu Asn Arg Gly Tyr
 50                  55                  60
Thr His Ala Phe Glu Ser Thr Phe Glu Ser Lys Ser Gly Leu Gln Glu
 65                  70                  75                  80
Tyr Leu Asp Ser Ala Ala Leu Ala Ala Phe Ala Glu Gly Phe Leu Pro
                 85                  90                  95
Thr Leu Ser Gln Arg Leu Val Ile Asp Tyr Phe Leu Tyr
            100                 105
```

```
<210> SEQ ID NO 4
<211> LENGTH: 110
<212> TYPE: PRT
<213> ORGANISM: Artificial sequence
<220> FEATURE:
<223> OTHER INFORMATION: Sp1 mutant variant: 2X His inserted into
      position 2

<400> SEQUENCE: 4
```

```
Met His His Ala Thr Arg Thr Pro Lys Leu Val Lys His Thr Leu Leu
 1               5                  10                  15
Thr Arg Phe Lys Asp Glu Ile Thr Arg Glu Gln Ile Asp Asn Tyr Ile
                 20                  25                  30
Asn Asp Tyr Thr Asn Leu Leu Asp Leu Ile Pro Ser Met Lys Ser Phe
                 35                  40                  45
Asn Trp Gly Thr Asp Leu Gly Met Glu Ser Ala Glu Leu Asn Arg Gly
 50                  55                  60
Tyr Thr His Ala Phe Glu Ser Thr Phe Glu Ser Lys Ser Gly Leu Gln
 65                  70                  75                  80
Glu Tyr Leu Asp Ser Ala Ala Leu Ala Ala Phe Ala Glu Gly Phe Leu
                 85                  90                  95
Pro Thr Leu Ser Gln Arg Leu Val Ile Asp Tyr Phe Leu Tyr
            100                 105                 110
```

```
<210> SEQ ID NO 5
<211> LENGTH: 112
<212> TYPE: PRT
```

<213> ORGANISM: Artificial sequence
<220> FEATURE:
<223> OTHER INFORMATION: Sp1 mutant variant: Cys, Arg, Gly and Asp
      inserted into position 2

<400> SEQUENCE: 5

Met Cys Arg Gly Asp Ala Thr Arg Thr Pro Lys Leu Val Lys His Thr
1               5                   10                  15

Leu Leu Thr Arg Phe Lys Asp Glu Ile Thr Arg Glu Gln Ile Asp Asn
            20                  25                  30

Tyr Ile Asn Asp Tyr Thr Asn Leu Leu Asp Leu Ile Pro Ser Met Lys
        35                  40                  45

Ser Phe Asn Trp Gly Thr Asp Leu Gly Met Glu Ser Ala Glu Leu Asn
50                  55                  60

Arg Gly Tyr Thr His Ala Phe Glu Ser Thr Phe Glu Ser Lys Ser Gly
65                  70                  75                  80

Leu Gln Glu Tyr Leu Asp Ser Ala Ala Leu Ala Ala Phe Ala Glu Gly
                85                  90                  95

Phe Leu Pro Thr Leu Ser Gln Arg Leu Val Ile Asp Tyr Phe Leu Tyr
            100                 105                 110

<210> SEQ ID NO 6
<211> LENGTH: 112
<212> TYPE: PRT
<213> ORGANISM: Artificial sequence
<220> FEATURE:
<223> OTHER INFORMATION: Sp1 mutant variant: Arg, Gly, Asp and Cys
      inserted into position 2

<400> SEQUENCE: 6

Met Arg Gly Asp Cys Ala Thr Arg Thr Pro Lys Leu Val Lys His Thr
1               5                   10                  15

Leu Leu Thr Arg Phe Lys Asp Glu Ile Thr Arg Glu Gln Ile Asp Asn
            20                  25                  30

Tyr Ile Asn Asp Tyr Thr Asn Leu Leu Asp Leu Ile Pro Ser Met Lys
        35                  40                  45

Ser Phe Asn Trp Gly Thr Asp Leu Gly Met Glu Ser Ala Glu Leu Asn
50                  55                  60

Arg Gly Tyr Thr His Ala Phe Glu Ser Thr Phe Glu Ser Lys Ser Gly
65                  70                  75                  80

Leu Gln Glu Tyr Leu Asp Ser Ala Ala Leu Ala Ala Phe Ala Glu Gly
                85                  90                  95

Phe Leu Pro Thr Leu Ser Gln Arg Leu Val Ile Asp Tyr Phe Leu Tyr
            100                 105                 110

<210> SEQ ID NO 7
<211> LENGTH: 114
<212> TYPE: PRT
<213> ORGANISM: Artificial sequence
<220> FEATURE:
<223> OTHER INFORMATION: Sp1 mutant variant: 6X His inserted into
      position 2

<400> SEQUENCE: 7

Met His His His His His His Ala Thr Arg Thr Pro Lys Leu Val Lys
1               5                   10                  15

His Thr Leu Leu Thr Arg Phe Lys Asp Glu Ile Thr Arg Glu Gln Ile
            20                  25                  30

Asp Asn Tyr Ile Asn Asp Tyr Thr Asn Leu Leu Asp Leu Ile Pro Ser
        35                  40                  45

```
Met Lys Ser Phe Asn Trp Gly Thr Asp Leu Gly Met Glu Ser Ala Glu
     50                  55                  60

Leu Asn Arg Gly Tyr Thr His Ala Phe Glu Ser Thr Phe Glu Ser Lys
 65                  70                  75                  80

Ser Gly Leu Gln Glu Tyr Leu Asp Ser Ala Ala Leu Ala Ala Phe Ala
                 85                  90                  95

Glu Gly Phe Leu Pro Thr Leu Ser Gln Arg Leu Val Ile Asp Tyr Phe
                100                 105                 110

Leu Tyr

<210> SEQ ID NO 8
<211> LENGTH: 104
<212> TYPE: PRT
<213> ORGANISM: Artificial sequence
<220> FEATURE:
<223> OTHER INFORMATION: Sp1 mutant variant: His inserted into position
      2 together with a deletion of amino acid 2-6

<400> SEQUENCE: 8

Met His Lys Leu Val Lys His Thr Leu Leu Thr Arg Phe Lys Asp Glu
 1               5                  10                  15

Ile Thr Arg Glu Gln Ile Asp Asn Tyr Ile Asn Asp Tyr Thr Asn Leu
                 20                  25                  30

Leu Asp Leu Ile Pro Ser Met Lys Ser Phe Asn Trp Gly Thr Asp Leu
                 35                  40                  45

Gly Met Glu Ser Ala Glu Leu Asn Arg Gly Tyr Thr His Ala Phe Glu
     50                  55                  60

Ser Thr Phe Glu Ser Lys Ser Gly Leu Gln Glu Tyr Leu Asp Ser Ala
 65                  70                  75                  80

Ala Leu Ala Ala Phe Ala Glu Gly Phe Leu Pro Thr Leu Ser Gln Arg
                 85                  90                  95

Leu Val Ile Asp Tyr Phe Leu Tyr
                100

<210> SEQ ID NO 9
<211> LENGTH: 103
<212> TYPE: PRT
<213> ORGANISM: Artificial sequence
<220> FEATURE:
<223> OTHER INFORMATION: Sp1 mutant variant: Cys inserted into position
      2 together with a deletion of amino acid 2-7

<400> SEQUENCE: 9

Met Cys Leu Val Lys His Thr Leu Leu Thr Arg Phe Lys Asp Glu Ile
 1               5                  10                  15

Thr Arg Glu Gln Ile Asp Asn Tyr Ile Asn Asp Tyr Thr Asn Leu Leu
                 20                  25                  30

Asp Leu Ile Pro Ser Met Lys Ser Phe Asn Trp Gly Thr Asp Leu Gly
                 35                  40                  45

Met Glu Ser Ala Glu Leu Asn Arg Gly Tyr Thr His Ala Phe Glu Ser
     50                  55                  60

Thr Phe Glu Ser Lys Ser Gly Leu Gln Glu Tyr Leu Asp Ser Ala Ala
 65                  70                  75                  80

Leu Ala Ala Phe Ala Glu Gly Phe Leu Pro Thr Leu Ser Gln Arg Leu
                 85                  90                  95

Val Ile Asp Tyr Phe Leu Tyr
                100
```

```
<210> SEQ ID NO 10
<211> LENGTH: 108
<212> TYPE: PRT
<213> ORGANISM: Artificial sequence
<220> FEATURE:
<223> OTHER INFORMATION: Sp1 mutant variant: E20K modified loop1

<400> SEQUENCE: 10

Met Ala Thr Arg Thr Pro Lys Leu Val Lys His Thr Leu Leu Thr Arg
1               5                   10                  15

Phe Lys Asp Lys Ile Thr Arg Glu Gln Ile Asp Asn Tyr Ile Asn Asp
                20                  25                  30

Tyr Thr Asn Leu Leu Asp Leu Ile Pro Ser Met Lys Ser Phe Asn Trp
            35                  40                  45

Gly Thr Asp Leu Gly Met Glu Ser Ala Glu Leu Asn Arg Gly Tyr Thr
50                  55                  60

His Ala Phe Glu Ser Thr Phe Glu Ser Lys Ser Gly Leu Gln Glu Tyr
65                  70                  75                  80

Leu Asp Ser Ala Ala Leu Ala Ala Phe Ala Glu Gly Phe Leu Pro Thr
                85                  90                  95

Leu Ser Gln Arg Leu Val Ile Asp Tyr Phe Leu Tyr
            100                 105

<210> SEQ ID NO 11
<211> LENGTH: 110
<212> TYPE: PRT
<213> ORGANISM: Artificial sequence
<220> FEATURE:
<223> OTHER INFORMATION: Sp1 mutant variant: Cys inserted into position
      2, K18R mutated and a Gly inserted into position 19

<400> SEQUENCE: 11

Met Cys Ala Thr Arg Thr Pro Lys Leu Val Lys His Thr Leu Leu Thr
1               5                   10                  15

Arg Phe Arg Gly Asp Glu Ile Thr Arg Glu Gln Ile Asp Asn Tyr Ile
                20                  25                  30

Asn Asp Tyr Thr Asn Leu Leu Asp Leu Ile Pro Ser Met Lys Ser Phe
            35                  40                  45

Asn Trp Gly Thr Asp Leu Gly Met Glu Ser Ala Glu Leu Asn Arg Gly
50                  55                  60

Tyr Thr His Ala Phe Glu Ser Thr Phe Glu Ser Lys Ser Gly Leu Gln
65                  70                  75                  80

Glu Tyr Leu Asp Ser Ala Ala Leu Ala Ala Phe Ala Glu Gly Phe Leu
                85                  90                  95

Pro Thr Leu Ser Gln Arg Leu Val Ile Asp Tyr Phe Leu Tyr
            100                 105                 110

<210> SEQ ID NO 12
<211> LENGTH: 108
<212> TYPE: PRT
<213> ORGANISM: Artificial sequence
<220> FEATURE:
<223> OTHER INFORMATION: Sp1 mutant variant: R23A mutated

<400> SEQUENCE: 12

Met Ala Thr Arg Thr Pro Lys Leu Val Lys His Thr Leu Leu Thr Arg
1               5                   10                  15

Phe Lys Asp Glu Ile Thr Ala Glu Gln Ile Asp Asn Tyr Ile Asn Asp
                20                  25                  30
```

```
Tyr Thr Asn Leu Leu Asp Leu Ile Pro Ser Met Lys Ser Phe Asn Trp
            35                  40                  45

Gly Thr Asp Leu Gly Met Glu Ser Ala Glu Leu Asn Arg Gly Tyr Thr
 50                  55                  60

His Ala Phe Glu Ser Thr Phe Glu Ser Lys Ser Gly Leu Gln Glu Tyr
 65                  70                  75                  80

Leu Asp Ser Ala Ala Leu Ala Ala Phe Ala Glu Gly Phe Leu Pro Thr
                 85                  90                  95

Leu Ser Gln Arg Leu Val Ile Asp Tyr Phe Leu Tyr
               100                 105

<210> SEQ ID NO 13
<211> LENGTH: 108
<212> TYPE: PRT
<213> ORGANISM: Artificial sequence
<220> FEATURE:
<223> OTHER INFORMATION: Sp1 mutant variant: D27A mutated

<400> SEQUENCE: 13

Met Ala Thr Arg Thr Pro Lys Leu Val Lys His Thr Leu Leu Thr Arg
 1               5                  10                  15

Phe Lys Asp Glu Ile Thr Arg Glu Gln Ile Ala Asn Tyr Ile Asn Asp
                20                  25                  30

Tyr Thr Asn Leu Leu Asp Leu Ile Pro Ser Met Lys Ser Phe Asn Trp
            35                  40                  45

Gly Thr Asp Leu Gly Met Glu Ser Ala Glu Leu Asn Arg Gly Tyr Thr
 50                  55                  60

His Ala Phe Glu Ser Thr Phe Glu Ser Lys Ser Gly Leu Gln Glu Tyr
 65                  70                  75                  80

Leu Asp Ser Ala Ala Leu Ala Ala Phe Ala Glu Gly Phe Leu Pro Thr
                 85                  90                  95

Leu Ser Gln Arg Leu Val Ile Asp Tyr Phe Leu Tyr
               100                 105

<210> SEQ ID NO 14
<211> LENGTH: 108
<212> TYPE: PRT
<213> ORGANISM: Artificial sequence
<220> FEATURE:
<223> OTHER INFORMATION: Sp1 mutant variant: I30A mutated

<400> SEQUENCE: 14

Met Ala Thr Arg Thr Pro Lys Leu Val Lys His Thr Leu Leu Thr Arg
 1               5                  10                  15

Phe Lys Asp Glu Ile Thr Arg Glu Gln Ile Asp Asn Tyr Ala Asn Asp
                20                  25                  30

Tyr Thr Asn Leu Leu Asp Leu Ile Pro Ser Met Lys Ser Phe Asn Trp
            35                  40                  45

Gly Thr Asp Leu Gly Met Glu Ser Ala Glu Leu Asn Arg Gly Tyr Thr
 50                  55                  60

His Ala Phe Glu Ser Thr Phe Glu Ser Lys Ser Gly Leu Gln Glu Tyr
 65                  70                  75                  80

Leu Asp Ser Ala Ala Leu Ala Ala Phe Ala Glu Gly Phe Leu Pro Thr
                 85                  90                  95

Leu Ser Gln Arg Leu Val Ile Asp Tyr Phe Leu Tyr
               100                 105

<210> SEQ ID NO 15
```

<211> LENGTH: 108
<212> TYPE: PRT
<213> ORGANISM: Artificial sequence
<220> FEATURE:
<223> OTHER INFORMATION: Sp1 mutant variant: N31A mutated

<400> SEQUENCE: 15

```
Met Ala Thr Arg Thr Pro Lys Leu Val Lys His Thr Leu Leu Thr Arg
1               5                   10                  15

Phe Lys Asp Glu Ile Thr Arg Glu Gln Ile Asp Asn Tyr Ile Ala Asp
            20                  25                  30

Tyr Thr Asn Leu Leu Asp Leu Ile Pro Ser Met Lys Ser Phe Asn Trp
        35                  40                  45

Gly Thr Asp Leu Gly Met Glu Ser Ala Glu Leu Asn Arg Gly Tyr Thr
    50                  55                  60

His Ala Phe Glu Ser Thr Phe Glu Ser Lys Ser Gly Leu Gln Glu Tyr
65                  70                  75                  80

Leu Asp Ser Ala Ala Leu Ala Ala Phe Ala Glu Gly Phe Leu Pro Thr
                85                  90                  95

Leu Ser Gln Arg Leu Val Ile Asp Tyr Phe Leu Tyr
            100                 105
```

<210> SEQ ID NO 16
<211> LENGTH: 108
<212> TYPE: PRT
<213> ORGANISM: Artificial sequence
<220> FEATURE:
<223> OTHER INFORMATION: Sp1 mutant variant: T34A mutated

<400> SEQUENCE: 16

```
Met Ala Thr Arg Thr Pro Lys Leu Val Lys His Thr Leu Leu Thr Arg
1               5                   10                  15

Phe Lys Asp Glu Ile Thr Arg Glu Gln Ile Asp Asn Tyr Ile Asn Asp
            20                  25                  30

Tyr Ala Asn Leu Leu Asp Leu Ile Pro Ser Met Lys Ser Phe Asn Trp
        35                  40                  45

Gly Thr Asp Leu Gly Met Glu Ser Ala Glu Leu Asn Arg Gly Tyr Thr
    50                  55                  60

His Ala Phe Glu Ser Thr Phe Glu Ser Lys Ser Gly Leu Gln Glu Tyr
65                  70                  75                  80

Leu Asp Ser Ala Ala Leu Ala Ala Phe Ala Glu Gly Phe Leu Pro Thr
                85                  90                  95

Leu Ser Gln Arg Leu Val Ile Asp Tyr Phe Leu Tyr
            100                 105
```

<210> SEQ ID NO 17
<211> LENGTH: 108
<212> TYPE: PRT
<213> ORGANISM: Artificial sequence
<220> FEATURE:
<223> OTHER INFORMATION: Sp1 mutant variant: D38A mutated

<400> SEQUENCE: 17

```
Met Ala Thr Arg Thr Pro Lys Leu Val Lys His Thr Leu Leu Thr Arg
1               5                   10                  15

Phe Lys Asp Glu Ile Thr Arg Glu Gln Ile Asp Asn Tyr Ile Asn Asp
            20                  25                  30

Tyr Thr Asn Leu Leu Ala Leu Ile Pro Ser Met Lys Ser Phe Asn Trp
        35                  40                  45
```

```
Gly Thr Asp Leu Gly Met Glu Ser Ala Glu Leu Asn Arg Gly Tyr Thr
    50                  55                  60

His Ala Phe Glu Ser Thr Phe Glu Ser Lys Ser Gly Leu Gln Glu Tyr
 65                  70                  75                  80

Leu Asp Ser Ala Ala Leu Ala Ala Phe Ala Glu Gly Phe Leu Pro Thr
                 85                  90                  95

Leu Ser Gln Arg Leu Val Ile Asp Tyr Phe Leu Tyr
            100                 105
```

<210> SEQ ID NO 18
<211> LENGTH: 103
<212> TYPE: PRT
<213> ORGANISM: Artificial sequence
<220> FEATURE:
<223> OTHER INFORMATION: Sp1 mutant variant: amino acids 2-6 deleted and I40C mutated

<400> SEQUENCE: 18

```
Met Lys Leu Val Lys His Thr Leu Leu Thr Arg Phe Lys Asp Glu Ile
 1               5                  10                  15

Thr Arg Glu Gln Ile Asp Asn Tyr Ile Asn Asp Tyr Thr Asn Leu Leu
                20                  25                  30

Asp Leu Cys Pro Ser Met Lys Ser Phe Asn Trp Gly Thr Asp Leu Gly
            35                  40                  45

Met Glu Ser Ala Glu Leu Asn Arg Gly Tyr Thr His Ala Phe Glu Ser
 50                  55                  60

Thr Phe Glu Ser Lys Ser Gly Leu Gln Glu Tyr Leu Asp Ser Ala Ala
 65                  70                  75                  80

Leu Ala Ala Phe Ala Glu Gly Phe Leu Pro Thr Leu Ser Gln Arg Leu
                 85                  90                  95

Val Ile Asp Tyr Phe Leu Tyr
            100
```

<210> SEQ ID NO 19
<211> LENGTH: 108
<212> TYPE: PRT
<213> ORGANISM: Artificial sequence
<220> FEATURE:
<223> OTHER INFORMATION: Sp1 mutant variant: E68A mutated

<400> SEQUENCE: 19

```
Met Ala Thr Arg Thr Pro Lys Leu Val Lys His Thr Leu Leu Thr Arg
 1               5                  10                  15

Phe Lys Asp Glu Ile Thr Arg Glu Gln Ile Asp Asn Tyr Ile Asn Asp
                20                  25                  30

Tyr Thr Asn Leu Leu Asp Leu Ile Pro Ser Met Lys Ser Phe Asn Trp
            35                  40                  45

Gly Thr Asp Leu Gly Met Glu Ser Ala Glu Leu Asn Arg Gly Tyr Thr
 50                  55                  60

His Ala Phe Ala Ser Thr Phe Glu Ser Lys Ser Gly Leu Gln Glu Tyr
 65                  70                  75                  80

Leu Asp Ser Ala Ala Leu Ala Ala Phe Ala Glu Gly Phe Leu Pro Thr
                 85                  90                  95

Leu Ser Gln Arg Leu Val Ile Asp Tyr Phe Leu Tyr
            100                 105
```

<210> SEQ ID NO 20
<211> LENGTH: 103
<212> TYPE: PRT

-continued

<210> SEQ ID NO 20
<211> LENGTH: 103
<212> TYPE: PRT
<213> ORGANISM: Artificial sequence
<220> FEATURE:
<223> OTHER INFORMATION: Sp1 mutant variant: amino acids 2-6 deleted
      and E72C mutated

<400> SEQUENCE: 20

Met Lys Leu Val Lys His Thr Leu Leu Thr Arg Phe Lys Asp Glu Ile
1               5                   10                  15

Thr Arg Glu Gln Ile Asp Asn Tyr Ile Asn Asp Tyr Thr Asn Leu Leu
            20                  25                  30

Asp Leu Ile Pro Ser Met Lys Ser Phe Asn Trp Gly Thr Asp Leu Gly
        35                  40                  45

Met Glu Ser Ala Glu Leu Asn Arg Gly Tyr Thr His Ala Phe Glu Ser
    50                  55                  60

Thr Phe Cys Ser Lys Ser Gly Leu Gln Glu Tyr Leu Asp Ser Ala Ala
65                  70                  75                  80

Leu Ala Ala Phe Ala Glu Gly Phe Leu Pro Thr Leu Ser Gln Arg Leu
                85                  90                  95

Val Ile Asp Tyr Phe Leu Tyr
            100

<210> SEQ ID NO 21
<211> LENGTH: 103
<212> TYPE: PRT
<213> ORGANISM: Artificial sequence
<220> FEATURE:
<223> OTHER INFORMATION: Sp1 mutant variant: amino acids 2-6 deleted
      and S73C mutated

<400> SEQUENCE: 21

Met Lys Leu Val Lys His Thr Leu Leu Thr Arg Phe Lys Asp Glu Ile
1               5                   10                  15

Thr Arg Glu Gln Ile Asp Asn Tyr Ile Asn Asp Tyr Thr Asn Leu Leu
            20                  25                  30

Asp Leu Ile Pro Ser Met Lys Ser Phe Asn Trp Gly Thr Asp Leu Gly
        35                  40                  45

Met Glu Ser Ala Glu Leu Asn Arg Gly Tyr Thr His Ala Phe Glu Ser
    50                  55                  60

Thr Phe Glu Cys Lys Ser Gly Leu Gln Glu Tyr Leu Asp Ser Ala Ala
65                  70                  75                  80

Leu Ala Ala Phe Ala Glu Gly Phe Leu Pro Thr Leu Ser Gln Arg Leu
                85                  90                  95

Val Ile Asp Tyr Phe Leu Tyr
            100

<210> SEQ ID NO 22
<211> LENGTH: 103
<212> TYPE: PRT
<213> ORGANISM: Artificial sequence
<220> FEATURE:
<223> OTHER INFORMATION: Sp1 mutant variant: amino acids 2-6 deleted
      and L81C mutated

<400> SEQUENCE: 22

Met Lys Leu Val Lys His Thr Leu Leu Thr Arg Phe Lys Asp Glu Ile
1               5                   10                  15

Thr Arg Glu Gln Ile Asp Asn Tyr Ile Asn Asp Tyr Thr Asn Leu Leu
            20                  25                  30

Asp Leu Ile Pro Ser Met Lys Ser Phe Asn Trp Gly Thr Asp Leu Gly
        35                  40                  45

```
Met Glu Ser Ala Glu Leu Asn Arg Gly Tyr Thr His Ala Phe Glu Ser
        50                  55                  60

Thr Phe Glu Ser Lys Ser Gly Leu Gln Glu Tyr Cys Asp Ser Ala Ala
 65                  70                  75                  80

Leu Ala Ala Phe Ala Glu Gly Phe Leu Pro Thr Leu Ser Gln Arg Leu
                 85                  90                  95

Val Ile Asp Tyr Phe Leu Tyr
            100

<210> SEQ ID NO 23
<211> LENGTH: 114
<212> TYPE: PRT
<213> ORGANISM: Artificial sequence
<220> FEATURE:
<223> OTHER INFORMATION: Sp1 mutant variant: 6Xhis inserted into
      position 2 and F106A mutated

<400> SEQUENCE: 23

Met His His His His His His Ala Thr Arg Thr Pro Lys Leu Val Lys
 1               5                  10                  15

His Thr Leu Leu Thr Arg Phe Lys Asp Glu Ile Thr Arg Glu Gln Ile
            20                  25                  30

Asp Asn Tyr Ile Asn Asp Tyr Thr Asn Leu Leu Asp Leu Ile Pro Ser
        35                  40                  45

Met Lys Ser Phe Asn Trp Gly Thr Asp Leu Gly Met Glu Ser Ala Glu
    50                  55                  60

Leu Asn Arg Gly Tyr Thr His Ala Phe Glu Ser Thr Phe Glu Ser Lys
 65                  70                  75                  80

Ser Gly Leu Gln Glu Tyr Leu Asp Ser Ala Ala Leu Ala Ala Phe Ala
                 85                  90                  95

Glu Gly Phe Leu Pro Thr Leu Ser Gln Arg Leu Val Ile Asp Tyr Ala
            100                 105                 110

Leu Tyr

<210> SEQ ID NO 24
<211> LENGTH: 108
<212> TYPE: PRT
<213> ORGANISM: Artificial sequence
<220> FEATURE:
<223> OTHER INFORMATION: Sp1 mutant variant: Y108A mutated

<400> SEQUENCE: 24

Met Ala Thr Arg Thr Pro Lys Leu Val Lys His Thr Leu Leu Thr Arg
 1               5                  10                  15

Phe Lys Asp Glu Ile Thr Arg Glu Gln Ile Asp Asn Tyr Ile Asn Asp
            20                  25                  30

Tyr Thr Asn Leu Leu Asp Leu Ile Pro Ser Met Lys Ser Phe Asn Trp
        35                  40                  45

Gly Thr Asp Leu Gly Met Glu Ser Ala Glu Leu Asn Arg Gly Tyr Thr
    50                  55                  60

His Ala Phe Glu Ser Thr Phe Glu Ser Lys Ser Gly Leu Gln Glu Tyr
 65                  70                  75                  80

Leu Asp Ser Ala Ala Leu Ala Ala Phe Ala Glu Gly Phe Leu Pro Thr
                 85                  90                  95

Leu Ser Gln Arg Leu Val Ile Asp Tyr Phe Leu Ala
            100                 105
```

<210> SEQ ID NO 25
<211> LENGTH: 114
<212> TYPE: PRT
<213> ORGANISM: Artificial sequence
<220> FEATURE:
<223> OTHER INFORMATION: Sp1 mutant variant: 6Xhis inserted into
      position 2, N31A and Y108A mutated

<400> SEQUENCE: 25

Met His His His His His His Ala Thr Arg Thr Pro Lys Leu Val Lys
1               5                   10                  15

His Thr Leu Leu Thr Arg Phe Lys Asp Glu Ile Thr Arg Glu Gln Ile
            20                  25                  30

Asp Asn Tyr Ile Ala Asp Tyr Thr Asn Leu Leu Asp Leu Ile Pro Ser
        35                  40                  45

Met Lys Ser Phe Asn Trp Gly Thr Asp Leu Gly Met Glu Ser Ala Glu
    50                  55                  60

Leu Asn Arg Gly Tyr Thr His Ala Phe Glu Ser Thr Phe Glu Ser Lys
65                  70                  75                  80

Ser Gly Leu Gln Glu Tyr Leu Asp Ser Ala Ala Leu Ala Ala Phe Ala
                85                  90                  95

Glu Gly Phe Leu Pro Thr Leu Ser Gln Arg Leu Val Ile Asp Tyr Phe
            100                 105                 110

Leu Ala

<210> SEQ ID NO 26
<211> LENGTH: 114
<212> TYPE: PRT
<213> ORGANISM: Artificial sequence
<220> FEATURE:
<223> OTHER INFORMATION: Sp1 mutant variant: 6Xhis inserted into
      position 2, T50A and I52A mutated

<400> SEQUENCE: 26

Met His His His His His His Ala Thr Arg Thr Pro Lys Leu Val Lys
1               5                   10                  15

His Thr Leu Leu Thr Arg Phe Lys Asp Glu Ile Thr Arg Glu Gln Ile
            20                  25                  30

Asp Asn Tyr Ile Asn Asp Tyr Thr Asn Leu Leu Asp Leu Ile Pro Ser
        35                  40                  45

Met Lys Ser Phe Asn Trp Gly Ala Asp Ala Gly Met Glu Ser Ala Glu
    50                  55                  60

Leu Asn Arg Gly Tyr Thr His Ala Phe Glu Ser Thr Phe Glu Ser Lys
65                  70                  75                  80

Ser Gly Leu Gln Glu Tyr Leu Asp Ser Ala Ala Leu Ala Ala Phe Ala
                85                  90                  95

Glu Gly Phe Leu Pro Thr Leu Ser Gln Arg Leu Val Ile Asp Tyr Phe
            100                 105                 110

Leu Tyr

<210> SEQ ID NO 27
<211> LENGTH: 114
<212> TYPE: PRT
<213> ORGANISM: Artificial sequence
<220> FEATURE:
<223> OTHER INFORMATION: Sp1 mutant variant: 6Xhis inserted into
      position 2, F106A and Y108A mutated

<400> SEQUENCE: 27

Met His His His His His His Ala Thr Arg Thr Pro Lys Leu Val Lys

```
                1               5                  10                 15
His Thr Leu Leu Thr Arg Phe Lys Asp Glu Ile Thr Arg Glu Gln Ile
            20                  25                 30

Asp Asn Tyr Ile Asn Asp Tyr Thr Asn Leu Leu Asp Leu Ile Pro Ser
            35                  40                 45

Met Lys Ser Phe Asn Trp Gly Thr Asp Leu Gly Met Glu Ser Ala Glu
        50                  55                 60

Leu Asn Arg Gly Tyr Thr His Ala Phe Glu Ser Thr Phe Glu Ser Lys
65                  70                  75                      80

Ser Gly Leu Gln Glu Tyr Leu Asp Ser Ala Ala Leu Ala Ala Phe Ala
                85                  90                  95

Glu Gly Phe Leu Pro Thr Leu Ser Gln Arg Leu Val Ile Asp Tyr Ala
            100                 105                110

Leu Ala
```

<210> SEQ ID NO 28
<211> LENGTH: 114
<212> TYPE: PRT
<213> ORGANISM: Artificial sequence
<220> FEATURE:
<223> OTHER INFORMATION: Sp1 mutant variant: 6Xhis inserted into
      position 2, S73A and S75A mutated

<400> SEQUENCE: 28

```
Met His His His His His His Ala Thr Arg Thr Pro Lys Leu Val Lys
1               5                  10                 15

His Thr Leu Leu Thr Arg Phe Lys Asp Glu Ile Thr Arg Glu Gln Ile
            20                  25                 30

Asp Asn Tyr Ile Asn Asp Tyr Thr Asn Leu Leu Asp Leu Ile Pro Ser
            35                  40                 45

Met Lys Ser Phe Asn Trp Gly Thr Asp Leu Gly Met Glu Ser Ala Glu
        50                  55                 60

Leu Asn Arg Gly Tyr Thr His Ala Phe Glu Ser Thr Phe Glu Ala Lys
65                  70                  75                      80

Ala Gly Leu Gln Glu Tyr Leu Asp Ser Ala Ala Leu Ala Ala Phe Ala
                85                  90                  95

Glu Gly Phe Leu Pro Thr Leu Ser Gln Arg Leu Val Ile Asp Tyr Phe
            100                 105                110

Leu Tyr
```

<210> SEQ ID NO 29
<211> LENGTH: 114
<212> TYPE: PRT
<213> ORGANISM: Artificial sequence
<220> FEATURE:
<223> OTHER INFORMATION: Sp1 mutant variant: 6Xhis inserted into
      position 2, D38A and S75A mutated

<400> SEQUENCE: 29

```
Met His His His His His His Ala Thr Arg Thr Pro Lys Leu Val Lys
1               5                  10                 15

His Thr Leu Leu Thr Arg Phe Lys Asp Glu Ile Thr Arg Glu Gln Ile
            20                  25                 30

Asp Asn Tyr Ile Asn Asp Tyr Thr Asn Leu Leu Ala Leu Ile Pro Ser
            35                  40                 45

Met Lys Ser Phe Asn Trp Gly Thr Asp Leu Gly Met Glu Ser Ala Glu
        50                  55                 60
```

```
Leu Asn Arg Gly Tyr Thr His Ala Phe Glu Ser Thr Phe Glu Ser Lys
 65                  70                  75                  80

Ala Gly Leu Gln Glu Tyr Leu Asp Ser Ala Ala Leu Ala Ala Phe Ala
                 85                  90                  95

Glu Gly Phe Leu Pro Thr Leu Ser Gln Arg Leu Val Ile Asp Tyr Phe
            100                 105                 110

Leu Tyr
```

<210> SEQ ID NO 30
<211> LENGTH: 114
<212> TYPE: PRT
<213> ORGANISM: Artificial sequence
<220> FEATURE:
<223> OTHER INFORMATION: Sp1 mutant variant: 6Xhis inserted into
     position 2, N31A and T34A mutated

<400> SEQUENCE: 30

```
Met His His His His His Ala Thr Arg Thr Pro Lys Leu Val Lys
 1               5                  10                  15

His Thr Leu Leu Thr Arg Phe Lys Asp Glu Ile Thr Arg Glu Gln Ile
                 20                  25                  30

Asp Asn Tyr Ile Ala Asp Tyr Ala Asn Leu Leu Asp Leu Ile Pro Ser
            35                  40                  45

Met Lys Ser Phe Asn Trp Gly Thr Asp Leu Gly Met Glu Ser Ala Glu
 50                  55                  60

Leu Asn Arg Gly Tyr Thr His Ala Phe Glu Ser Thr Phe Glu Ser Lys
 65                  70                  75                  80

Ser Gly Leu Gln Glu Tyr Leu Asp Ser Ala Ala Leu Ala Ala Phe Ala
                 85                  90                  95

Glu Gly Phe Leu Pro Thr Leu Ser Gln Arg Leu Val Ile Asp Tyr Phe
            100                 105                 110

Leu Tyr
```

<210> SEQ ID NO 31
<211> LENGTH: 11
<212> TYPE: PRT
<213> ORGANISM: Artificial sequence
<220> FEATURE:
<223> OTHER INFORMATION: Tumor surface specific peptide

<400> SEQUENCE: 31

```
Lys Asn Gly Pro Trp Tyr Ala Tyr Thr Gly Arg
 1               5                  10
```

<210> SEQ ID NO 32
<211> LENGTH: 8
<212> TYPE: PRT
<213> ORGANISM: Artificial sequence
<220> FEATURE:
<223> OTHER INFORMATION: Tumor surface specific peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 32

```
Asn Trp Ala Val Trp Xaa Lys Arg
 1               5
```

<210> SEQ ID NO 33
<211> LENGTH: 9
<212> TYPE: PRT

<213> ORGANISM: Artificial sequence
<220> FEATURE:
<223> OTHER INFORMATION: Tumor surface specific peptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 33

Tyr Xaa Xaa Glu Asp Leu Arg Arg Arg
1               5

<210> SEQ ID NO 34
<211> LENGTH: 8
<212> TYPE: PRT
<213> ORGANISM: Artificial sequence
<220> FEATURE:
<223> OTHER INFORMATION: Tumor surface specific peptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 34

Xaa Xaa Pro Val Asp His Gly Leu
1               5

<210> SEQ ID NO 35
<211> LENGTH: 9
<212> TYPE: PRT
<213> ORGANISM: Artificial sequence
<220> FEATURE:
<223> OTHER INFORMATION: Tumor surface specific peptide

<400> SEQUENCE: 35

Leu Val Arg Ser Thr Gly Gln Phe Val
1               5

<210> SEQ ID NO 36
<211> LENGTH: 9
<212> TYPE: PRT
<213> ORGANISM: Artificial sequence
<220> FEATURE:
<223> OTHER INFORMATION: Tumor surface specific peptide

<400> SEQUENCE: 36

Leu Val Ser Pro Ser Gly Ser Trp Thr
1               5

<210> SEQ ID NO 37
<211> LENGTH: 9
<212> TYPE: PRT
<213> ORGANISM: Artificial sequence
<220> FEATURE:
<223> OTHER INFORMATION: Tumor surface specific peptide

<400> SEQUENCE: 37

Ala Leu Arg Pro Ser Gly Glu Trp Leu
1               5

<210> SEQ ID NO 38
<211> LENGTH: 9
<212> TYPE: PRT
<213> ORGANISM: Artificial sequence
<220> FEATURE:
<223> OTHER INFORMATION: Tumor surface specific peptide

<400> SEQUENCE: 38

```
Ala Ile Met Ala Ser Gly Gln Trp Leu
1               5
```

<210> SEQ ID NO 39
<211> LENGTH: 9
<212> TYPE: PRT
<213> ORGANISM: Artificial sequence
<220> FEATURE:
<223> OTHER INFORMATION: Tumor surface specific peptide

<400> SEQUENCE: 39

```
Gln Ile Leu Ala Ser Gly Arg Trp Leu
1               5
```

<210> SEQ ID NO 40
<211> LENGTH: 9
<212> TYPE: PRT
<213> ORGANISM: Artificial sequence
<220> FEATURE:
<223> OTHER INFORMATION: Tumor surface specific peptide

<400> SEQUENCE: 40

```
Arg Arg Pro Ser His Ala Met Ala Arg
1               5
```

<210> SEQ ID NO 41
<211> LENGTH: 9
<212> TYPE: PRT
<213> ORGANISM: Artificial sequence
<220> FEATURE:
<223> OTHER INFORMATION: Tumor surface specific peptide

<400> SEQUENCE: 41

```
Asp Asn Asn Arg Pro Ala Asn Ser Met
1               5
```

<210> SEQ ID NO 42
<211> LENGTH: 9
<212> TYPE: PRT
<213> ORGANISM: Artificial sequence
<220> FEATURE:
<223> OTHER INFORMATION: Tumor surface specific peptide

<400> SEQUENCE: 42

```
Leu Gln Asp Arg Leu Arg Phe Ala Thr
1               5
```

<210> SEQ ID NO 43
<211> LENGTH: 9
<212> TYPE: PRT
<213> ORGANISM: Artificial sequence
<220> FEATURE:
<223> OTHER INFORMATION: Tumor surface specific peptide

<400> SEQUENCE: 43

```
Pro Leu Ser Gly Asp Lys Ser Ser Thr
1               5
```

<210> SEQ ID NO 44
<211> LENGTH: 6
<212> TYPE: PRT
<213> ORGANISM: Artificial sequence
<220> FEATURE:
<223> OTHER INFORMATION: Tumor surface specific peptide

<400> SEQUENCE: 44

```
Phe Asp Asp Ala Arg Leu
```

<210> SEQ ID NO 45
<211> LENGTH: 6
<212> TYPE: PRT
<213> ORGANISM: Artificial sequence
<220> FEATURE:
<223> OTHER INFORMATION: Tumor surface specific peptide

<400> SEQUENCE: 45

Phe Ser Asp Ala Arg Leu
1               5

<210> SEQ ID NO 46
<211> LENGTH: 6
<212> TYPE: PRT
<213> ORGANISM: Artificial sequence
<220> FEATURE:
<223> OTHER INFORMATION: Tumor surface specific peptide

<400> SEQUENCE: 46

Phe Ser Asp Met Arg Leu
1               5

<210> SEQ ID NO 47
<211> LENGTH: 6
<212> TYPE: PRT
<213> ORGANISM: Artificial sequence
<220> FEATURE:
<223> OTHER INFORMATION: Tumor surface specific peptide

<400> SEQUENCE: 47

Phe Val Asp Val Arg Leu
1               5

<210> SEQ ID NO 48
<211> LENGTH: 6
<212> TYPE: PRT
<213> ORGANISM: Artificial sequence
<220> FEATURE:
<223> OTHER INFORMATION: Tumor surface specific peptide

<400> SEQUENCE: 48

Phe Thr Asp Ile Arg Leu
1               5

<210> SEQ ID NO 49
<211> LENGTH: 6
<212> TYPE: PRT
<213> ORGANISM: Artificial sequence
<220> FEATURE:
<223> OTHER INFORMATION: Tumor surface specific peptide

<400> SEQUENCE: 49

Phe Asn Asp Tyr Arg Leu
1               5

<210> SEQ ID NO 50
<211> LENGTH: 6
<212> TYPE: PRT
<213> ORGANISM: Artificial sequence
<220> FEATURE:
<223> OTHER INFORMATION: Tumor surface specific peptide

<400> SEQUENCE: 50

Phe Ser Asp Thr Arg Leu
1               5

```
<210> SEQ ID NO 51
<211> LENGTH: 6
<212> TYPE: PRT
<213> ORGANISM: Artificial sequence
<220> FEATURE:
<223> OTHER INFORMATION: Tumor surface specific peptide

<400> SEQUENCE: 51

Pro Ile His Tyr Ile Phe
1               5

<210> SEQ ID NO 52
<211> LENGTH: 6
<212> TYPE: PRT
<213> ORGANISM: Artificial sequence
<220> FEATURE:
<223> OTHER INFORMATION: Tumor surface specific peptide

<400> SEQUENCE: 52

Tyr Ile His Tyr Ile Phe
1               5

<210> SEQ ID NO 53
<211> LENGTH: 6
<212> TYPE: PRT
<213> ORGANISM: Artificial sequence
<220> FEATURE:
<223> OTHER INFORMATION: Tumor surface specific peptide

<400> SEQUENCE: 53

Arg Ile His Tyr Ile Phe
1               5

<210> SEQ ID NO 54
<211> LENGTH: 7
<212> TYPE: PRT
<213> ORGANISM: Artificial sequence
<220> FEATURE:
<223> OTHER INFORMATION: Tumor surface specific peptide

<400> SEQUENCE: 54

Ile Glu Leu Leu Gln Ala Arg
1               5

<210> SEQ ID NO 55
<211> LENGTH: 10
<212> TYPE: PRT
<213> ORGANISM: Artificial sequence
<220> FEATURE:
<223> OTHER INFORMATION: Tumor surface specific peptide
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 55

Cys Val Phe Xaa Xaa Xaa Tyr Xaa Xaa Cys
1               5                   10

<210> SEQ ID NO 56
<211> LENGTH: 12
<212> TYPE: PRT
<213> ORGANISM: Artificial sequence
```

```
<220> FEATURE:
<223> OTHER INFORMATION: Tumor surface specific peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 56

Cys Xaa Phe Xaa Xaa Xaa Tyr Xaa Tyr Leu Met Cys
1               5                   10

<210> SEQ ID NO 57
<211> LENGTH: 13
<212> TYPE: PRT
<213> ORGANISM: Artificial sequence
<220> FEATURE:
<223> OTHER INFORMATION: Tumor surface specific peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(9)
<223> OTHER INFORMATION: Xaa can be any naturally occurring amino acid

<400> SEQUENCE: 57

Cys Val Xaa Tyr Cys Xaa Xaa Xaa Xaa Cys Tyr Val Cys
1               5                   10

<210> SEQ ID NO 58
<211> LENGTH: 13
<212> TYPE: PRT
<213> ORGANISM: Artificial sequence
<220> FEATURE:
<223> OTHER INFORMATION: Tumor surface specific peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 58

Cys Val Xaa Tyr Cys Xaa Xaa Xaa Xaa Cys Trp Xaa Cys
1               5                   10

<210> SEQ ID NO 59
<211> LENGTH: 8
<212> TYPE: PRT
<213> ORGANISM: Artificial sequence
<220> FEATURE:
<223> OTHER INFORMATION: Tumor surface specific peptide

<400> SEQUENCE: 59

Asp Pro Arg Ala Thr Pro Gly Ser
1               5
```

```
<210> SEQ ID NO 60
<211> LENGTH: 12
<212> TYPE: PRT
<213> ORGANISM: Artificial sequence
<220> FEATURE:
<223> OTHER INFORMATION: Tumor surface specific peptide

<400> SEQUENCE: 60

His Leu Gln Leu Gln Pro Trp Tyr Pro Gln Ile Ser
1               5                   10

<210> SEQ ID NO 61
<211> LENGTH: 12
<212> TYPE: PRT
<213> ORGANISM: Artificial sequence
<220> FEATURE:
<223> OTHER INFORMATION: Tumor surface specific peptide

<400> SEQUENCE: 61

Val Pro Trp Met Glu Pro Ala Tyr Gln Arg Phe Leu
1               5                   10

<210> SEQ ID NO 62
<211> LENGTH: 12
<212> TYPE: PRT
<213> ORGANISM: Artificial sequence
<220> FEATURE:
<223> OTHER INFORMATION: Tumor surface specific peptide

<400> SEQUENCE: 62

Thr Ser Pro Leu Asn Ile His Asn Gly Gln Lys Leu
1               5                   10

<210> SEQ ID NO 63
<211> LENGTH: 9
<212> TYPE: PRT
<213> ORGANISM: Artificial sequence
<220> FEATURE:
<223> OTHER INFORMATION: Tumor vascular peptides

<400> SEQUENCE: 63

Cys Asp Cys Arg Gly Asp Cys Phe Cys
1               5

<210> SEQ ID NO 64
<211> LENGTH: 11
<212> TYPE: PRT
<213> ORGANISM: Artificial sequence
<220> FEATURE:
<223> OTHER INFORMATION: Tumor vascular peptides

<400> SEQUENCE: 64

Ala Cys Asp Cys Arg Gly Asp Cys Phe Cys Gly
1               5                   10

<210> SEQ ID NO 65
<211> LENGTH: 13
<212> TYPE: PRT
<213> ORGANISM: Artificial sequence
<220> FEATURE:
<223> OTHER INFORMATION: Tumor vascular peptides

<400> SEQUENCE: 65

Cys Asn Gly Arg Cys Val Ser Gly Cys Ala Gly Arg Cys
1               5                   10
```

```
<210> SEQ ID NO 66
<211> LENGTH: 9
<212> TYPE: PRT
<213> ORGANISM: Artificial sequence
<220> FEATURE:
<223> OTHER INFORMATION: Tumor vascular peptides

<400> SEQUENCE: 66

Cys Val Cys Asn Gly Arg Met Glu Cys
1               5

<210> SEQ ID NO 67
<211> LENGTH: 6
<212> TYPE: PRT
<213> ORGANISM: Artificial sequence
<220> FEATURE:
<223> OTHER INFORMATION: Tumor vascular peptides

<400> SEQUENCE: 67

Asn Gly Arg Ala His Ala
1               5

<210> SEQ ID NO 68
<211> LENGTH: 10
<212> TYPE: PRT
<213> ORGANISM: Artificial sequence
<220> FEATURE:
<223> OTHER INFORMATION: Tumor vascular peptides

<400> SEQUENCE: 68

Thr Ala Ala Ser Gly Val Arg Ser Met His
1               5                   10

<210> SEQ ID NO 69
<211> LENGTH: 10
<212> TYPE: PRT
<213> ORGANISM: Artificial sequence
<220> FEATURE:
<223> OTHER INFORMATION: Tumor vascular peptides

<400> SEQUENCE: 69

Leu Thr Leu Arg Trp Val Gly Leu Met Ser
1               5                   10

<210> SEQ ID NO 70
<211> LENGTH: 7
<212> TYPE: PRT
<213> ORGANISM: Artificial sequence
<220> FEATURE:
<223> OTHER INFORMATION: Tumor vascular peptides

<400> SEQUENCE: 70

Cys Gly Ser Leu Val Arg Cys
1               5

<210> SEQ ID NO 71
<211> LENGTH: 7
<212> TYPE: PRT
<213> ORGANISM: Artificial sequence
<220> FEATURE:
<223> OTHER INFORMATION: Tumor vascular peptides

<400> SEQUENCE: 71

Cys Gly Leu Ser Asp Ser Cys
1               5

<210> SEQ ID NO 72
```

```
<211> LENGTH: 15
<212> TYPE: PRT
<213> ORGANISM: Artificial sequence
<220> FEATURE:
<223> OTHER INFORMATION: Tumor vascular peptides

<400> SEQUENCE: 72

Asn Arg Ser Leu Lys Arg Ile Ser Asn Lys Arg Ile Arg Arg Lys
1               5                   10                  15

<210> SEQ ID NO 73
<211> LENGTH: 15
<212> TYPE: PRT
<213> ORGANISM: Artificial sequence
<220> FEATURE:
<223> OTHER INFORMATION: Tumor vascular peptides

<400> SEQUENCE: 73

Leu Arg Ile Lys Arg Lys Arg Arg Lys Arg Lys Lys Thr Arg Lys
1               5                   10                  15

<210> SEQ ID NO 74
<211> LENGTH: 6
<212> TYPE: PRT
<213> ORGANISM: Artificial sequence
<220> FEATURE:
<223> OTHER INFORMATION: Tumor vascular peptides

<400> SEQUENCE: 74

Asn Arg Ser Thr His Ile
1               5

<210> SEQ ID NO 75
<211> LENGTH: 7
<212> TYPE: PRT
<213> ORGANISM: Artificial sequence
<220> FEATURE:
<223> OTHER INFORMATION: Tumor vascular peptides

<400> SEQUENCE: 75

Ser Met Ser Ile Ala Arg Leu
1               5

<210> SEQ ID NO 76
<211> LENGTH: 7
<212> TYPE: PRT
<213> ORGANISM: Artificial sequence
<220> FEATURE:
<223> OTHER INFORMATION: Tumor vascular peptides

<400> SEQUENCE: 76

Val Ser Phe Leu Glu Tyr Arg
1               5

<210> SEQ ID NO 77
<211> LENGTH: 9
<212> TYPE: PRT
<213> ORGANISM: Artificial sequence
<220> FEATURE:
<223> OTHER INFORMATION: Tumor vascular peptides

<400> SEQUENCE: 77

Cys Pro Gly Pro Glu Gly Ala Gly Cys
1               5

<210> SEQ ID NO 78
<211> LENGTH: 7
```

```
<212> TYPE: PRT
<213> ORGANISM: Artificial sequence
<220> FEATURE:
<223> OTHER INFORMATION: Tumor vascular peptides

<400> SEQUENCE: 78

Ala Thr Trp Leu Pro Pro Arg
1               5

<210> SEQ ID NO 79
<211> LENGTH: 6
<212> TYPE: PRT
<213> ORGANISM: Artificial sequence
<220> FEATURE:
<223> OTHER INFORMATION: Tumor vascular peptides

<400> SEQUENCE: 79

Arg Arg Lys Arg Arg Arg
1               5

<210> SEQ ID NO 80
<211> LENGTH: 15
<212> TYPE: PRT
<213> ORGANISM: Artificial sequence
<220> FEATURE:
<223> OTHER INFORMATION: Tumor vascular peptides

<400> SEQUENCE: 80

Ala Ser Ser Ser Tyr Pro Leu Ile His Trp Arg Pro Trp Ala Arg
1               5                   10                  15

<210> SEQ ID NO 81
<211> LENGTH: 10
<212> TYPE: PRT
<213> ORGANISM: Artificial sequence
<220> FEATURE:
<223> OTHER INFORMATION: Tumor vascular peptides

<400> SEQUENCE: 81

Cys Thr Thr His Trp Gly Phe Thr Leu Cys
1               5                   10

<210> SEQ ID NO 82
<211> LENGTH: 14
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 82

Met His Gly Lys Thr Gln Ala Thr Ser Gly Thr Ile Gln Ser
1               5                   10

<210> SEQ ID NO 83
<211> LENGTH: 20
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 83

Ser Lys Thr Ser Leu Gly Cys Gln Lys Pro Leu Tyr Met Gly Arg Glu
1               5                   10                  15

Met Arg Met Leu
            20
```

```
<210> SEQ ID NO 84
<211> LENGTH: 21
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 84

Gln Ala Thr Ser Glu Lys Leu Val Arg Gly Met Glu Gly Ala Ser Leu
1               5                   10                  15

His Pro Ala Lys Thr
            20

<210> SEQ ID NO 85
<211> LENGTH: 7
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 85

Asp Arg Thr Ser Thr Trp Arg
1               5

<210> SEQ ID NO 86
<211> LENGTH: 7
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 86

Gln Ser Val Thr Ser Thr Lys
1               5

<210> SEQ ID NO 87
<211> LENGTH: 7
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 87

Ser Ser Ser His Leu Asn Lys
1               5

<210> SEQ ID NO 88
<211> LENGTH: 7
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 88

Ser Val Thr Gln Asn Lys Tyr
1               5

<210> SEQ ID NO 89
<211> LENGTH: 7
<212> TYPE: PRT
<213> ORGANISM: Artificial sequence
```

```
<220> FEATURE:
<223> OTHER INFORMATION: An inorganic-binding polypeptide selected by
      phage display (PD) and cell surface display (CSD)

<400> SEQUENCE: 89

Ser Pro His Pro Gly Pro Tyr
1               5

<210> SEQ ID NO 90
<211> LENGTH: 7
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 90

His Ala Pro Thr Pro Met Leu
1               5

<210> SEQ ID NO 91
<211> LENGTH: 12
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 91

Ala Tyr Ser Ser Gly Ala Pro Pro Met Pro Pro Phe
1               5                   10

<210> SEQ ID NO 92
<211> LENGTH: 12
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 92

Asn Pro Ser Ser Leu Phe Arg Tyr Leu Pro Ser Asp
1               5                   10

<210> SEQ ID NO 93
<211> LENGTH: 12
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 93

Ser Leu Ala Thr Gln Pro Pro Arg Thr Pro Pro Val
1               5                   10

<210> SEQ ID NO 94
<211> LENGTH: 12
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 94

Met Ser Pro His Pro His Pro Arg His His His Thr
1               5                   10
```

<210> SEQ ID NO 95
<211> LENGTH: 12
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 95

Arg Gly Arg Arg Arg Arg Leu Ser Cys Arg Leu Leu
1               5                   10

<210> SEQ ID NO 96
<211> LENGTH: 12
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 96

Lys Pro Ser His His His His Thr Gly Ala Asn
1               5                   10

<210> SEQ ID NO 97
<211> LENGTH: 12
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 97

Tyr Ser Asp Gln Pro Thr Gln Ser Ser Gln Arg Pro
1               5                   10

<210> SEQ ID NO 98
<211> LENGTH: 12
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 98

Thr Tyr His Ser Ser Gln Leu Gln Arg Pro Pro Leu
1               5                   10

<210> SEQ ID NO 99
<211> LENGTH: 12
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 99

Ser Pro Leu Ser Ile Ala Ala Ser Ser Pro Trp Pro
1               5                   10

<210> SEQ ID NO 100
<211> LENGTH: 22
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

```
<400> SEQUENCE: 100

Ser Ser Lys Lys Ser Gly Ser Tyr Ser Gly Tyr Ser Thr Lys Ser
1               5                   10                  15

Gly Ser Arg Arg Ile Leu
            20

<210> SEQ ID NO 101
<211> LENGTH: 19
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 101

Ser Ser Lys Lys Ser Gly Ser Tyr Ser Gly Ser Lys Gly Ser Lys Arg
1               5                   10                  15

Arg Ile Leu

<210> SEQ ID NO 102
<211> LENGTH: 19
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 102

Ser Ser Lys Lys Ser Gly Ser Tyr Ser Gly Ser Lys Gly Ser Lys Arg
1               5                   10                  15

Arg Asn Leu

<210> SEQ ID NO 103
<211> LENGTH: 8
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 103

Ser Ser Arg Cys Ser Ser Ser Ser
1               5

<210> SEQ ID NO 104
<211> LENGTH: 12
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 104

Val Arg Thr Arg Asp Asp Ala Arg Thr His Arg Lys
1               5                   10

<210> SEQ ID NO 105
<211> LENGTH: 12
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 105
```

```
Pro Ala Ser Arg Val Glu Lys Asn Gly Val Arg Arg
1               5                   10
```

<210> SEQ ID NO 106
<211> LENGTH: 20
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 106

```
Asn Thr Arg Met Thr Ala Arg Gln His Arg Ser Ala Asn His Lys Ser
1               5                   10                  15

Thr Gln Arg Ala
            20
```

<210> SEQ ID NO 107
<211> LENGTH: 9
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 107

```
Tyr Asp Ser Arg Ser Met Arg Pro His
1               5
```

<210> SEQ ID NO 108
<211> LENGTH: 12
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 108

```
Arg His Thr Asp Gly Leu Arg Arg Ile Ala Ala Arg
1               5                   10
```

<210> SEQ ID NO 109
<211> LENGTH: 12
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 109

```
Arg Thr Arg Arg Gln Gly Gly Asp Val Ser Arg Asp
1               5                   10
```

<210> SEQ ID NO 110
<211> LENGTH: 12
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 110

```
Arg Pro Arg Arg Ser Ala Ala Arg Gly Ser Glu Gly
1               5                   10
```

<210> SEQ ID NO 111
<211> LENGTH: 21

```
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 111

Val Lys Thr Gln Ala Thr Ser Arg Glu Glu Pro Pro Arg Leu Pro Ser
1               5                   10                  15

Lys His Arg Pro Gly
            20

<210> SEQ ID NO 112
<211> LENGTH: 14
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 112

Met Asp His Gly Lys Tyr Arg Gln Lys Gln Ala Thr Pro Gly
1               5                   10

<210> SEQ ID NO 113
<211> LENGTH: 13
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 113

His Thr Gln Asn Met Arg Met Tyr Glu Pro Trp Phe Gly
1               5                   10

<210> SEQ ID NO 114
<211> LENGTH: 13
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 114

Asp Val Phe Ser Ser Phe Asn Leu Lys His Met Arg Gly
1               5                   10

<210> SEQ ID NO 115
<211> LENGTH: 9
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 115

Val Val Arg Pro Lys Ala Ala Thr Asn
1               5

<210> SEQ ID NO 116
<211> LENGTH: 9
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)
```

```
<400> SEQUENCE: 116

Arg Ile Arg His Arg Leu Val Gly Gln
1               5

<210> SEQ ID NO 117
<211> LENGTH: 9
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 117

Arg Arg Thr Val Lys His His Val Asn
1               5

<210> SEQ ID NO 118
<211> LENGTH: 11
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 118

Ala Gln Asn Pro Ser Asp Asn Asn Thr His Thr
1               5                   10

<210> SEQ ID NO 119
<211> LENGTH: 12
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 119

Arg Leu Glu Leu Ala Ile Pro Leu Gln Gly Ser Gly
1               5                   10

<210> SEQ ID NO 120
<211> LENGTH: 12
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 120

Thr Pro Pro Arg Pro Ile Gln Tyr Asn His Thr Ser
1               5                   10

<210> SEQ ID NO 121
<211> LENGTH: 7
<212> TYPE: PRT
<213> ORGANISM: Artificial sequence
<220> FEATURE:
<223> OTHER INFORMATION: An inorganic-binding polypeptide selected by
      phage display (PD) and cell surface display (CSD)

<400> SEQUENCE: 121

Asn Asn Pro Met His Gln Asn
1               5

<210> SEQ ID NO 122
<211> LENGTH: 6
<212> TYPE: PRT
```

<213> ORGANISM: Artificial sequence
<220> FEATURE:
<223> OTHER INFORMATION: 6XHis tag

<400> SEQUENCE: 122

His His His His His His
1               5

<210> SEQ ID NO 123
<211> LENGTH: 98
<212> TYPE: PRT
<213> ORGANISM: Triticum aestivum
<220> FEATURE:
<221> NAME/KEY: misc_feature
<222> LOCATION: (50)..(51)
<223> OTHER INFORMATION: Xaa can be any naturally occurring amino acid

<400> SEQUENCE: 123

Val Val Lys His Leu Val Ile Val Gln Phe Lys Glu Asp Val Thr Pro
1               5                   10                  15

Glu Arg Leu Asp Gly Leu Ile Arg Gly Tyr Ala Gly Leu Val Asp Lys
            20                  25                  30

Val Pro Ser Met Lys Ala Phe His Trp Gly Thr Asp Val Ser Ile Glu
        35                  40                  45

Asn Xaa Xaa Met His Gln Gly Phe Thr His Val Phe Glu Ser Thr Phe
    50                  55                  60

Glu Ser Thr Glu Gly Val Lys Glu Tyr Val Tyr His Pro Ala His Val
65                  70                  75                  80

Glu Phe Ala Thr Asp Phe Leu Gly Ser Thr Glu Lys Val Leu Ile Ile
                85                  90                  95

Asp Phe

<210> SEQ ID NO 124
<211> LENGTH: 98
<212> TYPE: PRT
<213> ORGANISM: Triticum aestivum
<220> FEATURE:
<221> NAME/KEY: misc_feature
<222> LOCATION: (50)..(51)
<223> OTHER INFORMATION: Xaa can be any naturally occurring amino acid

<400> SEQUENCE: 124

Val Val Lys His Leu Val Ile Val Gln Phe Lys Glu Asp Val Thr Pro
1               5                   10                  15

Glu Arg Leu Asp Gly Leu Ile Arg Gly Tyr Ala Gly Leu Val Asp Lys
            20                  25                  30

Val Pro Ser Met Lys Ala Phe His Trp Gly Thr Asp Val Ser Ile Glu
        35                  40                  45

Asn Xaa Xaa Met His Gln Gly Phe Thr His Val Phe Glu Ser Thr Phe
    50                  55                  60

Glu Ser Thr Glu Gly Val Lys Glu Tyr Val Tyr His Pro Ala His Val
65                  70                  75                  80

Glu Phe Ala Thr Asp Phe Leu Gly Ser Thr Glu Lys Val Leu Ile Ile
                85                  90                  95

Asp Phe

<210> SEQ ID NO 125
<211> LENGTH: 98
<212> TYPE: PRT
<213> ORGANISM: Triticum aestivum
<220> FEATURE:

```
<221> NAME/KEY: misc_feature
<222> LOCATION: (50)..(51)
<223> OTHER INFORMATION: Xaa can be any naturally occurring amino acid

<400> SEQUENCE: 125

Val Val Lys His Leu Val Ile Val Gln Phe Lys Glu Asp Val Thr Pro
1               5                   10                  15

Glu Arg Leu Glu Gly Leu Ile Arg Gly Tyr Ala Gly Leu Val Asp Lys
            20                  25                  30

Val Pro Ser Met Lys Ala Phe His Trp Gly Thr Asp Val Ser Ile Glu
        35                  40                  45

Asn Xaa Xaa Met His Gln Gly Phe Thr His Val Phe Glu Ser Thr Phe
    50                  55                  60

Glu Ser Thr Glu Gly Val Lys Glu Tyr Val Tyr His Pro Ala His Val
65                  70                  75                  80

Glu Phe Ala Thr Asp Phe Leu Gly Ser Thr Glu Lys Val Leu Ile Ile
            85                  90                  95

Asp Phe

<210> SEQ ID NO 126
<211> LENGTH: 84
<212> TYPE: PRT
<213> ORGANISM: Zea mays
<220> FEATURE:
<221> NAME/KEY: misc_feature
<222> LOCATION: (50)..(51)
<223> OTHER INFORMATION: Xaa can be any naturally occurring amino acid

<400> SEQUENCE: 126

Val Val Lys His Ile Leu Leu Ala Ser Phe Lys Glu Glu Val Thr Gln
1               5                   10                  15

Glu Arg Leu Asp Glu Leu Ile Arg Gly Tyr Ala Ala Leu Val Gly Val
            20                  25                  30

Val Pro Ser Met Lys Ala Phe His Trp Gly Thr Asp Val Ser Ile Glu
        35                  40                  45

Asn Xaa Xaa Met His Gln Gly Phe Thr His Val Phe Glu Ser Thr Phe
    50                  55                  60

Glu Ser Thr Glu Gly Ile Lys Glu Tyr Ile Glu His Pro Ala His Val
65                  70                  75                  80

Glu Phe Ala Lys

<210> SEQ ID NO 127
<211> LENGTH: 98
<212> TYPE: PRT
<213> ORGANISM: Oryza sativa
<220> FEATURE:
<221> NAME/KEY: misc_feature
<222> LOCATION: (50)..(51)
<223> OTHER INFORMATION: Xaa can be any naturally occurring amino acid

<400> SEQUENCE: 127

Val Val Lys His Ile Leu Leu Ala Arg Phe Lys Glu Asp Val Ala Pro
1               5                   10                  15

Glu Arg Leu Asp Gln Leu Ile Arg Gly Tyr Ala Gly Leu Val Asp Leu
            20                  25                  30

Val Pro Ser Met Lys Ala Phe His Trp Gly Thr Asp Val Ser Ile Glu
        35                  40                  45

Asn Xaa Xaa Met His Gln Gly Phe Thr His Val Phe Glu Ser Thr Phe
    50                  55                  60
```

```
Glu Ser Thr Glu Gly Val Lys Glu Tyr Ile Glu His Pro Ala His Val
 65                  70                  75                  80

Glu Phe Ala Asn Glu Phe Leu Pro Val Leu Glu Lys Thr Leu Ile Ile
                 85                  90                  95

Asp Tyr

<210> SEQ ID NO 128
<211> LENGTH: 98
<212> TYPE: PRT
<213> ORGANISM: Triticum aestivum
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (48)..(49)
<223> OTHER INFORMATION: Xaa can be any naturally occurring amino acid

<400> SEQUENCE: 128

Val Val Lys His Leu Val Leu Ala Arg Phe Lys Glu Glu Ala Thr Pro
 1               5                  10                  15

Glu Ala Leu Asp Xaa Leu Ile Arg Arg Tyr Ala Gly Leu Val Asp Ala
                 20                  25                  30

Val Pro Ser Met Lys Ala Phe His Trp Gly Thr Asp Val Thr Val Xaa
             35                  40                  45

Xaa Leu Asp Thr His Glu Gly Phe Thr His Val Phe Glu Ser Thr Phe
 50                  55                  60

Glu Ser Ala Glu Gly Val Lys Glu Tyr Ile Ala His Pro Ser His Val
 65                  70                  75                  80

Glu Phe Val Asp Glu Phe Leu Ala Leu Ala Glu Lys Met Leu Ile Val
                 85                  90                  95

Asp Tyr

<210> SEQ ID NO 129
<211> LENGTH: 109
<212> TYPE: PRT
<213> ORGANISM: Arabidopsis thaliana

<400> SEQUENCE: 129

Met Glu Glu Ala Lys Gly Pro Val Lys His Val Leu Leu Ala Ser Phe
 1               5                  10                  15

Lys Asp Gly Val Ser Pro Glu Lys Ile Glu Glu Leu Ile Lys Gly Tyr
                 20                  25                  30

Ala Asn Leu Val Asn Leu Ile Glu Pro Met Lys Ala Phe His Trp Gly
             35                  40                  45

Lys Asp Val Ser Ile Glu Asn Leu His Gln Gly Tyr Thr His Ile Phe
 50                  55                  60

Glu Ser Thr Phe Glu Ser Lys Glu Ala Val Ala Glu Tyr Ile Ala His
 65                  70                  75                  80

Pro Ala His Val Glu Phe Ala Thr Ile Phe Leu Gly Ser Leu Asp Lys
                 85                  90                  95

Val Leu Val Ile Asp Tyr Lys Pro Thr Ser Val Ser Leu
             100                 105

<210> SEQ ID NO 130
<211> LENGTH: 47
<212> TYPE: PRT
<213> ORGANISM: Arabidopsis thaliana
```

```
<400> SEQUENCE: 130

Leu His Gln Gly Tyr Thr His Ile Leu Glu Ser Thr Phe Ser Lys
1               5                   10                  15

Glu Ala Val Ala Glu Tyr Ile Ala His Pro Ala His Val Glu Phe Ala
                20                  25                  30

Thr Ile Phe Leu Gly Ser Leu Asp Lys Val Leu Val Ile Asp Tyr
                35                  40                  45

<210> SEQ ID NO 131
<211> LENGTH: 98
<212> TYPE: PRT
<213> ORGANISM: Glycine max
<220> FEATURE:
<221> NAME/KEY: misc_feature
<222> LOCATION: (50)..(51)
<223> OTHER INFORMATION: Xaa can be any naturally occurring amino acid

<400> SEQUENCE: 131

Val Val Lys His Val Leu Leu Ala Lys Phe Lys Asp Asp Val Thr Pro
1               5                   10                  15

Glu Arg Ile Glu Glu Leu Ile Lys Asp Tyr Ala Asn Leu Val Asn Leu
                20                  25                  30

Ile Pro Pro Met Lys Ser Phe His Trp Gly Lys Asp Val Ser Ala Glu
                35                  40                  45

Asn Xaa Xaa Leu His Gln Gly Phe Thr His Val Phe Glu Ser Thr Phe
        50                  55                  60

Glu Ser Pro Glu Gly Val Ala Glu Tyr Val Ala His Pro Ala His Val
65                  70                  75                  80

Glu Tyr Ala Asn Leu Phe Leu Ser Cys Leu Glu Lys Val Ile Val Ile
                85                  90                  95

Asp Tyr

<210> SEQ ID NO 132
<211> LENGTH: 98
<212> TYPE: PRT
<213> ORGANISM: Lycopersicon esculentum
<220> FEATURE:
<221> NAME/KEY: misc_feature
<222> LOCATION: (50)..(51)
<223> OTHER INFORMATION: Xaa can be any naturally occurring amino acid

<400> SEQUENCE: 132

Val Val Lys His Ile Leu Leu Ala Lys Phe Lys Asp Gly Ile Pro Pro
1               5                   10                  15

Glu Gln Ile Asp Gln Leu Ile Lys Gln Tyr Ala Asn Leu Val Asn Leu
                20                  25                  30

Val Glu Pro Met Lys Ala Phe Gln Trp Gly Lys Asp Val Ser Ile Glu
                35                  40                  45

Asn Xaa Xaa Leu His Gln Gly Phe Thr His Val Phe Glu Ser Thr Phe
        50                  55                  60

Asp Ser Leu Glu Gly Val Ala Glu Tyr Ile Ala His Pro Val His Val
65                  70                  75                  80

Glu Tyr Ala Asn Thr Leu Leu Pro Gln Leu Glu Lys Phe Leu Ile Val
                85                  90                  95

Asp Tyr

<210> SEQ ID NO 133
<211> LENGTH: 93
<212> TYPE: PRT
```

<213> ORGANISM: Glycine max
<220> FEATURE:
<221> NAME/KEY: misc_feature
<222> LOCATION: (49)..(50)
<223> OTHER INFORMATION: Xaa can be any naturally occurring amino acid

<400> SEQUENCE: 133

His Val Leu Leu Pro Lys Leu Lys Asp Tyr Phe Thr Pro Glu Arg Ile
1               5                   10                  15

Glu Leu Met Val Asp Tyr Ala Asn Leu Val Asn Leu Met Pro Arg Met
            20                  25                  30

Lys Ser Phe His Ser Gly Arg Asp Val Ser Ala Glu Tyr Leu His Leu
        35                  40                  45

Xaa Xaa Gly Cys Thr His Val Tyr Glu Ser Thr Phe Asp Ser Pro Gly
    50                  55                  60

Val Ala Glu Tyr Val Ala His Ala Ala His Val Glu Tyr Ala Asn Gln
65                  70                  75                  80

Asp Leu Ser Cys Leu Glu Lys Val Ile Ala Ile Asp Tyr
                85                  90

<210> SEQ ID NO 134
<211> LENGTH: 108
<212> TYPE: PRT
<213> ORGANISM: Populus tremula x Populus tremuloides

<400> SEQUENCE: 134

Met Ala Thr Arg Thr Pro Lys Leu Val Lys His Thr Leu Ala Thr Arg
1               5                   10                  15

Phe Lys Asp Glu Ile Thr Arg Glu Gln Ile Asp Asn Tyr Ile Asn Asp
            20                  25                  30

Tyr Thr Asn Leu Leu Asp Leu Ile Pro Ser Met Lys Ser Phe Asn Trp
        35                  40                  45

Gly Thr Asp Leu Gly Met Glu Ser Ala Glu Leu Asn Arg Gly Tyr Thr
    50                  55                  60

His Ala Phe Glu Ser Thr Phe Glu Ser Lys Ser Gly Leu Gln Glu Tyr
65                  70                  75                  80

Leu Asp Ser Ala Ala Leu Ala Ala Phe Ala Glu Gly Phe Leu Pro Thr
                85                  90                  95

Leu Ser Gln Arg Leu Val Ile Asp Tyr Phe Leu Tyr
            100                 105

<210> SEQ ID NO 135
<211> LENGTH: 96
<212> TYPE: PRT
<213> ORGANISM: Triticum aestivum
<220> FEATURE:
<221> NAME/KEY: misc_feature
<222> LOCATION: (18)..(20)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid

<400> SEQUENCE: 135

Lys His Leu Cys Leu Val Arg Phe Lys Glu Gly Val Val Val Glu Asp
1               5                   10                  15

Ile Xaa Xaa Xaa Ile Glu Glu Leu Thr Lys Leu Ala Ala Glu Leu Asp
            20                  25                  30

Thr Val Lys Phe Phe Gly Trp Gly Lys Asp Val Leu Asn Gln Glu Ala
        35                  40                  45

```
Xaa Leu Thr Gln Gly Phe Thr His Val Phe Ser Met Ser Phe Ala Ser
    50                  55                  60

Ala Glu Asp Leu Ala Ala Tyr Met Gly His Glu Lys His Ser Ala Phe
65                  70                  75                  80

Ala Ala Thr Phe Met Ala Val Leu Asp Lys Val Val Val Leu Asp Phe
                85                  90                  95
```

<210> SEQ ID NO 136
<211> LENGTH: 96
<212> TYPE: PRT
<213> ORGANISM: Triticum aestivum
<220> FEATURE:
<221> NAME/KEY: misc_feature
<222> LOCATION: (18)..(20)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid

<400> SEQUENCE: 136

```
Lys His Leu Cys Leu Val Arg Phe Lys Glu Gly Val Val Val Glu Asp
1               5                   10                  15

Ile Xaa Xaa Xaa Ile Glu Glu Leu Thr Lys Leu Ala Ala Glu Leu Asp
                20                  25                  30

Thr Val Lys Phe Phe Gly Trp Gly Lys Asp Val Leu Asn Gln Glu Ala
                35                  40                  45

Xaa Leu Thr Gln Gly Phe Thr His Val Phe Ser Met Ser Phe Ala Ser
    50                  55                  60

Ala Glu Asp Leu Ala Ala Cys Met Gly His Glu Lys His Ser Ala Phe
65                  70                  75                  80

Ala Ala Thr Phe Met Ala Val Leu Asp Lys Val Val Val Leu Asp Phe
                85                  90                  95
```

<210> SEQ ID NO 137
<211> LENGTH: 96
<212> TYPE: PRT
<213> ORGANISM: Triticum aestivum
<220> FEATURE:
<221> NAME/KEY: misc_feature
<222> LOCATION: (18)..(20)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid

<400> SEQUENCE: 137

```
Lys His Leu Cys Met Ala Lys Phe Lys Glu Gly Val Val Val Glu Asp
1               5                   10                  15

Ile Xaa Xaa Xaa Ile Gln Glu Leu Thr Lys Leu Ala Ala Glu Leu Asp
                20                  25                  30

Thr Val Lys Tyr Phe Gly Trp Gly Lys Asp Val Leu Asn Gln Glu Ala
                35                  40                  45

Xaa Leu Thr Gln Gly Phe Thr His Val Phe Val Met Thr Phe Ala Ser
    50                  55                  60

Ala Glu Asp Leu Ala Ala Cys Met Gly His Glu Lys His Thr Ala Phe
65                  70                  75                  80

Ala Ala Thr Phe Met Ala Ala Leu Asp Lys Val Val Val Met Asp Phe
                85                  90                  95
```

-continued

```
<210> SEQ ID NO 138
<211> LENGTH: 97
<212> TYPE: PRT
<213> ORGANISM: Oryza sativa
<220> FEATURE:
<221> NAME/KEY: misc_feature
<222> LOCATION: (15)..(17)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid

<400> SEQUENCE: 138

Val Lys His Leu Cys Leu Val Lys Phe Lys Glu Glu Val Leu Xaa Xaa
1               5                   10                  15

Xaa Val Asp Asp Ile Leu Gln Gly Met Thr Lys Leu Val Ser Glu Met
            20                  25                  30

Asp Met Val Lys Ser Phe Glu Trp Gly Lys Asp Val Xaa Leu Asn Gln
        35                  40                  45

Glu Met Leu Thr Gln Gly Phe Thr His Val Phe Ser Leu Thr Phe Ala
    50                  55                  60

Ser Ser Glu Asp Leu Thr Thr Tyr Met Ser His Glu Arg His Gln Glu
65                  70                  75                  80

Phe Ala Gly Thr Phe Met Ala Ala Ile Asp Lys Val Val Val Asp
                85                  90                  95

Phe

<210> SEQ ID NO 139
<211> LENGTH: 104
<212> TYPE: PRT
<213> ORGANISM: Sorghum bicolor
<220> FEATURE:
<221> NAME/KEY: misc_feature
<222> LOCATION: (40)..(42)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid

<400> SEQUENCE: 139

Arg Arg Pro Thr Met Gly Glu Val Lys His Leu Cys Leu Val Lys Phe
1               5                   10                  15

Lys Glu Gly Val Val Glu Asp Val Leu Lys Gly Met Thr Asp Leu
            20                  25                  30

Val Ala Gly Met Asp Met Val Xaa Xaa Xaa Lys Ser Phe Glu Trp Gly
        35                  40                  45

Gln Asp Val Xaa Leu Asn Gln Glu Met Leu Thr Gln Gly Phe Thr His
    50                  55                  60

Val Phe Ser Leu Thr Phe Ala Phe Ala Asp Asp Leu Ala Thr Tyr Met
65                  70                  75                  80

Gly His Asp Arg His Ala Ala Phe Ala Ala Thr Phe Met Ala Ala Leu
                85                  90                  95

Asp Lys Val Val Val Ile Asp Phe
            100

<210> SEQ ID NO 140
<211> LENGTH: 77
<212> TYPE: PRT
<213> ORGANISM: Zea mays
<220> FEATURE:
<221> NAME/KEY: misc_feature
```

```
<222> LOCATION: (25)..(25)
<223> OTHER INFORMATION: Xaa can be any naturally occurring amino acid

<400> SEQUENCE: 140

Glu Ser Thr Phe Glu Ser Thr Glu Gly Ile Lys Glu Tyr Ile Glu His
1               5                   10                  15

Pro Ala His Val Glu Phe Ala Lys Xaa Leu Asn Gln Glu Met Leu Thr
            20                  25                  30

Gln Gly Phe Thr His Val Phe Ser Leu Thr Phe Ala Thr Ala Ala Asp
        35                  40                  45

Leu Ala Ala Tyr Met Ala His Asp Ser His Thr Ala Phe Ala Ala Thr
    50                  55                  60

Phe Met Ala Ala Ile Asp Lys Val Leu Val Val Asp Phe
65                  70                  75

<210> SEQ ID NO 141
<211> LENGTH: 97
<212> TYPE: PRT
<213> ORGANISM: Lycopersicon esculentum
<220> FEATURE:
<221> NAME/KEY: misc_feature
<222> LOCATION: (32)..(34)
<223> OTHER INFORMATION: Xaa can be any naturally occurring amino acid
<220> FEATURE:
<221> NAME/KEY: misc_feature
<222> LOCATION: (44)..(45)
<223> OTHER INFORMATION: Xaa can be any naturally occurring amino acid

<400> SEQUENCE: 141

Lys His Leu Val Leu Val Lys Phe Lys Glu Asp Val Val Val Glu Asp
1               5                   10                  15

Ile Leu Lys Glu Leu Glu Lys Leu Val Gln Glu Met Asp Ile Val Xaa
            20                  25                  30

Xaa Xaa Lys Ser Phe Val Trp Gly Lys Asp Val Xaa Xaa Glu Ser His
        35                  40                  45

Glu Met Leu Arg Gln Gly Phe Thr His Ala Ile Ile Met Thr Phe Asn
    50                  55                  60

Ser Lys Glu Asp Tyr Gln Thr Phe Ala Asn His Pro Asn His Val Gly
65                  70                  75                  80

Phe Ser Ala Thr Phe Ala Thr Val Ile Asp Lys Ala Val Leu Leu Asp
                85                  90                  95

Phe

<210> SEQ ID NO 142
<211> LENGTH: 94
<212> TYPE: PRT
<213> ORGANISM: Solanum tuberosum
<220> FEATURE:
<221> NAME/KEY: misc_feature
<222> LOCATION: (29)..(31)
<223> OTHER INFORMATION: Xaa can be any naturally occurring amino acid
<220> FEATURE:
<221> NAME/KEY: misc_feature
<222> LOCATION: (41)..(42)
<223> OTHER INFORMATION: Xaa can be any naturally occurring amino acid
<220> FEATURE:
<221> NAME/KEY: misc_feature
<222> LOCATION: (75)..(76)
<223> OTHER INFORMATION: Xaa can be any naturally occurring amino acid

<400> SEQUENCE: 142

Leu Leu Val Lys Phe Lys Gln Asp Val Val Glu Glu Asp Val Leu Lys
1               5                   10                  15
```

```
Gln Ile Glu Gln Leu Val Asn Glu Ile Asp Leu Ile Xaa Xaa Xaa Lys
             20                  25                  30

Ser Phe Val Trp Gly Lys Asp Thr Xaa Xaa Glu Ser Asn Glu Met Val
         35                  40                  45

Thr Gln Gly Tyr Thr His Ala Met Ile Met Thr Phe Asn Ser Lys Glu
     50                  55                  60

Asp Tyr Glu Ala Cys Val Val Lys Glu Val Xaa Xaa Glu Phe Ser Ala
 65              70                  75                  80

Ile Phe Val Thr Val Val Glu Lys Ile Leu Val Leu Asn Phe
             85                  90

<210> SEQ ID NO 143
<211> LENGTH: 96
<212> TYPE: PRT
<213> ORGANISM: Glycine max
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (43)..(44)
<223> OTHER INFORMATION: Xaa can be any naturally occurring amino acid

<400> SEQUENCE: 143

His Tyr Val Ile Val Lys Phe Lys Asp Gly Val Ala Xaa Xaa Xaa Val
 1               5                  10                  15

Asp Asp Leu Ile Gln Gly Leu Glu Lys Met Val Phe Gly Ile Asp His
             20                  25                  30

Val Lys Ser Phe Glu Trp Gly Lys Asp Ile Xaa Xaa Glu Ser His Asp
         35                  40                  45

Met Leu Arg Gln Gly Phe Thr His Ala Phe Leu Met Thr Phe Asn Gly
     50                  55                  60

Lys Glu Glu Phe Asn Ala Phe Gln Thr His Pro Asn His Leu Glu Phe
 65              70                  75                  80

Ser Gly Val Phe Ser Pro Ala Ile Glu Lys Ile Val Leu Asp Phe
             85                  90                  95

<210> SEQ ID NO 144
<211> LENGTH: 96
<212> TYPE: PRT
<213> ORGANISM: Glycine max
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (43)..(44)
<223> OTHER INFORMATION: Xaa can be any naturally occurring amino acid

<400> SEQUENCE: 144

His Tyr Val Ile Val Lys Phe Lys Asp Gly Val Ala Xaa Xaa Xaa Val
 1               5                  10                  15

Asp Glu Leu Ile Gln Gly Leu Glu Lys Met Val Ser Gly Ile Asp His
             20                  25                  30

Val Lys Ser Phe Glu Trp Gly Lys Asp Ile Xaa Xaa Glu Ser His Asp
         35                  40                  45

Met Leu Arg Gln Gly Phe Thr His Val Phe Leu Met Ala Phe Asn Gly
     50                  55                  60

Lys Glu Glu Phe Asn Ala Phe Gln Thr His Pro Asn His Leu Glu Phe
 65              70                  75                  80
```

```
Thr Gly Val Phe Ser Pro Ala Ile Glu Lys Ile Val Val Leu Asp Phe
                85                  90                  95

<210> SEQ ID NO 145
<211> LENGTH: 97
<212> TYPE: PRT
<213> ORGANISM: Glycine max
<220> FEATURE:
<221> NAME/KEY: misc_feature
<222> LOCATION: (14)..(16)
<223> OTHER INFORMATION: Xaa can be any naturally occurring amino acid
<220> FEATURE:
<221> NAME/KEY: misc_feature
<222> LOCATION: (44)..(45)
<223> OTHER INFORMATION: Xaa can be any naturally occurring amino acid

<400> SEQUENCE: 145

Lys His Phe Val Ile Val Lys Phe Lys Glu Gly Val Ala Xaa Xaa Xaa
1               5                   10                  15

Val Asp Glu Leu Thr Lys Gly Met Glu Lys Leu Val Thr Glu Ile Gly
                20                  25                  30

Ala Val Lys Ser Phe Glu Trp Gly Gln Asp Ile Xaa Xaa Glu Ser Leu
            35                  40                  45

Asp Val Leu Arg Gln Gly Phe Thr His Ala Phe Leu Met Thr Phe Asn
        50                  55                  60

Lys Lys Glu Asp Phe Val Ala Phe Gln Ser His Pro Asn His Val Glu
65                  70                  75                  80

Phe Ser Thr Lys Phe Ser Ala Ala Ile Glu Asn Ile Val Leu Leu Asp
                85                  90                  95

Phe

<210> SEQ ID NO 146
<211> LENGTH: 43
<212> TYPE: PRT
<213> ORGANISM: Glycine max
<220> FEATURE:
<221> NAME/KEY: misc_feature
<222> LOCATION: (18)..(19)
<223> OTHER INFORMATION: Xaa can be any naturally occurring amino acid

<400> SEQUENCE: 146

Leu Val Ser Glu Ile His Ala Val Lys Ser Phe Glu Trp Gly Gln Asp
1               5                   10                  15

Ile Xaa Xaa Glu Ser Leu Asp Val Leu Arg Gln Gly Phe Thr His Ala
                20                  25                  30

Phe Leu Met Thr Phe Asn Lys Lys Arg Arg Leu
            35                  40

<210> SEQ ID NO 147
<211> LENGTH: 111
<212> TYPE: PRT
<213> ORGANISM: Arabidopsis thaliana

<400> SEQUENCE: 147

Met Ala Thr Ser Gly Phe Lys His Leu Val Val Lys Phe Lys Glu
1               5                   10                  15

Asp Thr Lys Val Asp Glu Ile Leu Lys Gly Leu Glu Asn Leu Val Ser
                20                  25                  30

Gln Ile Asp Thr Val Lys Ser Phe Glu Trp Gly Glu Asp Lys Glu Ser
            35                  40                  45

His Asp Met Leu Arg Gln Gly Phe Thr His Ala Phe Ser Met Thr Phe
```

```
                50                  55                  60
Glu Asn Lys Asp Gly Tyr Val Ala Phe Thr Ser His Pro Leu His Val
 65                  70                  75                  80

Glu Phe Ser Ala Ala Phe Thr Ala Val Ile Asp Lys Ile Val Leu Leu
                 85                  90                  95

Asp Phe Pro Val Ala Ala Val Lys Ser Ser Val Val Ala Thr Pro
            100                 105                 110

<210> SEQ ID NO 148
<211> LENGTH: 100
<212> TYPE: PRT
<213> ORGANISM: Glycine max
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (55)..(56)
<223> OTHER INFORMATION: Xaa can be any naturally occurring amino acid

<400> SEQUENCE: 148

Lys Thr Val Glu His Ile Val Leu Phe Lys Val Lys Glu Thr Glu
 1                5                  10                  15

Pro Ser Lys Val Ser Asp Met Val Asn Gly Leu Gly Ser Leu Val Ser
                 20                  25                  30

Leu Asp Pro Val Leu His Xaa Leu Ser Val Gly Pro Leu Leu Arg Asn
             35                  40                  45

Arg Ser Ser Ala Leu Thr Xaa Xaa Phe Thr His Met Leu His Ser Arg
 50                  55                  60

Tyr Lys Ser Lys Glu Asp Leu Glu Ala Tyr Ser Ala His Pro Ser His
 65                  70                  75                  80

Val Ser Val Val Lys Gly Tyr Val Leu Pro Ile Ile Asp Asp Ile Met
                 85                  90                  95

Ser Val Asp Trp
            100

<210> SEQ ID NO 149
<211> LENGTH: 567
<212> TYPE: DNA
<213> ORGANISM: Populus tremula

<400> SEQUENCE: 149
atccacagag agaaagggaa gacatggcaa ccagaactcc aaagcttgtg aagcacacat      60
tgttgactcg gttcaaggat gagatcacac gagaacagat cgacaactac attaatgact     120
ataccaatct gctcgatctc attccaagca tgaagagttt caattggggc acggatctgg     180
gcatggagtc tgcggagcta aaccgaggat acactcatgc ctttgaatct acatttgaga     240
gcaagtctgg tttgcaagag tacctcgatt ctgctgctct tgctgcattt gcagaagggt     300
ttttgcctac tttgtcacag cgtcttgtga tagactactt tctctactaa acgctcagga     360
gtaacgactt cggccgggct atttcatggt aataaagtaa tgtaatgttc aataaatgct     420
ggttttgaac cactgaatgt tcgtgtcttg atttcttgtc tgtgctaagt gaagggagtg     480
ctgctattcc tttaaaaata aagcccttgg ggttgagttg tagtttttca atcttttcc      540 ccgatttatt tcggtcttgg tgttgtt                                        567

<210> SEQ ID NO 150
<211> LENGTH: 351
```

-continued

```
<212> TYPE: DNA
<213> ORGANISM: Arabidopsis thaliana

<400> SEQUENCE: 150
atggaggaag caaagggacc tgtgaagcac gtattgcttg ctagtttcaa agatggggtt      60
agtcctgaga aaatcgaaga gctcatcaaa ggttacgcca atctcgtcaa tctcatcgaa     120
cctatgaaag ctttccactg gggaaaagat gtgagcattg agaatctgca tcaaggttac     180
acacacatct ttgaatccac atttgagagt aaagaagctg ttgcagagta cattgctcat     240
cctgctcacg ttgaattcgc caccatcttc cttggcagct tggataaagt tttggttatt     300
gactacaagc ctacctctgt ctctctctaa ttatcttgta gcagcatttt c              351

<210> SEQ ID NO 151
<211> LENGTH: 4
<212> TYPE: PRT
<213> ORGANISM: Artificial sequence
<220> FEATURE:
<223> OTHER INFORMATION: A tumor specific peptide

<400> SEQUENCE: 151

Cys Arg Gly Asp
1

<210> SEQ ID NO 152
<211> LENGTH: 4
<212> TYPE: PRT
<213> ORGANISM: Artificial sequence
<220> FEATURE:
<223> OTHER INFORMATION: A tumor specific peptide

<400> SEQUENCE: 152

Arg Gly Asp Cys
1
```